US008609105B2

(12) United States Patent
Senter et al.

(10) Patent No.: US 8,609,105 B2
(45) Date of Patent: Dec. 17, 2013

(54) AURISTATIN DRUG LINKER CONJUGATES

(75) Inventors: Peter Senter, Seattle, WA (US); Svetlana Doronina, Snohomish, WA (US); Timothy Bovee, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 365 days.

(21) Appl. No.: 12/933,364

(22) PCT Filed: Mar. 18, 2009

(86) PCT No.: PCT/US2009/037582
§ 371 (c)(1),
(2), (4) Date: Sep. 17, 2010

(87) PCT Pub. No.: WO2009/117531
PCT Pub. Date: Sep. 24, 2009

(65) Prior Publication Data
US 2011/0020343 A1 Jan. 27, 2011

Related U.S. Application Data

(60) Provisional application No. 61/044,431, filed on Apr. 11, 2008, provisional application No. 61/037,705, filed on Mar. 18, 2008.

(51) Int. Cl.
| A61K 39/395 | (2006.01) |
| A61K 39/42 | (2006.01) |
| A61K 38/03 | (2006.01) |
| A61K 38/08 | (2006.01) |
| A61K 38/10 | (2006.01) |
| G01N 33/48 | (2006.01) |
| G01N 33/567 | (2006.01) |
| G01N 33/574 | (2006.01) |
| G01N 33/577 | (2006.01) |
| C07K 16/28 | (2006.01) |
| C07K 16/46 | (2006.01) |
| C12N 5/07 | (2010.01) |
| C12N 5/09 | (2010.01) |
| C12N 5/078 | (2010.01) |

(52) U.S. Cl.
USPC ............ 424/179.1; 424/183.1; 435/7.21; 435/7.23; 435/7.24; 435/375; 514/3.7; 514/19.3; 514/21.4; 514/21.5; 514/21.6; 514/21.7; 514/21.8; 530/323; 530/326; 530/327; 530/328; 530/329; 530/391.7; 530/391.9

(58) Field of Classification Search
None
See application file for complete search history.

(56) References Cited

U.S. PATENT DOCUMENTS

| 4,978,744 A | 12/1990 | Pettit et al. |
| 5,410,024 A | 4/1995 | Pettit et al. |
| 5,635,483 A | 6/1997 | Pettit et al. |
| 5,654,399 A | 8/1997 | Sakakibara et al. |
| 5,767,237 A | 6/1998 | Sakakibara et al. |
| 5,780,588 A | 7/1998 | Pettit et al. |
| 5,840,699 A | 11/1998 | Sakakibara et al. |
| 6,004,934 A | 12/1999 | Sakakibara et al. |
| 6,124,431 A | 9/2000 | Sakakibara et al. |
| 6,214,345 B1 | 4/2001 | Firestone et al. |
| 6,569,834 B1 | 5/2003 | Pettit et al. |
| 6,620,911 B1 | 9/2003 | Pettit et al. |
| 6,884,869 B2 | 4/2005 | Senter et al. |
| 7,091,186 B2 | 8/2006 | Senter et al. |
| 7,098,308 B2 | 8/2006 | Senter et al. |
| 7,256,257 B2 | 8/2007 | Senter et al. |
| 7,375,078 B2 | 5/2008 | Feng |
| 7,423,116 B2 | 9/2008 | Senter et al. |
| 7,498,298 B2 | 3/2009 | Doronina et al. |
| 7,553,816 B2 | 6/2009 | Senter et al. |
| 7,659,241 B2 | 2/2010 | Senter et al. |
| 7,662,387 B2 | 2/2010 | Law et al. |
| 7,745,394 B2 | 6/2010 | Doronina et al. |
| 7,754,681 B2 | 7/2010 | Feng |
| 7,829,531 B2 | 11/2010 | Senter et al. |
| 7,851,437 B2 | 12/2010 | Senter et al. |
| 7,964,566 B2 | 6/2011 | Doronina et al. |
| 7,964,567 B2 | 6/2011 | Doronina et al. |
| 7,989,434 B2 | 8/2011 | Feng |
| 7,994,135 B2 | 8/2011 | Doronina et al. |
| 8,343,928 B2 | 1/2013 | Doronina et al. |
| 2002/0001587 A1 | 1/2002 | Erickson et al. |
| 2002/0142955 A1 | 10/2002 | Dubois et al. |
| 2003/0083263 A1 | 5/2003 | Doronina et al. |
| 2003/0096743 A1 | 5/2003 | Senter et al. |
| 2003/0130189 A1 | 7/2003 | Senter et al. |
| 2004/0018194 A1 | 1/2004 | Francisco et al. |

(Continued)

FOREIGN PATENT DOCUMENTS

| CA | 2114156 A1 | 7/1994 |
| JP | 06-234790 A | 8/1994 |

(Continued)

OTHER PUBLICATIONS

Carl, P.L. et al., "A novel connector linkage applicable in prodrug design," Journal of Medicinal Chemistry, May 1981, vol. 24, No. 5, pp. 479-480.

Doronina et al., "Development of potent monoclonal antibody auristatin conjugates for cancer therapy," Nature Biotechnology, 21(7):778-784 (2003) + Erratum, Nature Biotechnology, 21(8):941 (2003).

Doronina et al., "Enhanced Activity of Monomethylauristatin F through Monoclonal Antibody Delivery: Effects of Linker Technology on Efficacy and Toxicity," Bioconjugate Chem., 17:114-124 (2006).

Doronina et al., "Immunoconjugates comprised of drugs with impaired cellular permeability: A new approach to targeted therapy," SciFinder search result, abstract of paper from 228th ACS National Meeting held in Philadelphia, PA, Aug. 22-26, 2004.

(Continued)

Primary Examiner — Karen Canella
(74) Attorney, Agent, or Firm — Seattle Genetics, Inc.

(57) ABSTRACT

Drug Linker compounds and Drug Linker Ligand conjugates are provided that have auristatins linked via the C-terminus. The conjugates show efficacy without the need for a self-immolative group to release the drug.

46 Claims, 9 Drawing Sheets

(56) References Cited

U.S. PATENT DOCUMENTS

| | | |
|---|---|---|
| 2004/0235068 A1 | 11/2004 | Levinson |
| 2005/0009751 A1 | 1/2005 | Senter et al. |
| 2005/0113308 A1 | 5/2005 | Senter et al. |
| 2005/0238649 A1* | 10/2005 | Doronina et al. ......... 424/178.1 |
| 2005/0256030 A1 | 11/2005 | Feng |
| 2005/0272665 A1 | 12/2005 | Schmid et al. |
| 2006/0073152 A1 | 4/2006 | Dennis |
| 2006/0074008 A1 | 4/2006 | Senter et al. |
| 2006/0128970 A1 | 6/2006 | Bliss et al. |
| 2006/0182751 A1 | 8/2006 | Gazzard et al. |
| 2006/0229253 A1 | 10/2006 | Senter et al. |
| 2006/0233794 A1 | 10/2006 | Law et al. |
| 2007/0134243 A1 | 6/2007 | Gazzard et al. |
| 2009/0018086 A1 | 1/2009 | Doronina et al. |
| 2009/0111756 A1 | 4/2009 | Doronina et al. |

FOREIGN PATENT DOCUMENTS

| | | |
|---|---|---|
| JP | 09-77791 A | 3/1997 |
| WO | WO 99/35164 A1 | 7/1999 |
| WO | WO 01/18032 A2 | 3/2001 |
| WO | WO 02/15700 A1 | 2/2002 |
| WO | WO02088172 * | 11/2002 |
| WO | WO 03/008378 A1 | 1/2003 |
| WO | WO 03/034903 A2 | 5/2003 |
| WO | WO 03/043583 A2 | 5/2003 |
| WO | WO 2004/010957 A2 | 2/2004 |
| WO | WO 2004/032828 A2 | 4/2004 |
| WO | WO 2004/073656 A2 | 9/2004 |
| WO | WO 2005/081711 A2 | 9/2005 |
| WO | WO 2005/082023 A2 | 9/2005 |
| WO | WO 2006/034488 A2 | 3/2006 |
| WO | WO 2007/008603 A1 | 1/2007 |
| WO | WO 2007/008848 A2 | 1/2007 |
| WO | WO 2007/109567 A1 | 9/2007 |

OTHER PUBLICATIONS

Doronina et al., "Novel Peptide Linkers for Highly Potent Antibody-Auristatin Conjugates," Poster presentation of Abstract 4907 at the 2008 Annual Meeting of the AACR, Apr. 12-16, 2008 in San Diego, CA.

Doronina et al., "Novel peptide linkers for highly potent antibody-auristatin conjugate," Bioconjugate Chem, 19:1960-1963 (2008).

Francisco et al., "cAC10-vcMMAE, an anti-CD30-monomethyl auristatin E conjugate with potent and selective antitumor activity," Blood, 102(4)1458-1465 (2003).

Hamblett et al., "Effect of drug loading on the pharmacology, pharmacokinetics, and toxicity of an anti-CD30 antibody-drug conjugate," Proceedings of the AACR, vol. 45, abstract # 624 (2004).

Kline et al., "Novel Antitumor Prodrugs Designed for Activation by Matrix Metalloproteinases-2 and -9," Molecular Pharmaceutics, 1(1):9-22 (2004).

Klussman et al., "Secondary mAb—vcMMAE conjugates are highly sensitive reporters of antibody internalization via the lysosome pathway," Bioconjug Chem., 15(4):765-773 (2004).

Law et al., "CD70 is expressed on renal cell carcinoma and is a potential target for tumor cell elimination by antibody-drug conjugates," Proceedings of the AACR, vol. 45, abstract # 625 (2004).

Meyer et al., "Recent Advances in Antibody Drug Conjugates for Cancer Therapy," Annual Reports in Medical Chemistry, 38(chapter 23):229-237 (2003).

Miyazaki et al., "Synthesis and Antitumor Activity of Novel Dolastatin 10 Analogs," Chem. Pharm. Bull., 43(10):1706-1718 (1995).

Petit et al., "Antineoplastic agents 337. Synthesis of dolastatin 10 structural modifications," Anti-Cancer Drug Design, 10:529-544 (1995).

Pettit et al., "Specific Activities of Dolastatin 10 and Peptide Derivatives against *Cryptococcus neoformans*," Antimicrobial Agents and Chemotherapy, 42(11):2961-2965 (1998).

Pettit et al., "A Cobalt—Phosphine Complex Directed Reformatsky Approach to a Stereospecific Synthesis of the Dolastatin 10 Unit Dolaproine (Dap)1," J. Org. Chem., 66:8640-8642 (2001).

Pettit et al., "The Absolute Configuration and Synthesis of Natural (−)-Dolastatin 10," J. Am. Chem. Soc., 111:5463-5465 (1989).

Pettit et al., "Dolastatins 24. Synthesis of (−) -dolastatin 10. X-Ray molecular structure of N,N-dimethylvalyl-valyl-dolaisoleuine tert-butyl ester," J. Chem. Soc. Perkin Trans.1, 5:859-863 (1996).

Pettit at al., "Antineoplastic agents 365. Dolastatin 10 SAR probes," Anticancer Drug Des., 13(4):243-277 (1998).

Press Release, "Seattle Genetics, Inc. (SGEN) to Present Advances in Preclinical Research at American Cancer Research Annual Meeting," Mar. 24, 2004, downloaded from internet on Aug. 31, 2004.

Senter et al., "Immunoconjugates comprised of drugs with Impaired cellular permeability: A new approach to targeted therapy," Proceedings of the AACR, vol. 45, abstract # 623 (2004).

Toki et al., "Protease-Mediated Fragmentation of p-Amidobenzyl Ethers: A New Strategy for the Activation of Anticancer Prodrugs," J. Org. Chem., 67:1866-1872 (2002).

Woyke et al., "Effect of auristatin PHE on microtube integrity and nuclear localization in *Cryptococcus neoformans*," Antimicrobial Agents and Chemotherapy, 46(12):3802-3808 (2003).

Woyke et al., "In Vitro Activities and Postantifungal Effects of the Potent Dolastatin 10 Derivative Auristatin PHE," Antimicrobial Agents and Chemotherapy, 45(12):3580-3584 (2001).

* cited by examiner

AURISTATIN DRUG LINKER CONJUGATES

CONTINUITY

This application is the national stage application under 35 U.S.C. §371 of International Application No. PCT/US2009/037582, filed Mar. 18, 2009, which claims the benefit of U.S. Provisional Patent Application No. 61/037,705, filed Mar. 18, 2008, and U.S. Provisional Patent Application No. 61/044,431, filed Apr. 11, 2008, each of which is incorporated herein in its entirety.

FIELD OF THE INVENTION

The present invention is directed to auristatin-based conjugates, such as Drug Linker Ligand conjugates and Drug Linker compounds, as well as to compositions including the same, and to methods for using the same to treat cancer, an autoimmune disease, an infectious disease and other pathological conditions. The invention also relates to methods of using such conjugates in vitro, in situ, and in vivo for the detection, diagnosis or treatment of mammalian cells, or associated pathological conditions.

BACKGROUND OF THE INVENTION

A great deal of interest has surrounded the use of monoclonal antibodies (mAbs) for the selective delivery of cytotoxic agents to tumor cells. While a number of different drug classes have been tried for delivery via antibodies, only a few drug classes have proved efficacious as antibody drug conjugates, while having a suitable toxicity profile. One such class is the auristatins, derivatives of the natural product dolastatin 10. Representative auristatins include MMAE (N-methylvaline-valine-dolaisoleuine-dolaproine-norephedrine) and MMAF (N-methylvaline-valine-dolaisoleuine-dolaproine-phenylalanine).

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

MMAF is relatively non-toxic as a free drug, yet is highly potent in activity when conjugated to a mAb and internalized. MMAF has been successfully conjugated to a mAb at the N-terminal amino acid of MMAF via a cathepsin B cleavable peptide linker maleimidocaproyl-valine-citrulline (mc-vc-) and a self-immolative group p-aminobenzyl-carbamoyl (PABC) to produce antibody-linker-drug conjugates of the following structure mAb-mc-vc-PABC-MMAF. Upon cleavage of the peptide linker, the self-immolative PABC group releases itself from MMAF, liberating free drug.

MMAF was also found to be active as non-cleavable drug linker conjugate, maleimidocaproyl MMAF (mcMMAF). For mcMMAF the maleimidocaproyl and a cysteine from the antibody remain attached to the N-terminus of MMAF.

There remains a need, however, for drug delivery vehicles for the selective release of drug to cells.

SUMMARY OF THE INVENTION

The present invention is based on the unexpected discovery that ligand drug conjugates comprising an auristatin having a free C-terminal carboxyl group conjugated directly to a peptide linker via a peptide bond are active as drug delivery agents in vitro and in vivo.

In one aspect, the present invention provides Drug Linker compounds represented by the general formula:

D-LU            (I)

or a pharmaceutically acceptable salt or solvate thereof, wherein LU is a Linker unit and D is an auristatin having a C-terminal carboxyl group that forms an amide bond with the Linker unit. The Linker unit comprises at least one amino acid.

In another aspect, the present invention provides Drug Linker Ligand conjugates in which the Drug Linker compounds further comprise a Ligand unit (L). The conjugates are represented by the general formula (II):

L-(LU-D)$_p$            (II)

or a pharmaceutically acceptable salt or solvate thereof. D is an auristatin having a C-terminal carboxyl group that forms an amide bond with the Linker unit. The Linker unit comprises at least one amino acid.

In some embodiments, the auristatin has the following formula:

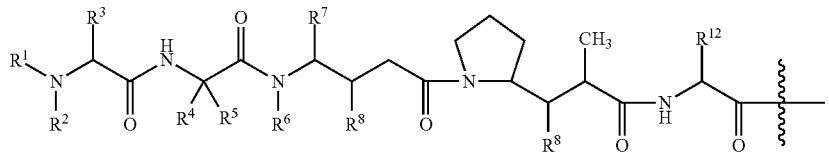

wherein the wavy line indicates the attachment to a Linker unit (LU);

$R^1$ and $R^2$ is independently selected from the group consisting of hydrogen (H) and —$C_1$-$C_8$ alkyl; with the proviso that both $R^1$ and $R^2$ are not H;

$R^3$ is selected from the group consisting of H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);

$R^4$ is selected from the group consisting of H, —$C_1$-$C_8$ alkyl, —$C_3$-$C_8$ carbocycle, -aryl, —$X^1$-aryl, —$X^1$—($C_3$-$C_8$ carbocycle), —$C_3$-$C_8$ heterocycle and —$X^1$—($C_3$-$C_8$ heterocycle);

$R^5$ is selected from the group consisting of H and methyl;

or $R^4$ and $R^5$ jointly form a carbocyclic ring and have the formula —$(CR^aR^b)_n$—, wherein $R^a$ and $R^b$ are independently selected from the group consisting of H and —$C_1$-$C_8$ alkyl and n is selected from the group consisting of 2, 3, 4, 5 and 6;

$R^6$ is selected from the group consisting of H and —$C_1$-$C_8$ alkyl;

$R^7$ is selected from the group consisting of H, $-C_1-C_8$ alkyl, $-C_3-C_8$ carbocycle, aryl, $-X^1$-aryl, $-X^1-(C_3-C_8$ carbocycle), $-C_3-C_8$ heterocycle and $-X^1-(C_3-C_8$ heterocycle);

each $R^8$ is independently selected from the group consisting of H, $-OH$, $-C_1-C_8$ alkyl, $-C_3-C_8$ carbocycle and $-O-(C_1-C_8$ alkyl);

$R^{12}$ is selected from H, $-C_1-C_8$ alkyl, aryl, $-X^1$aryl, $-C_3-C_8$ carbocycle, $-X^1-(C_3-C_8$ carbocycle), $-C_1-C_8$ alkylene-$NH_2$, $-C_3-C_8$ heterocycle and $-X^1-(C_3-C_8$ heterocycle); and each $X^1$ is independently $-C_1-C_{10}$ alkylene;

or a pharmaceutically acceptable salt or solvate thereof.

In some embodiments, $R^4$ and $R^{12}$ are each independently selected from a side chain of a natural amino acid. In some embodiments, $R^{12}$ is the side chain of phenylalanine. In some embodiments, $R^{12}$ is the side chain of methionine. In some embodiments, $R^{12}$ is the side chain of tryptophan.

In some embodiments, the auristatin has the following formula:

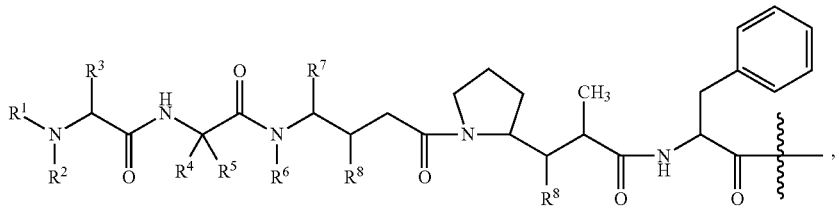

wherein $R^1$-$R^8$ are as specified above.

In some embodiments, the Linker unit LU has the formula $-W_w-A_a$, wherein:

$W_w$ is a sequence of at least one independently selected amino acid diradicals;

w is an integer ranging from 1 to 12;

A is a Stretcher unit;

a is 1 or 2;

or a pharmaceutically acceptable salt or solvate thereof.

In some embodiments, the Stretcher unit A is $-NH-R^9-R^{11}$ or $-O-R^9-R^{11}$, wherein $-R^9-R^{11}$ has the formula:

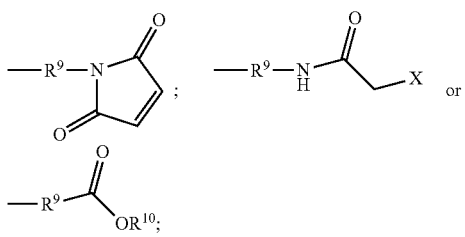

wherein $R^9$ can be selected from the group consisting of $-C_1-C_{10}$ alkylene-, $-C_3-C_8$ carbocyclo-, -arylene-, $-C_1-C_{30}$ heteroalkylene-, $-C_3-C_8$ heterocyclo-, $-C_1-C_{10}$ alkylene-arylene-, -arylene-$C_1-C_{10}$ alkylene-, $-C_1-C_{10}$ alkylene-$(C_3-C_8$ carbocyclo)-, $-(C_3-C_8$carbocyclo)-$C_1-C_{10}$ alkylene-, alkylene-$(C_3-C_8$ heterocyclo)-, and $-(C_3-C_8$ heterocyclo)-$C_1-C_{10}$ alkylene-;

wherein X is a leaving group; and each $R^{10}$ forms an activated ester, wherein $R^{10}$ is independently selected from the group consisting of H, $-C_1-C_{10}$ alkyl, $-C_3-C_8$ carbocyclo, aryl, $-C_1-C_{10}$ heteroalkyl, $-C_3-C_8$ heterocyclo, $-C_1-C_{10}$ alkylene-aryl, -arylene-$C_1-C_{10}$ alkyl, $-C_1-C_{10}$ alkylene-$(C_3-C_8$ carbocyclo), $-(C_3-C_8$ carbocyclo)-$C_1-C_{10}$ alkyl, $-C_1-C_{10}$ alkylene-$(C_3-C_8$ heterocyclo), and $-(C_3-C_8$ heterocyclo)-$C_1-C_{10}$ alkyl.

In some embodiments of the Stretcher unit A, $-NH-R^9-$ is selected from $-NH-C_1-C_{10}$ alkylene-, $-NH-C_1-C_{10}$ alkylene-$NH-C(O)-C_1-C_{10}$ alkylene-, $-NH-C_1-C_{10}$ alkylene-$C(O)-NH-C_1-C_{10}$ alkylene-, $-NH-(CH_2CH_2O)_r-$, $-NH-(CH_2CH_2O)_r-CH_2-$, $-NH-(CH_2CH_2NH)_r-(CH_2)_r$, $-NH-(CH_2CH_2NH)_r-(CH_2)_r$, $-NH-C(O)-(CH_2)$, $-NH-(C_3-C_8$ carbocyclo)-, $-NH$-(arylene-)-, and $-NH-(C_3-C_8$ heterocyclo-)-, wherein each r is independently 1-10.

In some embodiments of the Stretcher unit A, $-O-R^9-$ is selected from $-O-C_1-C_{10}$ alkylene-, $-O-C_1-C_{10}$ alkylene-$NH-C(O)-C_1-C_{10}$ alkylene-, $-O-C_1-C_{10}$ alkylene-$C(O)-NH-C_1-C_{10}$ alkylene-, $-O-(CH_2CH_2O)_r-$, $O-(CH_2CH_2O)_r-CH_2-$, $-O-(C_3-C_8$ carbocyclo)-, $-O$-(arylene)-, and $-O-(C_3-C_8$ heterocyclo-)-, wherein each r is independently 1-10.

In embodiments in which the Stretcher unit A is $-O-R^9-R^{11}-$, the ester is a hindered ester.

In some embodiments, the Linker unit (LU) is selectively stable, such that the active Drug is not readily released in blood, but is released on internalization into a target cell. The preferred linkers of this embodiment contain non-natural or D-amino acids. Improved delivery of the Drug in the Drug Linker Ligand conjugates can be achieved either due to differential processing of the conjugates in tumor versus normal cells/tissues, or due to slow drug release inside cells.

In other embodiments, the Linker unit (LU) is labile through linker proteolysis, and provides for a facile release of the active Drug near its target.

In another aspect, a Drug Linker compound is provided that can be used as an intermediate for the synthesis of a Drug Linker Ligand conjugate. The Drug Linker compounds are of particular interest for the use as intermediates for the synthesis of Drug Linker Ligand conjugates (e.g., a Drug Linker Antibody conjugate or an Antibody Drug Conjugate (ADC)). Drug Linker Ligand conjugates, such as antibody drug conjugates, are useful with any ligand, particularly antibodies against tumor antigens.

The Drug Linker Ligand conjugates are useful for treating disorders, such as cancer, autoimmune disease or infectious disease, in a patient.

In another aspect, compositions are provided that include an effective amount of a Drug Linker Ligand conjugate and a pharmaceutically acceptable carrier or vehicle.

In yet another aspect, methods for killing or inhibiting the multiplication of a tumor cell or cancer cell are provided. In still another aspect, methods for treating cancer are provided. In still another aspect, methods for killing or inhibiting the replication of a cell that expresses an autoimmune antibody are provided. In yet another aspect, methods for treating an autoimmune disease are provided. In still another aspect, methods for treating an infectious disease are provided.

In another aspect, an assay is provided for detecting cancer cells, the assay including:
(a) exposing the cells to an Drug Linker Ligand conjugate (e.g., an Antibody Drug Conjugate); and
(b) determining the extent of binding of the Drug Linker Ligand conjugate to the cells.

The invention will best be understood by reference to the following detailed description of the exemplary embodiments, taken in conjunction with the accompanying drawings, figures, and schemes. The discussion below is descriptive, illustrative and exemplary and is not to be taken as limiting the scope defined by any appended claims.

DETAILED DESCRIPTION

Definitions and Abbreviations

Figure 1:
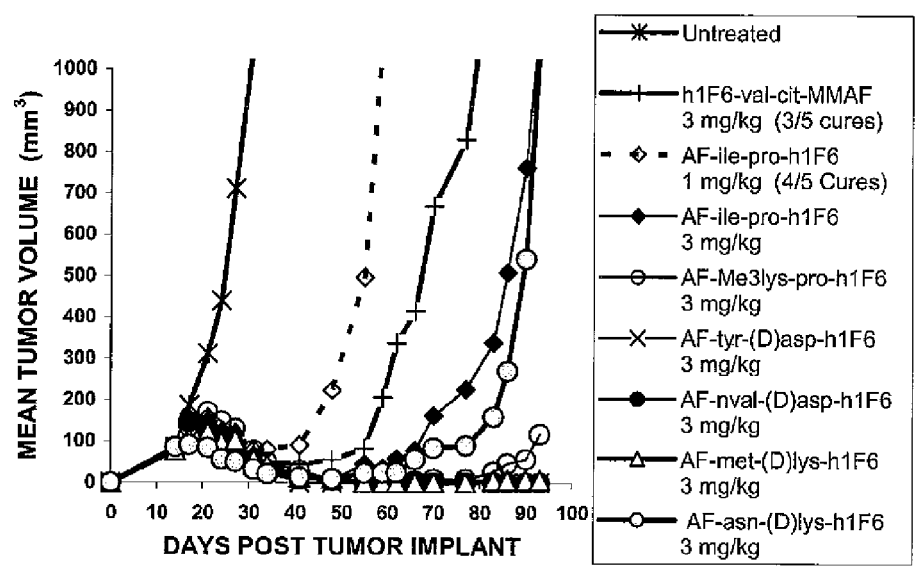
FIG. 1 shows in vivo efficacy data for Auristatin F (AF)-Dipeptide-h1F6 conjugates in nude mice bearing subcutaneous 786O renal carcinoma tumors. The mice were given a single dose ip, as indicated in the figure, on day 14.

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, *Immuno. Biology*, 5th *Ed.*, Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (*Sequences of Proteins of Immunological Interest,* 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, *J. Mol. Biol.* 196:901-917). FR residues are those variable domain residues other than the hypervariable region residues as herein defined.

A "single-chain Fv" or "scFv" antibody fragment comprises the $V_H$ and $V_L$ domains of an antibody, wherein these domains are present in a single polypeptide chain. Typically, the Fv polypeptide further comprises a polypeptide linker between the $V_H$ and $V_L$ domains which enables the scFv to form the desired structure for antigen binding. For a review of scFv, see Plückthun in *The Pharmacology of Monoclonal Antibodies,* vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, *Proc. Natl. Acad. Sci. USA* 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, *Nature* 321:522-525; Riechmann et al., 1988, *Nature* 332:323-329; and Presta, 1992, *Curr. Op. Struct. Biol.* 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. >50% of a population, of a mixture or a sample.

The term "intracellular metabolite" refers to a compound resulting from a metabolic process or reaction inside a cell on a Drug Linker Ligand conjugate (e.g., an Antibody Drug conjugate (ADC)). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on a Drug Linker Ligand conjugate (e.g., an Antibody Drug conjugate (ADC) or the like), whereby the covalent attachment, e.g., the linker, between the Drug moiety (D) and the Ligand unit (e.g., an antibody (Ab)) is broken, resulting in the free Drug, or other metabolite of the conjugate dissociated from the antibody inside the cell. The cleaved moieties of the Drug Linker Ligand conjugate are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a Drug Linker Ligand conjugate or an intracellular metabolite of a Drug Linker Ligand conjugate. Cytotoxic activity may be expressed as the $IC_{50}$ value, which is the concentration (molar or mass) per unit volume at which half the cells survive.

The term "cytotoxic agent" as used herein refers to a substance that inhibits or inhibits the function of cells and/or causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term does not include a radioactive isotope(s).

A "disorder" is any condition that would benefit from treatment with a Drug Linker Ligand conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

An "autoimmune disease" herein is a disease or disorder arising from and directed against an individual's own tissues or a co-segregate or manifestation thereof or resulting condition therefrom.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

A "native sequence" polypeptide is one which has the same amino acid sequence as a polypeptide, e.g., a tumor-associated antigen receptor, derived from nature. Such native sequence polypeptides can be isolated from nature or can be produced by recombinant or synthetic means. Thus, a native sequence polypeptide can have the amino acid sequence of a naturally-occurring human polypeptide, a murine polypeptide, or a polypeptide from any other mammalian species.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid where, for example, the nucleic acid molecule is in a chromosomal location different from that of natural cells.

The expression "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence, for example, if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, the synthetic oligonucleotide adaptors or linkers can be used in accordance with conventional practice.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a substituted or unsubstituted a straight chain or branched, saturated or unsaturated hydrocarbon having the indicated number of carbon atoms (e.g., "—$C_1$-$C_8$ alkyl" or "—$C_1$-$C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_1$-$C_8$ alkyl" groups include, but are not limited to, -methyl, -ethyl, -n-propyl, -n-butyl, -n-pentyl, -n-hexyl, -n-heptyl and -n-octyl; while branched —$C_1$-$C_8$ alkyls include, but are not limited to, -isopropyl, -sec-butyl, -isobutyl, -tert-butyl, -isopentyl, and -2-methylbutyl; unsaturated —$C_2$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexyl, 2-hexyl, -3-hexyl, -acetylenyl, -propynyl, -1-butynyl, -2-butynyl, -1-pentynyl, -2-pentynyl and -3-methyl-1 butynyl. In some embodiments, an alkyl group is unsubstituted. In other embodiments, an alkyl group is substituted with one or more groups. Preferred substitutents include: —O—($C_1$-$C_8$ alkyl), aryl, —C(O)R', —OC(O)R', —C(O)OR', —C(O)NH$_2$, —OH, —C(O)NHR', —C(O)N(R')$_2$, —NHC(O)R', —SO$_3$R', —S(O)$_2$R', —S(O)R', —SR', -halogen, —N$_3$, —NH$_2$, —NH(R'), —N(R')$_2$ and —CN; where each R' is independently selected the group consisting of H, unsubstituted $C_1$-$C_8$ alkyl and aryl. Particularly preferred substituents include: —OH, —SCH$_3$, —CONH$_2$, —COOH, —NHC(=NH)NH$_2$, —NH$_2$, —NHCOCH$_3$, —NHCHO, and —NHCONH$_2$.

"Alkenyl" refers to a substituted or unsubstituted $C_2$-$C_{18}$ hydrocarbon containing normal, secondary or tertiary carbon atoms with at least one site of unsaturation, i.e., a carbon-carbon, sp$^2$ double bond. Examples include, but are not limited to: ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH=CH$_2$).

"Alkynyl" refers to a substituted or unsubstituted $C_2$-$C_{18}$ hydrocarbon containing normal, secondary, or tertiary carbon atoms with at least one site of unsaturation, i.e., a carbon-carbon, sp triple bond. Examples include, but are not limited to: acetylenic (—C≡CH) and propargyl (—CH$_2$C≡CH).

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. A "$C_1$-$C_{10}$ alkylene" is a straight chain, saturated hydrocarbon group of the formula —(CH$_2$)$_{1-10}$—. Examples of a —$C_1$-$C_{10}$ alkylene- include methylene, ethylene, propylene, butylene, pentylene, hexylene, heptylene, ocytylene, nonylene and decalene.

"Alkenylene" refers to an unsaturated, branched or straight chain hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡CH—).

Unless otherwise indicated, "aryl," by itself of an part of another term, means a substituted or unsubstituted monovalent carbocyclic aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. A substituted carbocyclic aromatic group (e.g., an aryl group) can be substituted with one or more, preferably 1 to 5, of the following groups: —$C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from —H, —$C_1$-$C_8$ alkyl and unsubstituted aryl. In some embodiments, a substituted carbocyclic aromatic group can further include one or more of: —NHC(=NH)$NH_2$, —NHCO$NH_2$, —S(O)$_2$R' and —SR'.

"Substituted alkyl" and "substituted aryl" mean alkyl and aryl, respectively, in which one or more hydrogen atoms are each independently replaced with a substituent. Typical substituents include, but are not limited to, —X, —R, —O—, —OR, —SR, —$S^-$, —$NR_2$, —$NR_3$, =NR, —$CX_3$, —CN, —OCN, —SCN, —N=C=O, —NCS, —NO, —$NO_2$, =$N_2$, —$N_3$, —NRC(=O)R, —C(=O)$NR_2$, —$SO_3^-$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO_3^-$, $PO_3H_2$, —$AsO_2H_2$, —C(=O)R, —C(=O)X, —C(=S)R, —$CO_2$R, —$CO_2^-$, —C(=S)OR, —C(=O)SR, —C(=S) SR, —C(=O)$NR_2$, —C(=S)$NR_2$, or —C(=NR)$NR_2$, where each X is independently a halogen: —F, —Cl, —Br, or —I; and each R is independently —H, —$C_1$-$C_{20}$ alkyl, —$C_6$-$C_{20}$ aryl, —$C_3$-$C_{14}$ heterocycle, a protecting group or a prodrug moiety. Alkylene, alkenylene, and alkynylene groups as described above may also be similarly substituted.

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Unless otherwise noted, the heterocycle is attached to its pendant group at any heteroatom or carbon atom that results in a stable structure.

Representative examples of a $C_3$-$C_8$ heterocycle include, but are not limited to, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be substituted with up to seven groups including, but not limited to, —$C_1$-$C_8$ alkyl, —O—($C_1$-$C_8$ alkyl), aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from —H, —$C_1$-$C_8$ alkyl and aryl. In some embodiments, a substituted heterocycle can also include one or more of —NHC(=NH)$NH_2$, —NHCO$NH_2$, —S(O)$_2$R' and —SR'.

Unless otherwise indicated, "$C_3$-$C_8$ heterocyclo," by itself or as part of another term, refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from —H, —$C_1$-$C_8$ alkyl and aryl. In some embodiments, a substituted heterocyclo can also include one or more of: —NHC(=NH)$NH_2$, —NHCO$NH_2$, —S(O)$_2$R' and —SR'.

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A "$C_3$-$C_8$ carbocycle" group can be unsubstituted or substituted with one or more groups including, but not limited to, —$C_1$-$C_8$ alkyl, —O—($C_1$-$C_8$ alkyl), aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH (R'), —N(R')$_2$ and —CN; where each R' is independently selected from —H, —$C_1$-$C_8$ alkyl and aryl.

Unless otherwise indicated, a "$C_3$-$C_8$ carbocyclo," by itself or as part of another term, refers to a $C_3$-$C_8$ carbocycle group defined above wherein another of the carbocycle groups' hydrogen atoms is replaced with a bond.

Unless otherwise indicated, an "arylene," by itself or as part of another term, is an aryl group which has two covalent bonds and can be in the ortho, meta, or para configurations as shown in the following structures, with phenyl as the exemplary group:

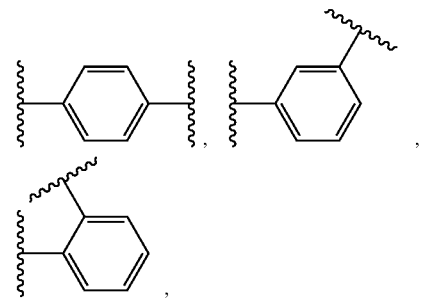

The arylene group can be unsubstituted or substituted with up to four groups including, but not limited to, —$C_1$-$C_8$ alkyl, —O—($C_1$-$C_8$ alkyl), aryl, —C(O)R', —OC(O)R', —C(O) OR', —C(O)$NH_2$, —C(O)NHR', —C(O)N(R')$_2$, —NHC(O) R', —S(O)$_2$R', —S(O)R', —OH, -halogen, —$N_3$, —$NH_2$, —NH(R'), —N(R')$_2$ and —CN; wherein each R' is independently selected from —H, —$C_1$-$C_8$ alkyl and aryl.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$— $CH_2$—O—$CH_3$, —$CH_2$—$CH_2$—NH—$CH_3$, —$CH_2$—

CH$_2$—N(CH$_3$)—CH$_3$, —CH$_2$—CH$_2$—S(O)—CH$_3$, —NH—CH$_2$—CH$_2$—NH—C(O)—CH$_2$—CH$_3$, —CH$_2$—CH$_2$—S(O)$_2$—CH$_3$, —CH═CH—O—CH$_3$, —Si(CH$_3$)$_3$, —CH$_2$—CH═N—O—CH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Unless otherwise indicated, the term "heteroalkylene" by itself or as part of another substituent means a divalent group derived from heteroalkyl (as discussed above), as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, no orientation of the linking group is implied.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., *McGraw-Hill Dictionary of Chemical Terms*, McGraw-Hill Book Company, New York (1984); and Eliel and Wilen, *Stereochemistry of Organic Compounds*, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs$_1$ of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

"Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound (e.g., a Drug, Drug Linker compound, or a Drug Linker Ligand conjugate). The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound of the invention, e.g., a Drug Linker Ligand conjugate or a Drug Linker compound. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: Boc is N-(t-butoxycarbonyl), cit is citrulline, dap is dolaproine, DCM is dichloromethane, DIEA is N,N-diisopropylethylamine, dil is dolaisoleuine, DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, Fmoc is N-(9-fluorenylmethoxycarbonyl), gly is glycine, HATU is O-(7-azabenzotriazol-1-yl)-N,N,N',N'-tetramethyluronium hexafluorophosphate, HBTU is 2-[1H-benzotriazole-1-yl]-1,1,3,3-tetramethylaminium hexafluorophosphate; HOBt is 1-hydroxybenzotriazole, HPLC is high pressure liquid chromatography, ile is isoleucine, lys is lysine, MeOH is methanol, MeVal is N-methyl-valine, PAB is p-aminobenzyl, PBS is phosphate-buffered saline (pH 7.4), Ph is phenyl, phe is L-phenylalanine, PyBrop is bromo tris-pyrrolidino phosphonium hexafluorophosphate, TFA is trifluoroacetic acid, UV is ultraviolet, and val is valine.

The following linker abbreviations are used herein and have the indicated definitions: Val Cit or vc is a valine-citrulline dipeptide site in protease cleavable linker; PABC is p-aminobenzylcarbamoyl; (Me)vc is N-methyl-valine citrulline, where the linker peptide bond has been modified to prevent its cleavage by cathepsin B; and MC(PEG)$_6$-OH is maleimidocaproyl-polyethylene glycol.

The following cytotoxic drug abbreviations are used herein and have the indicated definitions: "Auristatin F" or "AF" is N,N-dimethylvaline-valine-dolaisoleuine(dil)-dolaproine (dap)-phenylalanine. "MMAF" is N-methylvaline-valine-dolaisoleuine(dil)-dolaproine(dap)-phenylalanine (MW 731.5).

Compounds and Conjugates

As noted in the Summary of the Invention, the present invention is drawn to a series of compounds and conjugates containing a Drug moiety (D) linked via its C terminus to a Linker unit. The Linker unit can operate to provide a suitable release of D.

In one group of embodiments, the invention provides Drug Linker compounds having Formula I:

LU-D    (I)

or a pharmaceutically acceptable salt or solvate thereof wherein D has the formula:

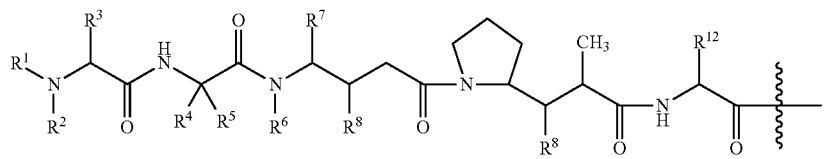

wherein the wavy line indicates the attachment to a Linker unit (LU);

$R^1$ and $R^2$ each is independently selected from the group consisting of —H and —$C_1$-$C_8$ alkyl, with the proviso that both $R^1$ and $R^2$ are not —H;

$R^3$ is selected from the group consisting of —H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);

$R^4$ is selected from the group consisting of —H, —$C_1$-$C_8$ alkyl, —$C_3$-$C_8$ carbocycle, aryl, —$X^1$-aryl, —$C_1$-$C_8$ alkyl-($C_3$-$C_8$ carbocycle), —$C_3$-$C_8$ heterocycle and —$X^1$—($C_3$-$C_8$ heterocycle);

$R^5$ is selected from the group consisting of —H and methyl;

or $R^4$ and $R^5$ jointly form a carbocyclic ring and have the formula —$(CR^aR^b)_n$— wherein $R^a$ and $R^b$ are independently selected from the group consisting of —H and —$C_1$-$C_8$ alkyl and n is selected from the group consisting of 2, 3, 4, 5 and 6;

$R^6$ is selected from the group consisting of —H and —$C_1$-$C_8$ alkyl;

$R^7$ is selected from the group consisting of —H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);

each $R^8$ is independently selected from the group consisting of —H, —OH, —$C_1$-$C_8$ alkyl, —$C_3$-$C_8$ carbocycle and —O—($C_1$-$C_8$ alkyl);

each $X^1$ is independently —$C_1$-$C_{10}$ alkylene-; and $R^{12}$ is selected from the group consisting of —H, —$C_1$-$C_8$ alkyl, aryl, —$X^1$-aryl, —$C_3$-$C_8$ carbocycle, —$X^1$—($C_3$-$C_8$ heterocycle), —$C_1$-$C_8$ alkylene-$NH_2$, —$C_3$-$C_8$ heterocycle and —$X^1$—($C_3$-$C_8$ heterocycle);

or a pharmaceutically acceptable salt or solvate thereof.

In some embodiments, $R^{12}$ is selected from the group consisting of side chains of natural and non-natural amino acids.

In some embodiments, $R^{12}$ is selected from the group consisting of H, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

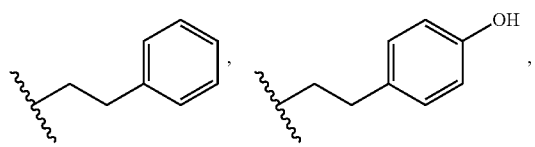

-continued

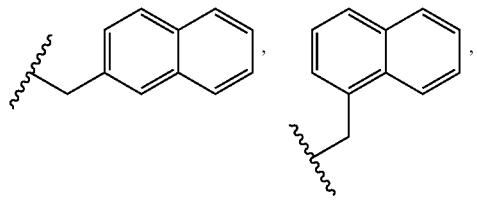

-continued

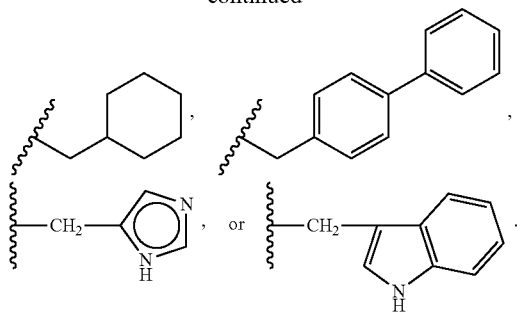

In some embodiments, $R^{12}$ is selected from the group consisting of side chains of natural amino acids. In some embodiments, $R^{12}$ is the side chain of phenylalanine. In some embodiments, $R^{12}$ is the side chain of methionine. In some embodiments, $R^{12}$ is the side chain of tryptophan.

In another group of embodiments, the invention provides Drug Linker compounds having Formula I:

LU-D    (I)

or a pharmaceutically acceptable salt or solvate thereof; wherein D has the formula:

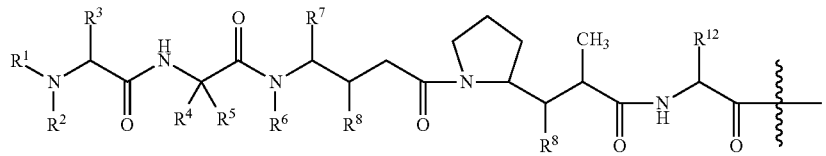

wherein the wavy line indicates the attachment to a Linker unit (LU);

$R^1$ and $R^2$ each is independently selected from the group consisting of —H and —$C_1$-$C_8$ alkyl, with the proviso that both $R^1$ and $R^2$ are not —H;

$R^3$ is selected from the group consisting of —H, —$C_1$-$C_8$ alkyl, —$C_3$-$C_8$ carbocycle, aryl, —$C_1$-$C_8$ alkyl-aryl, —$X^1$—($C_3$-$C_8$ carbocycle), —$C_3$-$C_8$ heterocycle and —$X^1$—($C_3$-$C_8$ heterocycle);

$R^4$ is selected from the group consisting of —H, —$C_1$-$C_8$ alkyl, —$C_3$-$C_8$ carbocycle, aryl, —$X^1$-aryl, —$C_1$-$C_8$ alkyl-($C_3$-$C_8$ carbocycle), —$C_3$-$C_8$ heterocycle and —$X^1$—($C_3$-$C_8$ heterocycle);

$R^5$ is selected from the group consisting of —H and methyl;

or $R^4$ and $R^5$ jointly form a carbocyclic ring and have the formula —$(CR^aR^b)_n$— wherein $R^a$ and $R^b$ are independently selected from the group consisting of —H and —$C_1$-$C_8$ alkyl and n is selected from the group consisting of 2, 3, 4, 5 and 6;

$R^6$ is selected from the group consisting of —H and —$C_1$-$C_8$ alkyl;

$R^7$ is selected from the group consisting of —H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);

each $R^8$ is independently selected from the group consisting of —H, —OH, —$C_1$-$C_8$ alkyl, —$C_3$-$C_8$ carbocycle and —O—($C_1$-$C_8$ alkyl);

$R^{12}$ is selected from the group consisting of —H, —$C_1$-$C_8$ alkyl, aryl, —$X^1$-aryl, —$C_3$-$C_8$ carbocycle, —$X^1$—($C_3$-$C_8$ heterocycle), —$C_1$-$C_8$ alkylene-$NH_2$, —$C_3$-$C_8$ heterocycle and —$X^1$—($C_3$-$C_8$ heterocycle); and each $X^1$ is independently —$C_1$-$C_{10}$ alkylene-;

the moiety LU— is a Linker unit having the formula —$W_w$-$A_a$;

$W_w$ is a sequence of w independently selected amino acid diradicals;

w is an integer ranging from 1 to 12;

A is a Stretcher unit, and a is 1 or 2;

or a pharmaceutically acceptable salt or solvate thereof.

In some embodiments, $R^{12}$ is a side chain of a natural amino acid. In some embodiments, $R^{12}$ is the side chain of phenylalanine. In some embodiments, $R^{12}$ is the side chain of methionine. In some embodiments, $R^{12}$ is the side chain of tryptophan.

In some embodiments, the Stretcher unit A is —NH—$R^9$—$R^{11}$ or —O—$R^9$—$R^{11}$, wherein —$R^9$—$R^{11}$ has the formula:

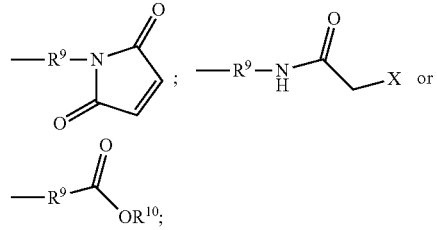

wherein $R^9$ can be selected from the group consisting of —$C_1$-$C_{10}$ alkylene-, —$C_3$-$C_8$ carbocyclo-, -arylene-, —$C_1$-$C_{30}$ heteroalkylene-, —$C_3$-$C_8$ heterocyclo-, —$C_1$-$C_{10}$ alkylene-arylene-, -arylene-$C_1$-$C_{10}$ alkylene-, —$C_1$-$C_{10}$ alkylene-($C_3$-$C_8$carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, and —($C_3$-$C_8$ heterocyclo)-$C_1$-$C_{10}$ alkylene-;

wherein X is a leaving group; and each $R^{10}$ forms an activated ester, wherein $R^{10}$ is independently selected from the group consisting of H, —$C_1$-$C_{10}$ alkyl, —$C_3$-$C_8$ carbocycle, -aryl, —$C_1$-$C_{30}$ heteroalkyl, —$C_3$-$C_8$ heterocyclo, —$C_1$-$C_{10}$ alkylene-aryl, -arylene-$C_1$-$C_{10}$ alkyl, —$C_1$-$C_{10}$ alkylene-($C_3$-$C_8$ carbocyclo), —($C_3$-$C_8$ carbocyclo)-$C_1$-$C_{10}$ alkyl, —$C_1$-$C_{10}$ alkylene-($C_3$-$C_8$ heterocyclo), and —($C_3$-$C_8$ heterocyclo)-$C_1$-$C_{10}$ alkyl.

In some embodiments of the Stretcher unit A, —NH—$R^9$— is selected from —NH—$C_1$-$C_{10}$ alkylene-, —NH—$C_1$-$C_{10}$ alkylene-NH—C(O)—$C_1$-$C_{10}$ alkylene-, —NH—$C_1$-$C_{10}$ alkylene-C(O)—NH—$C_1$-$C_{10}$ alkylene-, —NH—

—(CH$_2$CH$_2$O)$_r$—, —NH—(CH$_2$CH$_2$O)$_r$—CH$_2$—, —NH—(CH$_2$CH$_2$NH)$_r$—(CH$_2$)$_r$—, —NH—(CH$_2$CH$_2$NH)$_r$—(CH$_2$)$_r$—NH—C(O)—(CH$_2$)$_r$—, —NH—(C$_3$-C$_8$ carbocyclo)-, —NH-(arylene-)-, and —NH—(C$_3$-C$_8$ heterocyclo-)-, wherein each r is independently 1-10.

In some embodiments of the Stretcher unit A, —O—R$^9$— is selected from —O—C$_1$-C$_{10}$ alkylene-, —O—C$_1$-C$_{10}$ alkylene-NH—C(O)—C$_1$-C$_{10}$ alkylene-, —O—C$_1$-C$_{10}$ alkylene-C(O)—NH—C$_1$-C$_{10}$ alkylene-, —O—(CH$_2$CH$_2$O)$_r$—, O—(CH$_2$CH$_2$O)$_r$—CH$_2$—, —O—(C$_3$-C$_8$ carbocyclo)-, —O-(arylene)-, and —O—(C$_3$-C$_8$ heterocyclo-)-, wherein each r is independently 1-10.

In embodiments in which the Stretcher unit A is —O—R$^9$—R$^{11}$—, the ester is a hindered ester.

In some embodiments, R$^9$ is a polyamine.

In some embodiments, D has the formula

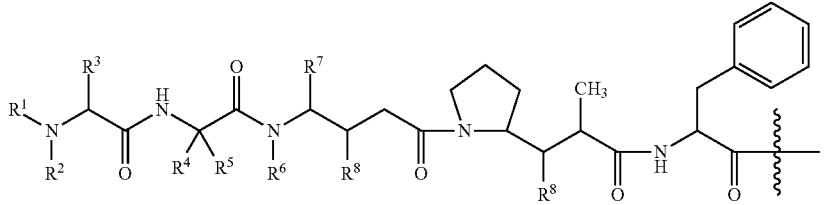

wherein R$^1$-R$^8$ are as set forth above.

In a related aspect, the present invention provides Drug Linker Ligand conjugates in which the Drug Linker compounds further comprise a Ligand unit (L), the conjugates having the formula (II):

L-(LU-D)$_p$     (II)

or a pharmaceutically acceptable salt or solvate thereof; wherein D has the formula:

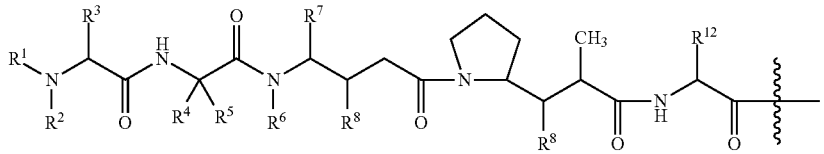

wherein the wavy line indicates the attachment to a Linker Unit (LU);

R$^1$ and R$^2$ is independently selected from the group consisting of —H and —C$_1$-C$_8$ alkyl, with the proviso that both R$^1$ and R$^2$ are not —H;

R$^3$ is selected from the group consisting of —H, —C$_1$-C$_8$ alkyl, —C$_3$-C$_8$ carbocycle, aryl, —C$_1$-C$_8$ alkyl-aryl, —X$^1$—(C$_3$-C$_8$ carbocycle), —C$_3$-C$_8$ heterocycle and —X$^1$—(C$_3$-C$_8$ heterocycle);

R$^4$ is selected from the group consisting of —H, —C$_1$-C$_8$ alkyl, —C$_3$-C$_8$ carbocycle, aryl, —C$_1$-C$_8$ alkyl-(C$_3$-C$_8$ carbocycle), —C$_3$-C$_8$ heterocycle and —X$^1$—(C$_3$-C$_8$ heterocycle);

R$^5$ is selected from the group consisting of —H and methyl;

or R$^4$ and R$^5$ jointly form a carbocyclic ring and have the formula —(CR$^a$R$^b$)$_n$— wherein R$^a$ and R$^b$ are independently selected from the group consisting of —H and —C$_1$-C$_8$ alkyl and n is selected from the group consisting of 2, 3, 4, 5 and 6;

R$^6$ is selected from the group consisting of —H and —C$_1$-C$_8$ alkyl;

R$^7$ is selected from the group consisting of —H, —C$_1$-C$_8$ alkyl, —C$_3$-C$_8$ carbocycle, aryl, —X$^1$—(C$_3$-C$_8$ carbocycle), —C$_3$-C$_8$ heterocycle and —X$^1$—(C$_3$-C$_8$ heterocycle);

each R$^8$ is independently selected from the group consisting of —H, —OH, —C$_1$-C$_8$ alkyl, —C$_3$-C$_8$ carbocycle and —O—(C$_1$-C$_8$ alkyl);

each X$^1$ is independently —C$_1$-C$_{10}$ alkylene-;

R$^{12}$ is selected from the group consisting of —H, —C$_1$-C$_8$ alkyl, aryl, —X$^1$-aryl, —C$_3$-C$_8$ carbocycle, —X$^1$—(C$_3$-C$_8$ heterocycle), —C$_1$-C$_8$ alkylene-NH$_2$, —C$_3$-C$_8$ heterocycle and —X$^1$—(C$_3$-C$_8$ heterocycle);

the moiety LU— is a Linker unit having the formula —W$_w$-A$_a$-;

W$_w$ is a sequence of w independently selected amino acid diradicals;

w is an integer ranging from 1 to 12;

A is a Stretcher unit a is 1 or 2; and p is an integer of from 1 to 20;

or a pharmaceutically acceptable salt or solvate thereof.

In some embodiments, the Stretcher unit A is —NH—R$^9$—R$^{11}$ or —O—R$^9$—R$^{11}$, wherein —R$^9$—R$^{11}$ has the formula:

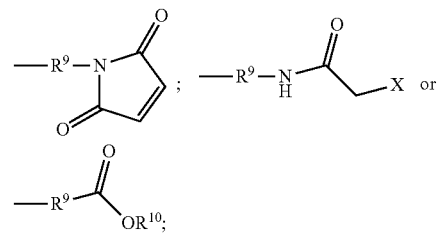

wherein R$^9$ can be selected from the group consisting of —C$_1$-C$_{10}$alkylene-, —C$_3$-C$_8$carbocyclo-, -arylene-, —C$_1$-C$_{30}$heteroalkylene-, —C$_3$-C$_8$heterocyclo-, —C$_1$-C$_{10}$alkylene-arylene-, -arylene-C$_1$-C$_{10}$alkylene-, —C$_1$-C$_{10}$alkylene-(C$_3$-C$_8$ carbocyclo)-, —(C$_3$-C$_8$ carbocyclo)-C$_1$-C$_{10}$ alkylene-, —C$_1$-C$_{10}$ alkylene-(C$_3$-C$_8$ heterocyclo)-, and —(C$_3$-C$_8$ heterocyclo)-C$_1$-C$_{10}$ alkylene-;

wherein X is a leaving group; and each $R^{10}$ forms an activated ester, wherein $R^{10}$ is independently selected from the group consisting of —H, —$C_1$-$C_{10}$ alkyl, —$C_3$-$C_8$ carbocycle, aryl, —$C_1$-$C_{10}$ heteroalkyl, —$C_3$-$C_8$ heterocyclo, —$C_1$-$C_{10}$ alkylene-aryl, -arylene-$C_1$-$C_{10}$ alkyl, —$C_1$-$C_{10}$ alkylene-($C_3$-$C_8$ carbocyclo), —($C_3$-$C_8$ carbocyclo)-$C_1$-$C_{10}$ alkyl, —$C_1$-$C_{10}$ alkylene-($C_3$-$C_8$ heterocyclo), and —($C_3$-$C_8$ heterocyclo)-$C_1$-$C_{10}$ alkyl.

In some embodiments of the Stretcher unit A, —NH—$R^9$— is selected from —NH—$C_1$-$C_{10}$ alkylene-, —NH—$C_1$-$C_{10}$ alkylene-NH—C(O)—$C_1$-$C_{10}$ alkylene-, —NH—$C_1$-$C_{10}$ alkylene-C(O)—NH—$C_1$-$C_{10}$ alkylene-, —NH—(CH$_2$CH$_2$O)$_r$—, —NH—(CH$_2$CH$_2$O)$_r$—CH$_2$—, —NH—(CH$_2$CH$_2$NH)$_r$—(CH$_2$)$_r$—, —NH—(CH$_2$CH$_2$NH)$_r$—(CH$_2$)$_r$—NH—C(O)—(CH$_2$)$_r$—, —NH—($C_3$-$C_8$ carbocyclo)-, —NH-(arylene-)-, and —NH—($C_3$-$C_8$ heterocyclo-)-, wherein each r is independently 1-10.

In some embodiments of the Stretcher unit A, —O—$R^9$— is selected from —O—$C_1$-$C_{10}$ alkylene-, —O—$C_1$-$C_{10}$ alkylene-NH—C(O)—$C_1$-$C_{10}$ alkylene-, —O—$C_1$-$C_{10}$ alkylene-C(O)—NH—$C_1$-$C_{10}$ alkylene-, —O—(CH$_2$CH$_2$O)$_r$—, O—(CH$_2$CH$_2$O)$_r$—CH$_2$—, —O—($C_3$-$C_8$ carbocyclo)-, —O-(arylene)-, and —O—($C_3$-$C_8$ heterocyclo-)-, wherein each r is independently 1-10.

In embodiments in which the Stretcher unit A is —O—$R^9$—$R^{11}$—, the ester is a hindered ester.

In some embodiments of formula I or II, D has the formula

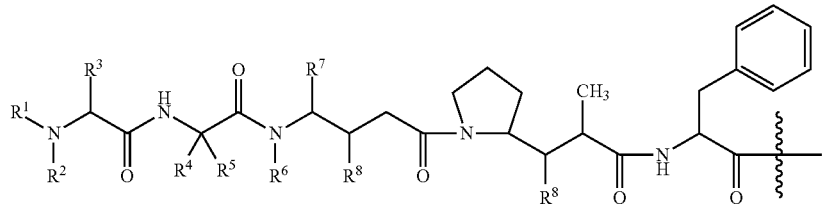

or a pharmaceutically acceptable salt or solvate thereof, wherein $R^1$-$R^8$ are as set forth herein.

Drug Linker Ligand conjugates and Drug Linker compounds also include those wherein D has the formula:

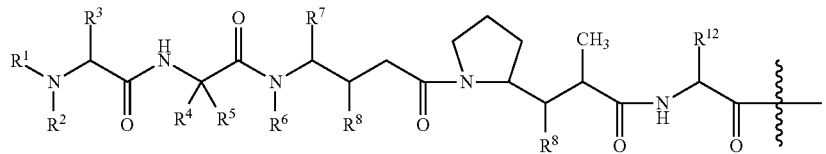

when conjugated; and, as a free drug, D has the formula:

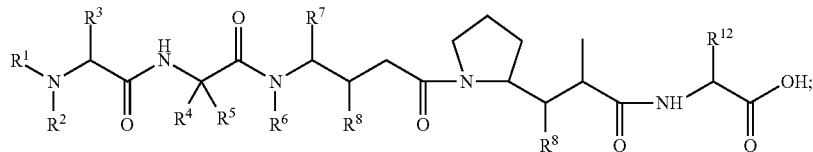

or a pharmaceutically acceptable salt of solvate thereof, wherein for both formulas:

(a) $R^1$ and $R^2$ are independently selected from the group consisting of —H and —$C_1$-$C_8$ alkyl, with the proviso that both $R^1$ and $R^2$ are not —H;
(b) $R^1$ and $R^2$ are independently selected from the group consisting of —H and —$C_1$-$C_8$ unsubstituted alkyl, with the proviso that both $R^1$ and $R^2$ are not —H;
(c) $R^1$ and $R^2$ are independently selected from the group consisting of —H and methyl with the proviso that both $R^1$ and $R^2$ are not —H;
(d) $R^3$ is selected from the group consisting of —H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);
(e) $R^3$ is selected from the group consisting of —H or —$C_1$-$C_8$ alkyl;
(f) $R^3$ is selected from the group consisting of —H or unsubstituted —$C_1$-$C_8$ alkyl;
(g) $R^3$ is selected from the group consisting of —H or isopropyl;
(h) $R^4$ is selected from the group consisting of —H, —$C_1$-$C_8$ alkyl, —$C_3$-$C_8$ carbocycle, aryl, —$X^1$-aryl, —$C_1$-$C_8$ alkyl-($C_3$-$C_8$ carbocycle), —$C_3$-$C_8$ heterocycle and —$X^1$—($C_3$-$C_8$ heterocycle);
(i) $R^4$ is a side chain of a natural amino acid;
(j) $R^4$ is —H, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NH-CHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

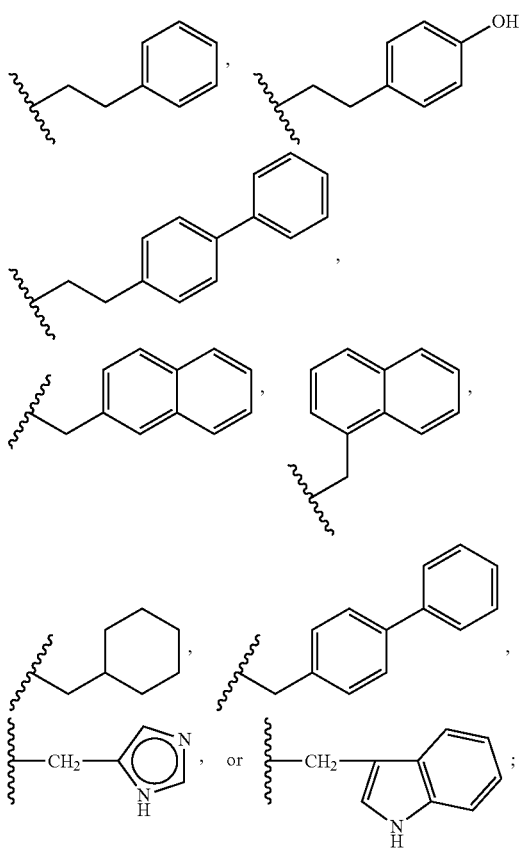

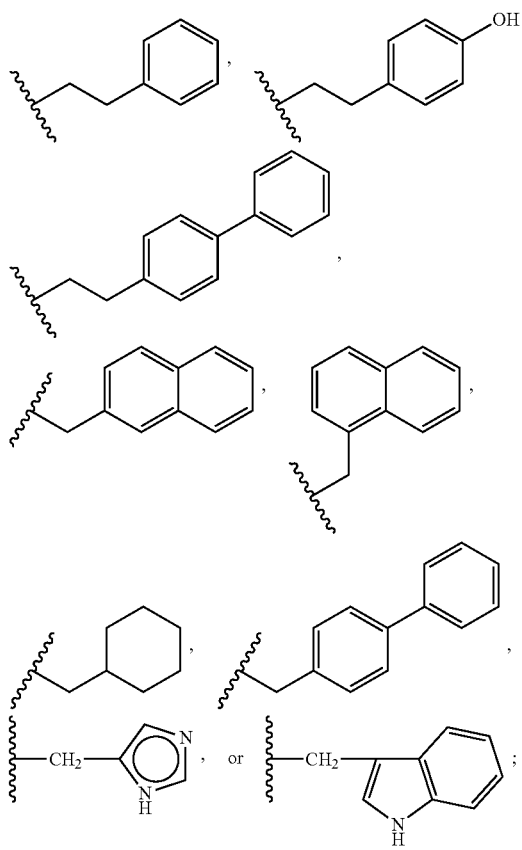

(k) $R^4$ is isopropyl and $R^5$ is —H;

(l) or $R^4$ and $R^5$ jointly form a carbocyclic ring and have the formula —$(CR^aR^b)_n$— wherein $R^a$ and $R^b$ are independently selected from the group consisting of —H and —$C_1$-$C_8$ alkyl and n is selected from the group consisting of 2, 3, 4, 5 and 6;

(m) $R^6$ is selected from the group consisting of —H and —$C_1$-$C_8$ alkyl;

(n) $R^6$ is selected from the group consisting of —H and unsubstituted —$C_1$-$C_8$ alkyl;

(o) $R^6$ is selected from the group consisting of —H and methyl;

(p) $R^7$ is selected from the group consisting of —H, —$C_1$-$C_8$ alkyl, —$C_3$-$C_8$ carbocycle, aryl, —$X^1$-aryl, —$X^1$—($C_3$-$C_8$ carbocycle), —$C_3$-$C_8$ heterocycle and —$X^1$—($C_3$-$C_8$ heterocycle);

(q) $R^7$ is selected from the group consisting of —H and —$C_1$-$C_8$ alkyl;

(r) $R^7$ is selected from the group consisting of —H and unsubstituted —$C_1$-$C_8$ alkyl;

(s) $R^7$ is selected from the group consisting of —H and sec-butyl;

(t) each $R^8$ is independently selected from the group consisting of —H, —OH, —$C_1$-$C_8$ alkyl, —$C_3$-$C_8$ carbocycle and —O—($C_1$-$C_8$ alkyl);

(u) each $R^8$ is independently selected from the group consisting of —H and —O—($C_1$-$C_8$ alkyl);

(v) each $R^8$ is independently selected from the group consisting of —H and unsubstituted —O—($C_1$-$C_8$ alkyl);

(w) each $R^s$ is independently selected from the group consisting of —H and unsubstituted —$OCH_3$;

(x) each $X^1$ is independently —$C_1$-$C_{10}$ alkylene-;

(y) each $X^1$ is independently unsubstituted —$C_1$-$C_{10}$ alkylene-;

(z) $R^{12}$ is selected from the group consisting of —H, —$C_1$-$C_8$ alkyl, aryl, —$X^1$aryl, —$C_3$-$C_8$ carbocycle, —$X^1$—($C_3$-$C_8$ heterocycle), —$C_1$-$C_8$ alkylene-$NH_2$, —$C_3$-$C_8$ heterocycle and —$X^1$—($C_3$-$C_8$ heterocycle);

(aa) $R^{12}$ is a side chain of a natural amino acid;

(bb) $R^{12}$ is H, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pridylmethyl-, 4-pyridylmethyl-, phenyl, cyclohexyl, and any combination of embodiments (a) to (bb), provided that it is understood that combinations in which different embodiments of the same substituent would be combined are excluded. In an exemplary embodiment, the alkyl groups in groups (a) to (bb) are unsaturated.

In exemplary embodiments, $R^5$ is —H, and $R^4$ and $R^{12}$ are independently a side chain of a natural amino acid and the remaining groups are as indicated in any of the embodiments herein.

In exemplary embodiments, $R^3$ is —H or —$C_1$-$C_8$ alkyl, $R^4$ is a side chain of a natural amino acid, $R^7$ is —H or —$C_1$-$C_8$ alkyl, and $R^8$ is —O—($C_1$-$C_8$ alkyl) and the remaining groups are as indicated in any of the embodiments herein.

In exemplary embodiments, $R^3$ is —H or —$C_1$-$C_8$ alkyl, $R^4$ is —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —(CH$_2$)$_3$ NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, R$^7$ is —H or —C$_1$-C$_8$ alkyl, and R$^8$ is —O—(C$_1$-C$_8$ alkyl) and the remaining groups are as indicated in any of the embodiments herein.

In exemplary embodiments, R$^3$ is —H or —C$_1$-C$_8$ alkyl, R$^4$ is —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, R$^7$ is —H or —C$_1$-C$_8$ alkyl, R$^8$ is —O—(C$_1$-C$_8$ alkyl), R$^{12}$ is a side chain of a natural amino acid, and the remaining groups are as indicated in any of the embodiments herein.

In exemplary embodiments, R$^3$ is —H or —C$_1$-C$_8$ alkyl, R$^4$ is —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$ NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, R$^7$ is —H or —C$_1$-C$_8$ alkyl, R$^8$ is —O—(C$_1$-C$_8$ alkyl), R$^{12}$ is the side chain of phenylalanine, methionine or tryptophan, and the remaining groups are as indicated in any of the embodiments herein.

In exemplary embodiments, R$^3$ is —H or —C$_1$-C$_8$ alkyl, R$^4$ is —CH$_2$CH$_2$SCH$_3$ or —CH$_2$CH(CH$_3$)CH$_3$, R$^7$ is —H or —C$_1$-C$_8$ alkyl, and R$^8$ is —O—(C$_1$-C$_8$ alkyl) and the remaining groups are as indicated in any of the embodiments herein.

In exemplary embodiments, R$^3$ is —H or —C$_1$-C$_8$ alkyl, R$^4$ is —CH$_2$CH$_2$SCH$_3$ or —CH$_2$CH(CH$_3$)CH$_3$, R$^7$ is —H or —C$_1$-C$_8$ alkyl, R$^8$ is —O—(C$_1$-C$_8$ alkyl), R$^{12}$ is a side chain of a natural amino acid, and the remaining groups are as indicated in any of the embodiments herein.

In exemplary embodiments, R$^3$ is —H or —C$_1$-C$_8$ alkyl, R$^4$ is —CH$_2$CH$_2$SCH$_3$ or —CH$_2$CH(CH$_3$)CH$_3$, R$^7$ is —H or —C$_1$-C$_8$ alkyl, R$^8$ is —O—(C$_1$-C$_8$ alkyl), R$^{12}$ is the side chain of phenylalanine, methionine or tryptophan, and the remaining groups are as indicated in any of the embodiments herein.

In exemplary embodiments, R$^3$ is —H or —C$_1$-C$_8$ saturated alkyl, R$^4$ is a side chain of a natural amino acid, R$^6$ is —H or —C$_1$-C$_8$ saturated alkyl; R$^7$ is —H or C$_1$-C$_8$ saturated alkyl, and R$^8$ is —O—(C$_1$-C$_8$ saturated alkyl) and the remaining groups are as indicated in any of the embodiments herein.

In exemplary embodiments, R$^3$ is —H or —C$_1$-C$_8$ unsubstituted saturated alkyl, R$^4$ is a side chain of a natural amino acid, R$^6$ is —H or —C$_1$-C$_8$ unsubstituted saturated alkyl, R$^7$ is —H or —C$_1$-C$_8$ unsubstituted saturated alkyl, and R$^8$ is —O—(C$_1$-C$_8$ unsubstituted saturated alkyl) and the remaining groups are as indicated in any of the embodiments herein.

In exemplary embodiments, R$^1$ and R$^2$ are —H or —C$_1$-C$_8$ unsubstituted saturated alkyl with the proviso that both are not hydrogen, R$^3$ is —H or —C$_1$-C$_8$ unsubstituted saturated alkyl, R$^4$ is a side chain of a natural amino acid, R$^6$ is —H or —C$_1$-C$_8$ unsubstituted saturated alkyl, R$^7$ is —H or —C$_1$-C$_8$ unsubstituted saturated alkyl, and R$^8$ is —O—(C$_1$-C$_8$ unsubstituted saturated alkyl) and the remaining groups are as indicated in any of the embodiments herein.

In exemplary embodiments, R$^1$ and R$^2$ are —H or —C$_1$-C$_8$ unsubstituted saturated alkyl with the proviso that both are not hydrogen, R$^3$ is —H or —C$_1$-C$_8$ unsubstituted saturated alkyl, R$^4$ is a side chain of a natural amino acid, R$^6$ is —H or —C$_1$-C$_8$ unsubstituted saturated alkyl, R$^7$ is —H or —C$_1$-C$_8$ unsubstituted saturated alkyl, R$^8$ is —O—(C$_1$-C$_8$ unsubstituted saturated alkyl); R$^{12}$ is a side chain of a natural amino acid and the remaining groups are as indicated in any of the embodiments herein.

In exemplary embodiments, R$^1$ and R$^2$ are —H or —C$_1$-C$_8$ unsubstituted saturated alkyl with the proviso that both are not hydrogen, R$^3$ is —H or —C$_1$-C$_8$ unsubstituted saturated alkyl, R$^4$ is —CH$_2$CH$_2$SCH$_3$ or —CH$_2$CH(CH$_3$)CH$_3$, R$^6$ is —H or —C$_1$-C$_8$ unsubstituted saturated alkyl, R$^7$ is —H or —C$_1$-C$_8$ unsubstituted saturated alkyl, R$^8$ is —O—(C$_1$-C$_8$ unsubstituted saturated alkyl); R$^{12}$ is the side chain of phenylalanine, methionine or tryptophan and the remaining groups are as indicated in any of the embodiments herein.

In exemplary embodiments, R$^1$ and R$^2$ are —H or —C$_1$-C$_3$ unsubstituted saturated alkyl with the proviso that both are not hydrogen, R$^3$ is —C$_1$-C$_4$ unsubstituted saturated alkyl, R$^4$ is —CH$_2$CH$_2$SCH$_3$ or —CH$_2$CH(CH$_3$)CH$_3$, R$^5$ is —H, R$^6$ is methyl, R$^7$ is or —C$_1$-C$_4$ unsubstituted saturated alkyl, R$^8$ is —O—(C$_1$-C$_3$ unsubstituted saturated alkyl); R$^{12}$ is the side chain of phenylalanine, methionine or tryptophan and the remaining groups are as indicated in any of the embodiments herein.

In some embodiments, R$^3$, R$^4$ and R$^7$ are independently isopropyl or sec-butyl and R$^5$ is —H. In an exemplary embodiment, R$^3$ and R$^4$ are each isopropyl, R$^5$ is —H, and R$^7$ is sec-butyl.

In some embodiments, R$^2$ and R$^6$ are each —H or —C$_1$-C$_8$alkyl. In another embodiment, R$^2$ and R$^6$ are each —CH$_3$, and R$^5$ is —H.

In some embodiments, each occurrence of R$^8$ is —OCH$_3$.

In an exemplary embodiment, R$^3$ and R$^4$ are each isopropyl, R$^2$ and R$^6$ are each methyl, R$^5$ is —H, R$^7$ is sec-butyl, and each occurrence of R$^8$ is —OCH$_3$.

In another aspect of the invention the compound D has the following formula:

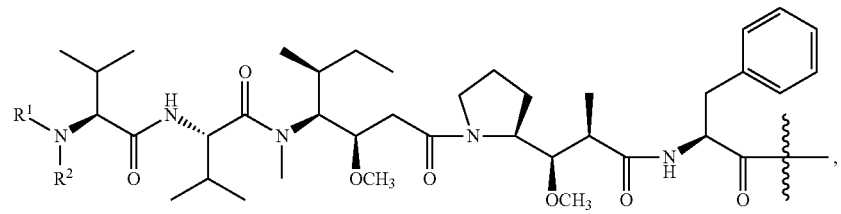

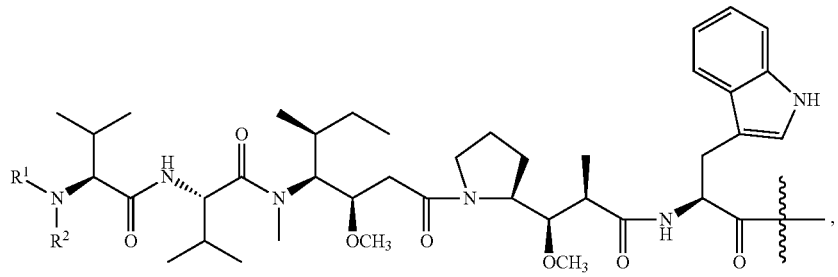
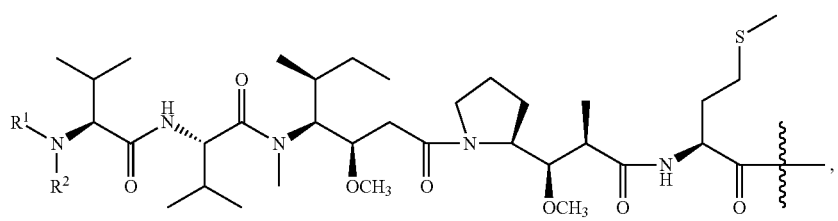
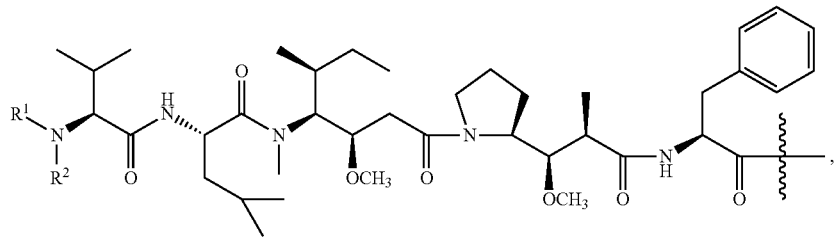
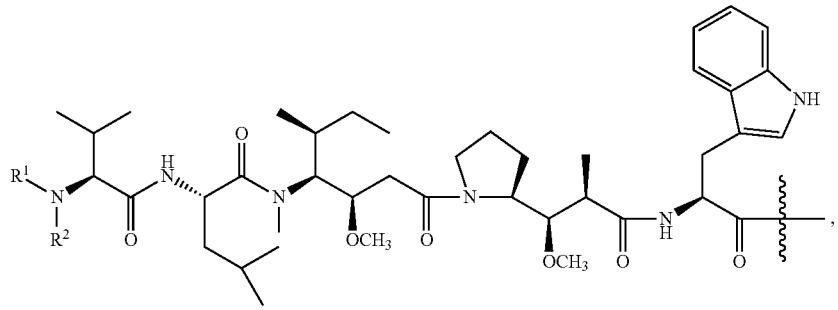
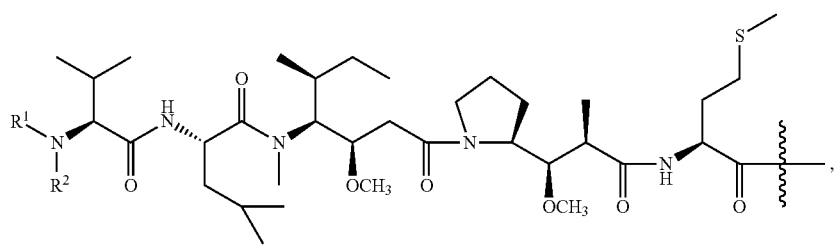
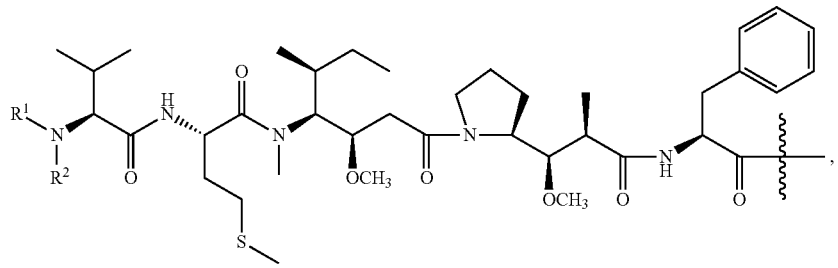

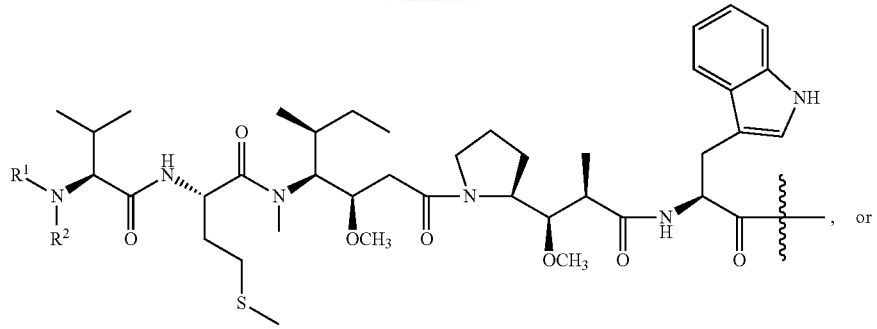
, or
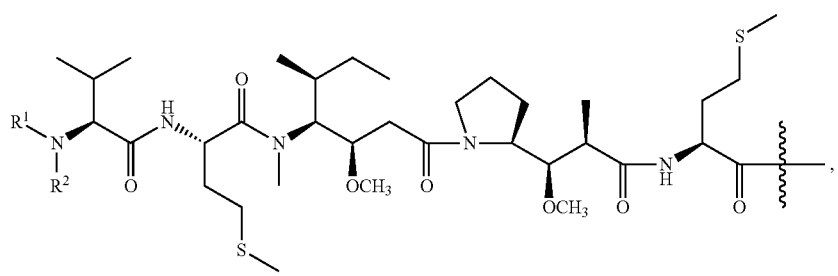
,
or a pharmaceutically acceptable salt or solvate thereof, wherein the wavy line indicates a covalent bond to the Linker unit (LU).
In another aspect of the invention the compound D has one of the following formulas as a free drug:
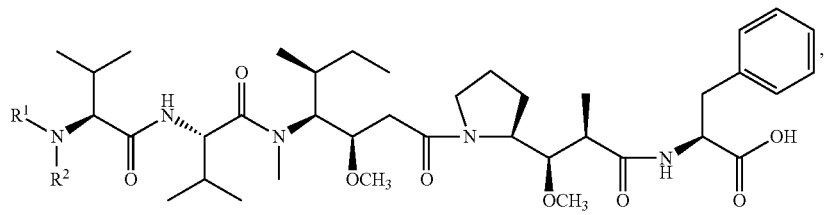
,
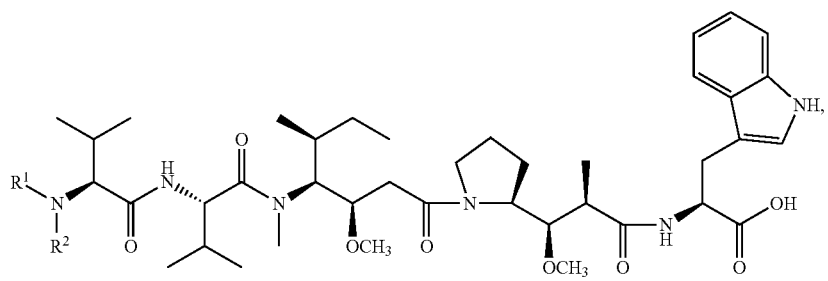
,
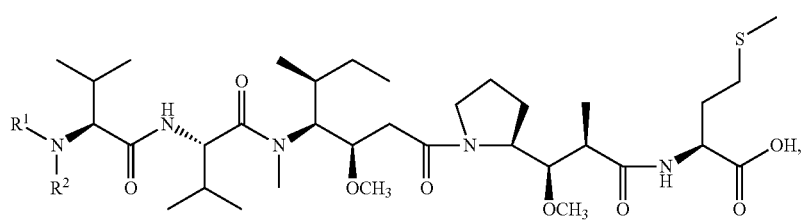

-continued
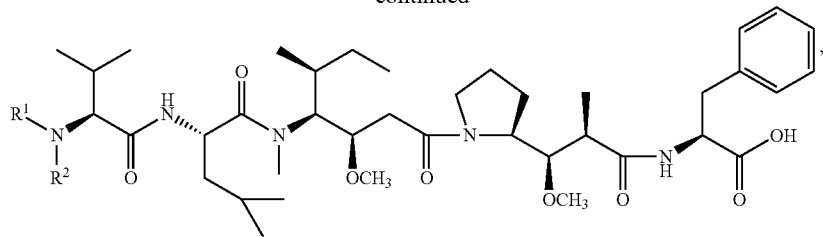
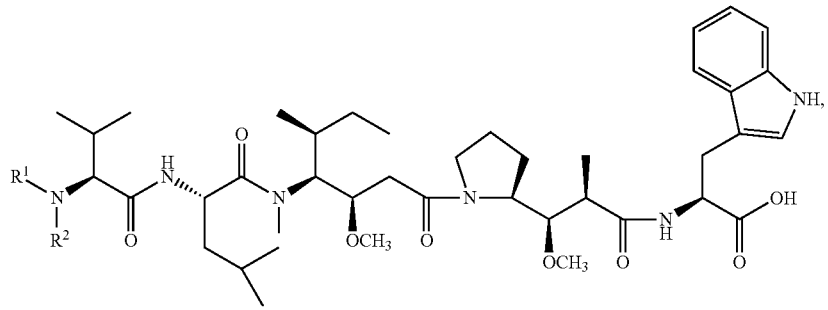
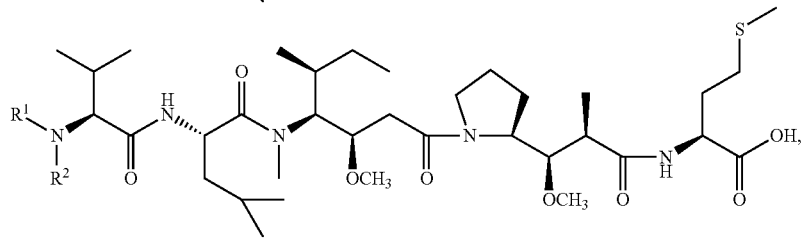
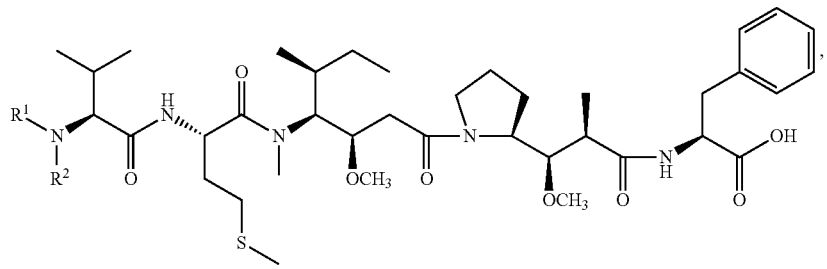
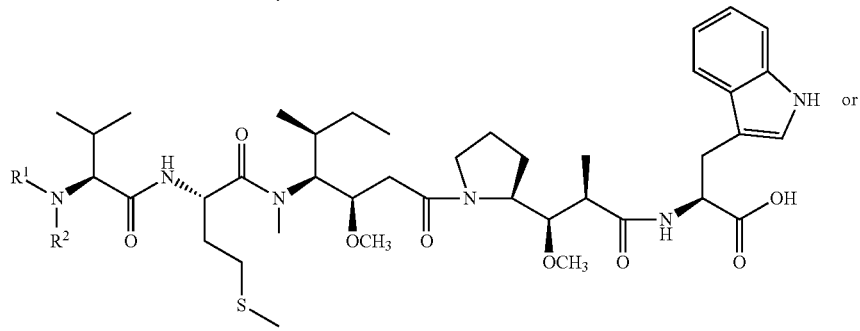
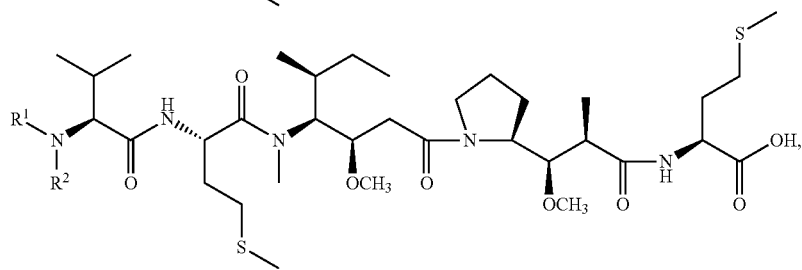
or a pharmaceutically acceptable salt or solvate thereof.

Within the above embodiments, each of $R^1$ and $R^2$ is —H or —$C_{1-8}$ alkyl, with the proviso that both $R^1$ and $R^2$ are not —H. In another group of embodiments, each of $R^1$ and $R^2$ is —$CH_3$.

In still another embodiment, D has the formula:

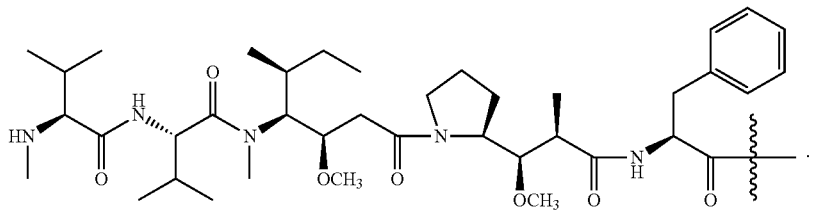 [SMILES: *C(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@@H](NC)C(C)C)C(C)C]

In yet another aspect, Drug Linker Ligand conjugates are provided in which the Ligand is an antibody (e.g., an intact antibody or antibody fragment). In this aspect, the conjugates are represented by Formula IIa:

or pharmaceutically acceptable salts or solvates thereof, wherein Ab is an antibody, A is a Stretcher unit, a is 1 or 2, each W is independently an Amino Acid unit, w is an integer ranging from 1 to 12, p is an integer of from 1 to about 20, and D is a Drug moiety of the embodiments above.

Exemplary embodiments of Formula IIa' have the following structures:

Returning to Formula IIa', the conjugates comprise an antibody covalently attached to one or more Drug units (moieties) via a Linker unit: A, a, W and w are as described above. The antibody drug conjugate include pharmaceutically acceptable salts or solvates thereof.

The drug loading is represented by p, the average number of Drugs units per antibody in a molecule of Formula II. Drug loading may range from 1 to 20 drugs (D) per antibody (Ab or mAb). Compositions of the ADC of Formula IIa' include mixtures of antibodies conjugated with a range of drugs, from 1 to 20. In some embodiments, p is from about 1 to about 8 Drug units per antibody. In some embodiments, p is 1. In some embodiments, p is from about 2 to about 8 Drug units per antibody. In some embodiments, p is from about 2 to about 6, 2 to about 5, or 2 to about 4 Drug units per antibody. In some embodiments, p is about 2, about 4, about 6 or about 8 Drug units per antibody.

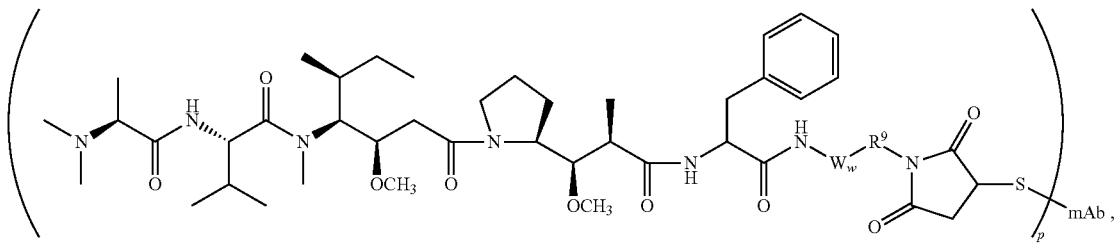

wherein the NH adjacent $W_w$ is an amino group of a W.

The drug loading is represented by p, the average number of drug molecules per ligand (e.g., an antibody) (e.g. of Formula II, IIa, IIa'). Drug loading may range from 1 to 20 Drug units (D) per Ligand unit (e.g., Ab or in Ab). Compositions of Formula IIa and Formula IIa' include mixtures of antibodies conjugated with a range of drugs, from 1 to 20.

In some embodiments, p is from about 1 to about 8 Drug units per Ligand unit. In some embodiments, p is 1. In some embodiments, p is from about 2 to about 8 Drug units per Ligand unit. In some embodiments, p is from about 2 to about 6, 2 to about 5, or 2 to about 4 Drug units per Ligand unit. In some embodiments, p is about 2, about 4, about 6 or about 8 Drug units per Ligand unit The average number of Drugs units per Ligand unit in a preparation from a conjugation reaction may be characterized by conventional means such as mass spectroscopy, ELISA assay, and HPLC. The quantitative distribution of Drug Linker Ligand conjugates in terms of p may also be determined. In some instances, separation, purification, and characterization of homogeneous Drug Linker Ligand conjugates, where p is a certain value from Drug Linker Ligand conjugates with other drug loadings may be achieved by means such as reverse phase HPLC or electrophoresis.

The average number of drugs per antibody in preparations of ADCs from conjugation reactions may be characterized by conventional means such as UV/visible spectroscopy, mass spectrometry, ELISA assay, and HPLC. The quantitative distribution of ADCs in terms of p may also be determined. In some instances, separation, purification, and characterization of homogeneous ADCs where p is a certain value from ADC with other drug loadings may be achieved by means such as reverse phase HPLC or electrophoresis.

For some antibody drug conjugates, p may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond.

Typically, fewer than the theoretical maximum of drug moieties are conjugated to an antibody during a conjugation reaction. An antibody may contain, for example, many lysine residues that do not react with the Drug Linker compound intermediate or Linker unit reagent. Only the most reactive lysine groups may react with an amine-reactive Linker unit reagent. Generally, antibodies do not contain many, if any, free and reactive cysteine thiol groups which may be linked to a Drug moiety via a Linker unit. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of Drug Linker compound intermediate or Linker unit reagent relative to antibody, (ii) limiting the conjugation reaction time or temperature, and (iii) partial or limiting reductive conditions for cysteine thiol modification.

Where more than one nucleophilic group reacts with a Drug Linker compound intermediate, or Linker unit reagent followed by Drug moiety reagent, then the resulting product is a mixture of Drug Linker Ligand conjugates (e.g., ADCs) with a distribution of one or more Drug moieties per Ligand unit (e.g., an antibody). The average number of drugs per Ligand unit (e.g., antibody) may be calculated from the mixture by, for example, dual ELISA antibody assay, specific for antibody and specific for the drug. Individual Drug Linker Ligand conjugate molecules may be identified in the mixture by mass spectroscopy, and separated by HPLC, e.g., hydrophobic interaction chromatography ("Effect of drug loading on the pharmacology, pharmacokinetics, and toxicity of an anti-CD30 antibody-drug conjugate", Hamblett, K J., et al, Abstract No. 624, American Association for Cancer Research; Hamblett et al., 2004, Cancer Research 10:7063; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). Thus, a homogeneous conjugate with a single loading value may be isolated from the conjugation mixture by electrophoresis or chromatography.

The Linker Unit (LU)

A "Linker unit" (LU) is a bifunctional compound which can be used to link a Drug unit and a Ligand unit to form a Drug Linker Ligand conjugate. Such conjugates are useful, for example, in the formation of immuno conjugates directed against tumor associated antigens. Such conjugates allow the selective delivery of cytotoxic drugs to tumor cells.

In one embodiment, the Linker unit of the Drug Linker compound and Drug Linker Ligand conjugate has the formula:

—$W_w$-$A_a$- wherein -A- is a Stretcher unit; a is 1 or 2; each —W— is independently an Amino Acid unit; w is independently an integer ranging from 1 to 12.

In the Drug Linker Ligand conjugate, the Linker unit serves to attach the Drug moiety and the Ligand unit.

The Stretcher Unit

The Stretcher unit (-A-) is capable of linking a Ligand unit to an Amino Acid unit (—W—). In this regard a Ligand (L) unit has a functional group that can form a bond with a functional group of a Stretcher unit. Useful functional groups that can be present on a Ligand unit, either naturally or via chemical manipulation include, but are not limited to, sulfhydryl (—SH), amino, hydroxyl, carboxy, the anomeric hydroxyl group of a carbohydrate, and carboxyl. In one aspect, the Ligand unit's functional groups are sulfhydryl and amino. Sulfhydryl groups can be generated by reduction of an intramolecular disulfide bond of a Ligand unit. Alternatively, sulfhydryl groups can be generated by reaction of an amino group of a lysine moiety of a Ligand unit using 2-iminothiolane (Traut's reagent) or another sulfhydryl generating reagent.

In one embodiment, a is 1 and the Stretcher unit forms a bond with the Amino Acid unit. In another embodiment, a is 2 and one of the Stretcher units forms a bond with the Amino Acid unit.

In some embodiments, the Stretcher unit forms a bond with a sulfur atom of the Ligand unit. The sulfur atom can be derived from a sulfhydryl group of a Ligand unit. Representative Stretcher units of this embodiment are depicted within the square brackets of Formulas IIIa and IIIb, wherein L-, —W—, -D, w and p are as defined above, and $R^9$ can be selected from the group consisting of —$C_1$-$C_{10}$ alkylene-, —$C_3$-$C_8$ carbocyclo-, -arylene-, —$C_1$-$C_{10}$ heteroalkylene-, —$C_3$-$C_3$ heterocyclo-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, and —($C_3$-$C_8$ heterocyclo)-$C_1$-$C_{10}$ alkylene-;

In some embodiments of the Stretcher unit A, —NH—$R^9$— is selected from —NH—$C_1$-$C_{10}$ alkylene-, —NH—$C_1$-$C_{10}$ alkylene-NH—C(O)—$C_1$-$C_{10}$ alkylene-, —NH—$C_1$-$C_{10}$ alkylene-C(O)—NH—$C_1$-$C_{10}$ alkylene-, —NH—($CH_2CH_2O)_r$—, —NH—($CH_2CH_2O)_r$—$CH_2$—, —NH—($CH_2CH_2NH)_r$—($CH_2)_r$, —NH—($CH_2CH_2NH)_r$—($CH_2)_r$—NH—C(O)—($CH_2)_r$—, —NH—($C_3$-$C_8$ carbocyclo)-, —NH-(arylene)-, and —NH—($C_3$-$C_8$ heterocyclo-)-, wherein each r is independently 1-10.

In some embodiments of the Stretcher unit A, —O—$R^9$— is selected from —O—$C_1$-$C_{10}$ alkylene-, —O—$C_1$-$C_{10}$ alkylene-NH—C(O)—$C_1$-$C_{10}$ alkylene-, —O—$C_1$-$C_{10}$ alkylene-C(O)—NH—$C_1$-$C_{10}$ alkylene-, —O—($CH_2CH_2O)_r$—, —O—($CH_2CH_2O)_E$—$CH_2$—, —O—($C_3$-$C_8$ carbocyclo)-, —O-(arylene)-, and —O—($C_3$-$C_8$ heterocyclo-)-, wherein each r is independently 1-10.

In embodiments in which the Stretcher unit A is —O—$R^9$—$R^{11}$—, the ester is a hindered ester.

It is to be understood from all the exemplary embodiments of Formula II, such as III-VI, that even where not denoted expressly, from 1 to 20 Drug moieties are linked to a Ligand unit (p=1-20).

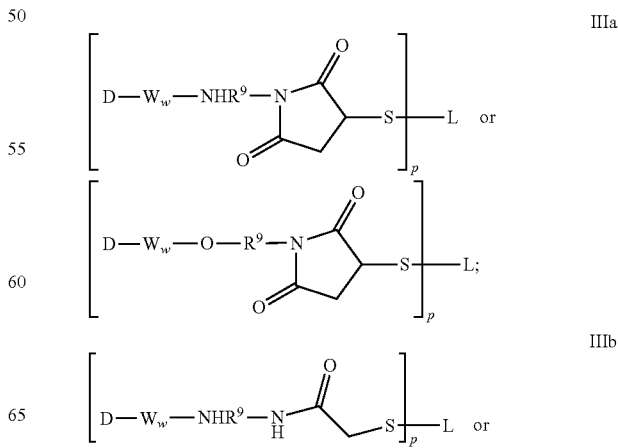

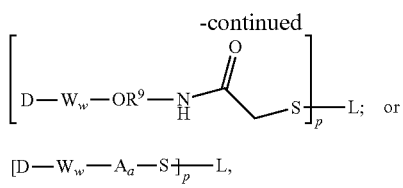

wherein S is thiol group of the Ligand unit.

Some embodiments of Antibody-Drug conjugates include:

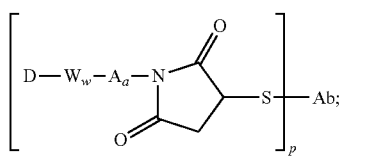

IIIa'

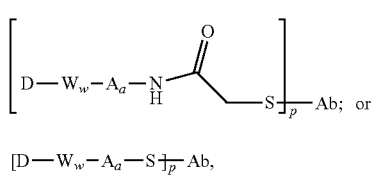

IIIb'

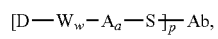 IIIc' wherein S is thiol group of the Ligand unit.

Another illustrative Stretcher unit is that of Formula IIIa, wherein $R^9$ is $C_1$-$C_{30}$ heteroalkylene, such as the following:

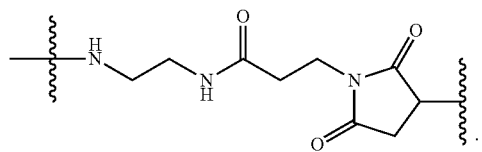 [SMILES: *NCCNC(=O)CCN1C(=O)CC(*)C1=O]

Another illustrative Stretcher unit is that of Formula IIIa, wherein NH—$R^9$ is —NH—($C_6H_4$)—:

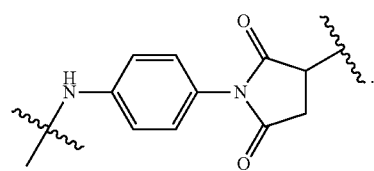 [SMILES: *Nc1ccc(N2C(=O)CC(*)C2=O)cc1]

Another illustrative Stretcher unit is of the following formula:

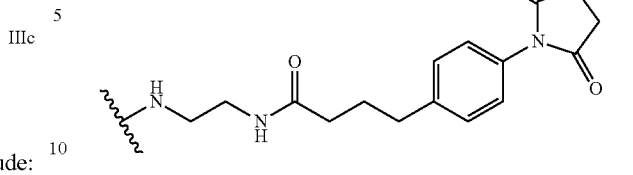

Another illustrative Stretcher unit is that of Formula

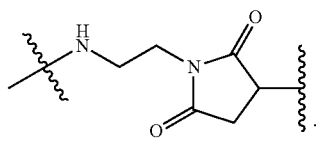 [SMILES: *NCCN1C(=O)CC(*)C1=O]

Another illustrative Stretcher unit is that of the following formula, wherein $R^9$ is $C_1$-$C_{30}$ heteroalkylene of the following formula:

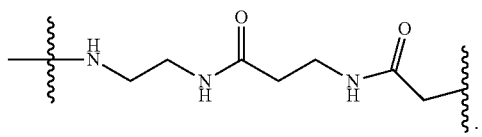

Another illustrative compound is that having the formula:

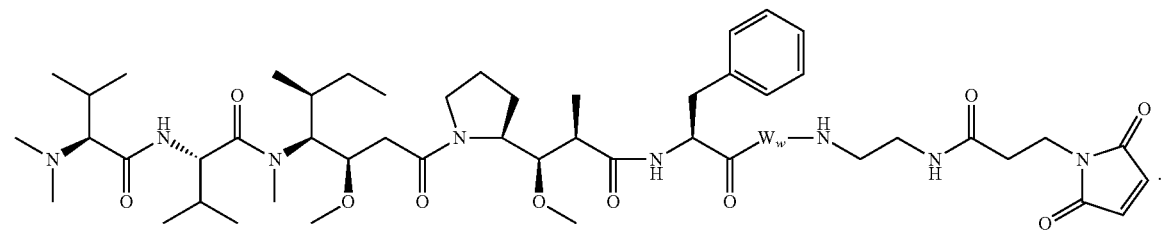

Another illustrative Stretcher unit is that of the following Formula IIIb, wherein $R^9$ is —$C_1$-$C_{30}$ heteroalkylene-:

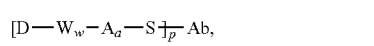

Another illustrative Stretcher unit is that of Formula IIIb, wherein NH—R$^9$ is —NH—(C$_6$H$_4$)—:

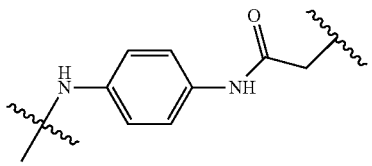 [SMILES: *CC(=O)Nc1ccc(N*)cc1]

Another illustrative Stretcher unit is that of the following Formula IIIb wherein R$^9$ is —C$_1$-C$_{30}$ heteroalkylene-:

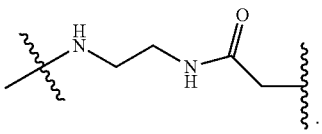 [SMILES: *CC(=O)NCCN*]

The Stretcher unit also can be linked to the Ligand unit via a disulfide bond between a sulfur atom of the Ligand unit and a sulfur atom of the Stretcher unit. A representative Stretcher unit of this embodiment is depicted within the square brackets of the Drug Linker Ligand conjugate of Formula IV, wherein R$^9$, L-, —W—, -D, w and p are as defined above and the left S is part of the Ligand unit.

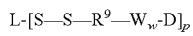  IV

In yet another embodiment, the reactive group of the Stretcher contains a reactive site that can form a bond with a primary or secondary amino group of a Ligand unit. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Drug Linker Ligand conjugates are depicted with the Drug Linker compounds within the square brackets of Formulas Va-Vc, wherein —R$^9$—, L-, —W—, -D, w and p are as defined above and the reactive site of the Ligand Unit is not shown;

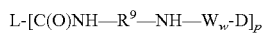 Va$_1$

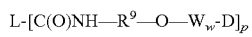 Va$_2$

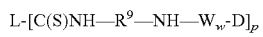 Vb$_1$

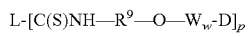 Vb$_2$

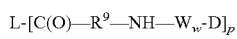 Vc$_1$

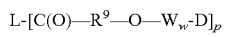 Vc$_2$

In yet another aspect, the reactive group of the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al. (1991) Bioconjugate Chem 2:133-41. Representative Drug Linker Ligand conjugates are depicted with the Drug Linker compounds within the square brackets of Formulas VIa, VIb, and VIc, wherein —R$^9$—, L-, —W—, —Y—, -D, w and p are as defined above and the reactive site of the Ligand Unit is not shown.

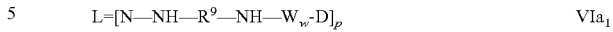 VIa$_1$

 VIa$_2$

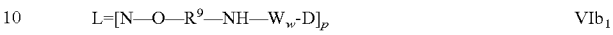 VIb$_1$

 VIb$_2$

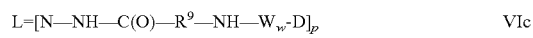 VIc

L=[N—NH—C(O)—R$^9$—O—W$_w$-D]$_p$  VIc

The Amino Acid Unit

The Amino Acid unit (—W—) links the Stretcher unit to the Drug moiety.

—W$_w$— is an amino acid, or a dipeptide, tripeptide, tetrapeptide, pentapeptide, hexapeptide, heptapeptide, octapeptide, nonapeptide, decapeptide, undecapeptide or dodecapeptide unit. In some embodiments, W$_w$ is a dipeptide radical.

Each amino acid W can be natural or unnatural. Similarly, each amino acid can be a D- or L-isomer. In some embodiments, each —W— unit independently has the formula denoted below in the square brackets, and w is an integer ranging from 1 to 12:

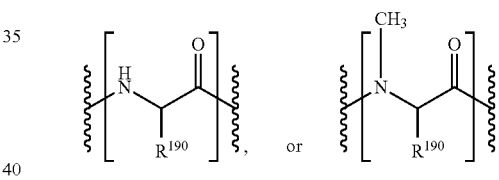

wherein R$^{190}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 4-pyridylmethyl-, phenyl, cyclohexyl,

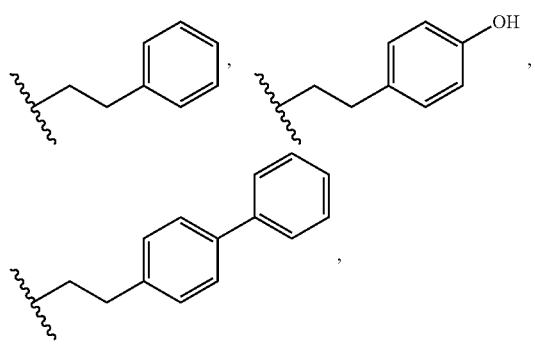

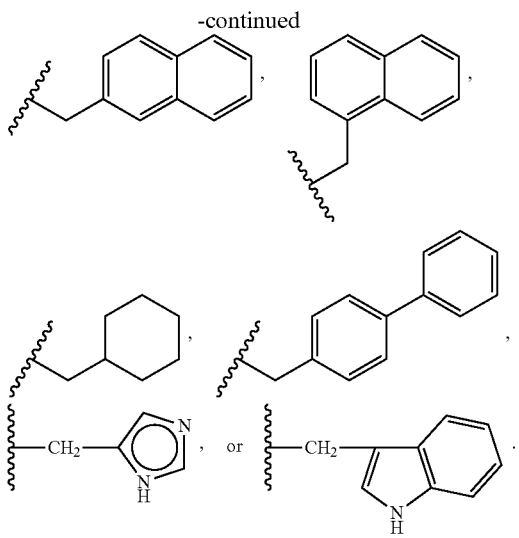

In another embodiment, each —W— unit is independently selected from the group consisting of the following amino acids: alanine, arginine, aspartic acid, asparagine, histidine, glycine, glutamic acid, glutamine, phenylalanine, lysine, leucine, serine, tyrosine, threonine, isoleucine, proline, tryptophan, valine, ornithine, penicillamine, β-alanine, aminoalkanoic acid, aminoalkyrioic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In another embodiment, each —W— unit is independently selected from the group consisting of the following L-(natural) amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In some embodiments, —W— is not cysteine. In some embodiments, —W— is not proline. In some embodiments, —W— is not an N-methyl amino acid.

In another embodiment, each —W— unit is independently selected from the group consisting of the following D-isomers of these natural amino acids: alanine, arginine, aspartic acid, asparagine, histidine, glycine, glutamic acid, glutamine, phenylalanine, lysine, leucine, serine, tyrosine, threonine, isoleucine, tryptophan and valine. In some embodiments, the amino acid unit (—W₁—) proximal to the Drug unit (D) is not a D amino acid.

Illustrative of examples of alanine and derivatives thereof include but are not limited to: alanine (Ala), N-alkyl-alanine, dehydro-alanine, 4-thiazolylalanine, 2-pyridylalanine, 3-pyridylalanine, 4-pyridylalanine, β-(1-naphthyl)-alanine, β-(2-naphthyl)-alanine, α-aminobutyric acid, β-chloro-alanine, β-cyano-alanine, β-cyclopentyl-alanine, β-cyclohexyl-alanine, β-iodo-alanine, β-cyclopentenyl-alanine, β-tBu-alanine, β-cyclopropyl-alanine, β-diphenyl-alanine, β-fluoro-alanine, β-piperazinyl-alanine with the piperazine ring protected or not, β-(2-quinolyl)-alanine, β-(1,2,4-triazol-1-yl)-alanine, β-ureido-alanine, H-β-(3-benzothienyl)-Ala-OH, and H-β-(2-thienyl)-Ala-OH.

Illustrative of examples of arginine and derivatives thereof include but are not limited to: arginine (Arg), N-alkyl-arginine, H-Arg(Me)—OH, H-Arg(NH₂)—OH, H-Arg(NO₂)—OH, H-Arg(Ac)₂—OH, H-Arg(Me)₂—OH (asymmetrical), H-Arg(Me)₂—OH (symmetrical), 2-amino-4-(2'-hydroxyguanidino)-butyric acid (N-ω-hydroxy-nor-arginine) and homoarginine.

Illustrative of examples of aspartic acid and derivatives thereof include but are not limited to: aspartic acid (Asp), N-alkyl-aspartic acid, and H-Asp(OtBu)—OH.

Illustrative of examples of asparagine and derivatives thereof include but are not limited to: asparagine (Asn), N-alkyl-asparagine, and isoasparagine (H-Asp-NH₂).

Illustrative of examples of cysteine (Cys) derivatives (containing no free SH group) thereof include but are not limited to: H-Cys(Acm)—OH, H-Cys(Trt)—OH, H-Cys(tBu)—OH, H-Cys(Bzl)—OH, H-Cys(Et)—OH, H-Cys(SO₃H)—OH, H-Cys(aminoethyl)—OH, H-Cys(carbamoyl)—OH, H-Cys(phenyl)—OH, H-Cys(Boc)—OH, and H-Cys(hydroxyethyl)—OH.

Illustrative of examples of histidine and derivatives thereof include but are not limited to: histidine (His), N-alkyl-histidine, H-His(Boc)—OH, H-His(Bzl)—OH, H-His(1-Me)—OH, H-His(1-Tos)—OH, H-2,5-diiodo-His-OH, and H-His(3-Me)—OH.

Illustrative of examples of glycine and derivatives thereof include but are not limited to: glycine (Gly), N-alkyl-glycine, H-propargylglycine

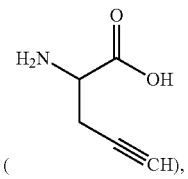

α-aminoglycine (protected or not), β-cyclopropyl-glycine, cyclopentyl-glycine, cyclohexyl-glycine, α-allylglycine, t-Butyl-glycine, neopentylglycine, and phenylglycine.

Illustrative of examples of glutamic acid and derivatives thereof include but are not limited to: glutamic acid (Glu), N-alkyl-glutamic acid, H-Glu(OtBu)—OH, H-γ-hydroxy-Glu-OH, H-γ-methylene-Glu-OH, H-γ-carboxy-Glu(OtBu)₂—OH, and pyroglutamic acid.

Illustrative of examples of glutamine and derivatives thereof include but are not limited to: glutamine (Gln), N-alkyl-glutamine, isoglutamine (H-Glu-NH₂), H-Gln(Trt)—OH, and H-Gln(isopropyl)—OH.

Illustrative of examples of phenylalanine and derivatives thereof include but are not limited to: phenylalanine (Phe), N-alkyl-phenylalanine, H-p-amino-Phe-OH, H-p-amino-Phe(Z)—OH, H-p-bromo-Phe-OH, H-p-Benzyl-Phe-OH, H-p-tBu-Phe-OH, H-p-carboxy-Phe(OtBu)—OH, H-p-carboxy-Phe-OH, H-p-cyano-Phe-OH, H-p-fluoro-Phe-OH, H-3,4-dichloro-Phe-OH, H-p-iodo-Phe-OH, H-p-nitro-Phe-OH, H-p-methyl-Phe-OH, H-pentafluoro-Phe-OH, H-m-fluoro-Phe-OH, H-α-Me-Phe-OH, H-4-phenyl-Phe-OH, homopenylalanine, chloro-phenylalanine and β-homophenylalanine.

Illustrative of examples of lysine and derivatives thereof include but are not limited to: lysine (Lys), N-alkyl-lysine, H-Lys(Boc)—OH, H-Lys(Ac)—OH, H-Lys(Formyl)—OH, H-Lys(Me)₂—OH, H-Lys(nicotinoyl)—OH, H-Lys(Me)₃—OH, H-trans-4,5-dehydro-Lys-OH, H-Lys(Aloc)—OH, H-δ-hydroxy-Lys-OH, H-δ-hydroxy-Lys(Boc)—OH, H-Lys(acetamidoyl)—OH, and H-Lys(isopropyl)—OH.

Illustrative of examples of leucine and derivatives thereof include but are not limited to: leucine (Leu), N-alkyl-leucine, 4,5-dehydroleucine, H-α-Me-Leu-OH, homoleucine, norleucine, and t-leucine.

illustrative of examples of methionine and derivatives thereof include but are not limited to: methionine (Met), H-Met(O)—OH, and H-Met(O)₂—OH.

Illustrative of examples of serine and derivatives thereof include but are not limited to: serine (Ser), N-alkyl-serine, H-Ser(Ac)—OH, H-Ser(tBu)-OH, H-Ser(Bzl)—OH, H-Ser (p-chloro-Bzl)—OH, H-β-(3,4-dihydroxyphenyl)-Ser-OH, H-β-(2-thienyl)-Ser-OH, isoserine N-alkyl-isoserine, and 3-phenylisoserine.

Illustrative of examples of tyrosine and derivatives thereof include but are not limited to: tyrosine (Tyr), N-alkyl-tyrosine, H-3,5-dinitro-Tyr-OH, H-3-amino-Tyr-OH, H-3,5-dibromo-Tyr-OH, H-3,5-diiodo-Tyr-OH, H-Tyr(Me)—OH, H-Tyr(tBu)—OH, H-Tyr(Boc)—OH, H-Tyr(Bzl)—OH, H-Tyr(Et)—OH, H-3-iodo-Tyr-OH, and H-3-nitro-Tyr-OH.

Illustrative of examples of threonine and derivatives thereof include but are not limited to: threonine (Thr), N-alkyl-threonine, allothreonine, H-Thr(Ac)—OH, H-Thr (tBu)—OH, and H-Thr(Bzl)—OH.

Illustrative of examples of isoleucine and derivatives thereof include but are not limited to: isoleucine (Ile), N-alkyl-isoleucine, allo-isoleucine, and norleucine.

Illustrative of examples of tryptophan and derivatives thereof include but are not limited to: tryptophan (Trp), N-alkyl-tryptophan, H-5-Me-Trp-OH, H-5-hydroxy-Trp-OH, H-4-Me-Trp-OH, H-α-Me-Trp-OH, H-Trp(Boc)-OH, H-Trp(Formyl)—OH, and H-Trp(Mesitylene-2-sulfonyl)—OH.

Illustrative of examples of proline and derivatives thereof include but are not limited to: praline (Pro), N-alkyl-proline, homoproline, thioproline, hydroxyproline (H-Hyp-OH), H-Hyp(tBu)-OH, H-Hyp(Bzl)-OH, H-3,4-dehydro-Pro-OH, 4-keto-proline, α-Me-Pro-OH, and H-4-fluoro-Pro-OH.

Illustrative of examples of valine and derivatives thereof include but are not limited to: valine (Val), N-alkyl-valine, H-α-Me-Val-OH, and norvaline.

Illustrative of examples of ornithine and derivatives thereof include but are not limited to: ornithine, N-alkyl-ornithine, H-Orn(Boc)—OH, H-Orn(Z)—OH, H-α-difluoro-Me-Orn-OH (Eflornitine), and H-Orn(Aloc)—OH.

Illustrative of examples of penicillamine and derivatives thereof include but are not limited to: penicillamine, H-penicillamine(Acm)—OH (H-β,β-dimethylcys(Acm)—OH) and N-alkyl-penicillamine.

Illustrative of examples of β-alanine and derivatives thereof include but are not limited to: β-alanine, N-alkyl-β-alanine, and dehydro-alanine.

Illustrative of examples of an aminoalkynoic acid and derivatives thereof include but are not limited to: N-alkylaminoalkanoic acid, aminobutyric acid, 4-(neopentyloxysulfonyl)-aminobutyric acid, ε-aminocaproic acid, α-aminoisobutyric acid, piperidylacetic acid, 3-aminopropionic acid, 3-amino-3-(3-pyridyl)-propionic acid, and 5-aminopentanioic acid (aminovaleric acid).

Illustrative of examples of an aminoalkynoic acid and derivatives thereof include but are not limited to: N-alkylaminoalkynoic acid, 6-amino-4-hexynoic acid, 6-(Boc-amino)-4-hexynoic acid.

Illustrative of examples of an aminoalkanedioic acid and derivatives thereof include but are not limited to: N-alkylaminoalkanedioic acid, 2-aminohexanedioic acid, 2-aminoheptanedioic acid, 2-aminooctanedioic acid (H-Asu-OH).

Illustrative of examples of an aminobenzoic acid and derivatives thereof include but are not limited to: N-alkylaminobenzoic acid, 2-aminobenzoic acid, 3-aminobenzoic acid, and 4-aminobenzoic acid.

Illustrative of examples of an amino-heterocyclo-alkanoic acid and derivatives thereof include but are not limited to: N-alkylamino-heterocyclo-alkanoic acids, 4-amino-1-methyl-1H-imidazol-2-carboxylic acid, 4-amino-1-methyl-1H-pyrrole-2-carboxylic acid, 4-amino-piperidine-4-carboxylic acid (H-Pip-OH; 1-protected or not), 3-amino-3-(3-pyridyl)-propionic acid.

Illustrative of examples of a heterocyclo-carboxylic acid and derivatives thereof include but are not limited to: azetidine-2-carboxylic acid, azetidine-3-carboxylic acid, piperidine-4-carboxylic acid, and thiazolidine-4-carboxylic acid.

Illustrative of examples of citrulline and derivatives thereof include but are not limited to: citrulline (cit), N-alkyl-citrulline, thiocitrulline, S-methyl-thiocitrulline, and homocitrulline.

Illustrative of examples of statine and derivatives thereof include but are not limited to: statine, N-alkyl-statine, cyclohexylstatine, and phenylstatine.

Illustrative of examples of diaminoalkanoic acid (Dab) and derivatives thereof include but are not limited to: N-alkyl-diamino-alkanoic acids, N,N-dialkylamino-alkanoic acids, α,γ-diaminobutyric acid (H-Dab-OH), H-Dab(Aloc)—OH, H-Dab(Boc)-OH, H-Dab(Z)—OH, α,β-diaminopropionic acid and its side-chain protected versions.

In some embodiments, the linkage between the Amino Acid unit and the Drug unit can be enzymatically cleaved by one or more enzymes, including a tumor-associated protease, to liberate the Drug unit (-D), which in one embodiment is protonated in vivo upon release to provide a Drug (D).

Useful —$W_w$— units—Drug unit can be designed and optimized in their selectivity for enzymatic cleavage by a particular enzyme, for example, a tumor-associated protease. In one embodiment, a linkage between the —$W_w$— unit and the Drug unit is that which cleavage is catalyzed by cathepsin B, C and D, or a plasmin protease.

In one group of embodiments, $W_1$, the first W unit attached to the carboxyl-terminus of the Drug unit of formula D, cannot form a secondary amide with the C-terminal amino acid of the Drug unit of formula D.

In one embodiment, w is 1. In certain embodiments, w is an integer ranging from 2 to 12. In one embodiment, —$W_w$— is a dipeptide, tripeptide, tetrapeptide or pentapeptide. In one group of embodiments, w is 2.

In certain embodiments, the Amino Acid unit can comprise only natural amino acids. In other embodiments, the Amino Acid unit can comprise only non-natural amino acids. In some embodiments, the Amino Acid unit can comprise a natural amino acid linked to a non-natural amino acid. In some embodiments, the Amino Acid unit can comprise a natural amino acid linked to a D-isomer of a natural amino acid.

In one group of embodiments, at least one W is an L-amino acid. In another group of embodiments, at least one W is a D-amino acid. In some embodiments, at least one W has a chiral center in the S-configuration. In some embodiments, at least one W has a chiral center in the R-configuration.

In some embodiments of the Amino Acid unit, the Amino Acid unit is $W_w$ is selected from the group consisting of -Methionine-(L)Lysine-, and -Asparagine-(L)Lysine-. In one aspect of the Amino Acid unit, the Amino Acid unit $W_w$ is selected from the group consisting of -Tyrosine-(D)Aspartic Acid-, -Norvaline-(D)Aspartic Acid-, -Phenylglycine-(D)Lysine-, -Methionine-(D)Lysine-, and -Asparagine-(D)Lysine-.

The Ligand Unit (L)

The Ligand unit (L-) includes within its scope any unit of a Ligand (L) that specifically binds or reactively associates or complexes with a receptor, antigen or other receptive moiety associated with a given target-cell population. A Ligand unit is a molecule that binds to, complexes with, or reacts with a receptor, antigen or other receptive moiety of a cell population sought to be therapeutically or otherwise biologically modified. In one aspect, the Ligand unit acts to deliver the Drug unit to the particular target cell population with which the Ligand unit interacts. Such Ligands include, but are not limited to, proteins, polypeptides and peptides. Suitable Ligand units include, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A Ligand unit can form a bond to a Stretcher unit. A Ligand unit can form a bond to the Stretcher unit of the Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These hetero atoms can be present on the Ligand in the Ligand's natural state, for example a naturally-occurring antibody, or can be introduced into the Ligand via chemical modification.

In one embodiment, a Ligand unit has a sulfhydryl group and the Ligand unit bonds to the Linker unit via the sulfhydryl group's sulfur atom.

In another embodiment, the Ligand has lysine residues that can react with activated esters (such esters include, but are not limited to, N-hydroxysuccinimde, pentafluorophenyl, and p-nitrophenyl esters) of the Stretcher unit of the Linker unit and thus form an amide bond consisting of the nitrogen atom of the Ligand unit and the C=O group of the Linker unit.

In yet another aspect, the Ligand unit has one or more lysine residues that can be chemically modified to introduce one or more sulfhydryl groups. The Ligand unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the Ligand unit can have one or more carbohydrate groups that can be chemically modified to have one or more sulfhydryl groups. The Ligand unit bonds to the Linker unit (the Stretcher Unit) via the sulfhydryl group's sulfur atom.

In yet another embodiment, the Ligand unit can have one or more carbohydrate groups that can be oxidized to provide an aldehyde (—CHO) group (see, e.g., Laguzza, et al., 1989, *J. Med. Chem.* 32(3):548-55). The corresponding aldehyde can form a bond with a reactive site on a Stretcher unit. Reactive sites on a Stretcher that can react with a carbonyl group on a Ligand include, but are not limited to, hydrazine and hydroxylamine. Other protocols for the modification of proteins for the attachment or association of Drug units are described in Coligan et al., *Current Protocols in Protein Science*, vol. 2, John Wiley & Sons (2002) (incorporated herein by reference).

Useful non-immunoreactive protein, polypeptide, or peptide Ligand units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. No. 4,816,567; and U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-

1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, *Biotechnology* 12:899-903). Human antibodies can also be produced using various techniques known in the art, including phage display libraries (see, e.g., Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics*, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, N.C.) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART MI95 (Protein Design Labs, Inc., CA) and SGN-33 (Seattle Genetics, Inc., WA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEACIDE (Immunomedics, N.J.) which is a humanized anti-CEA antibody for the treatment of colorectal cancer.

Other antibodies useful in the treatment of cancer include, but are not limited to, antibodies against the following antigens (where exemplary cancers that can be treated with the antibody are in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE -4 (carcinomas), anti-transferrin receptor (carcinomas), p97 (melanoma), MUC1 (breast cancer), CEA (colorectal), gp100 (melanoma), MART1 (melanoma), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Many other internalizing antibodies that bind to tumor associated antigens can be used and have been reviewed (see, e.g., Franke et al., 2000, *Cancer Biother. Radiopharm.* 15, 459-76; Murray, 2000, *Semin Oncol.* 27:64-70; Breitling and Dubel, *Recombinant Antibodies*, John Wiley, and Sons, New York, 1998).

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

In an exemplary embodiment of the Drug Linker Ligand conjugate, the Ligand unit is an antibody Ab that binds at least one of CD19, CD20, CD30, CD33, CD70, BCMA, Glypican-3, Liv-1 and Lewis Y antigen, w=2, and D has Formula IIb.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques. In another embodiment, useful antibodies are immunospecific for the treatment of autoimmune diseases include, but are not limited to, anti-nuclear antibody; anti-dsDNA; anti-ssDNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL-70 antibody; anti-Jo antibody; anti-$U_1$RNP antibody; anti-La/SSB antibody; anti-SSA; anti-SSB antibody; anti-perital cells antibody; anti-histones antibody; anti-RNP antibody; C-ANCA antibody; P-ANCA antibody; anti-centromere antibody; anti-fibrillarin antibody and anti-GBM antibody.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the Ligand unit binds to an activated lymphocyte that is associated with an autoimmune disease.

In another specific embodiment, useful Ligand units immunospecific for a viral or a microbial antigen are monoclonal antibodies. The antibodies may be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment of viral or microbial infection in accordance with the methods disclosed herein. Examples of antibodies useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenies) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized $IgG_1$ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia* vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma spp., Rickettsia prowazeki, Rickettsia tsutsugumushi, and Chlamydia spp.); pathogenic fungi (Coccidioides immitis, Aspergillus fumigatus, Candida albicans, Blastomyces dermatitidis, Cryptococcus neoformans, and Histoplasma capsulatum); protozoa (Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria); or Hehniniths (Enterobius vermicularis, Trichuris trichiura, Ascaris lumbricoides, Trichinella spiralis, Strongyloides stercoralis, Schistosoma japonicum, Schistosoma mansoni, Schistosoma haematobium, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

Screening for Drug Linker Ligand Conjugates

Transgenic animals and cell lines are particularly useful in screening Drug Linker Ligand conjugates (e.g., ADCs) for prophylactic or therapeutic treatments of diseases or disorders involving overexpression of a target protein (e.g., CD19, CD20, CD30, CD33, CD70, BCMA, Glypican-3, Liv-1 and Lewis Y). The screening of Drug Linker Ligand conjugates as ADCs is exemplified herein.

Transgenic animals and cell lines are particularly useful in screening ADCs. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. Candidate ADCs may be screened serially and individually, or in parallel under medium or high-throughput screening format. The rate at which the ADCs may be screened for utility for prophylactic or therapeutic treatments of diseases or disorders is limited only by the rate of synthesis or screening methodology, including detecting/measuring/analysis of data.

One embodiment is a screening method comprising (a) transplanting cells from a stable cancer cell line into a non-human animal, (b) administering an ADC drug candidate to the non-human animal and (c) determining the ability of the candidate to inhibit the formation of tumors from the transplanted cell line.

One embodiment is a screening method comprising (a) transplanting cells from a stable cancer cell line into a non-human animal and allowing the tumor to establish in the animal, (b) administering an ADC drug candidate to the non-human animal and (c) determining the ability of the candidate to inhibit the formation of tumors from the transplanted cell line.

Another embodiment is a screening method comprising (a) contacting cells from a stable cancer cell line with an ADC drug candidate and (b) evaluating the ability of the ADC candidate to induce cell death. In one embodiment the ability of the ADC candidate to induce apoptosis is evaluated.

One embodiment is a screening method comprising (a) transplanting cells from a stable renal cell cancer cell line into a non-human animal, (b) administering an ADC drug candidate to the non-human animal and (c) determining the ability of the candidate to inhibit the formation of tumors from the transplanted cell line.

One embodiment is a screening method comprising (a) transplanting cells from a stable renal cell cancer cell line into a non-human animal and allowing the tumor to establish in the animal, (b) administering an ADC drug candidate to the non-human animal and (c) determining the ability of the candidate to inhibit the formation of tumors from the transplanted cell line.

Another embodiment is a screening method comprising (a) contacting cells from a stable Hodgkin's disease cell line with an ADC drug candidate and (b) evaluating the ability of the ADC candidate to induce cell death. In one embodiment the ability of the ADC candidate to induce apoptosis is evaluated.

In one embodiment, candidate ADCs are screened by being administered to the transgenic animal over a range of doses, and evaluating the animal's physiological response to the candidate over time. Administration may be by suitable injection, or otherwise, depending on the chemical nature of the candidate being evaluated. In some cases, it may be appropriate to administer the candidate in conjunction with another therapeutic agent that would enhance the efficacy of the candidate. If cell lines derived from the subject transgenic animals are used to screen for candidates useful in treating various disorders, the test candidates are added to the cell culture medium at an appropriate time, and the cellular response to the candidate is evaluated over time using the appropriate biochemical and/or histological assays. In some cases, it may be appropriate to apply the candidate of interest to the culture medium in conjunction with other therapeutic agents that would enhance the efficacy of the candidate.

Thus, provided herein are assays for identifying Drug Linker Ligand conjugates (such as ADCs) which specifically target and bind a target protein, the presence of which is correlated with abnormal cellular function, and in the pathogenesis of cellular proliferation and/or differentiation that is causally related to the development of tumors.

To identify growth inhibitory candidates that specifically target an antigen of interest, the assay described in U.S. Pat. No. 5,677,171 can be performed. One may screen for compounds which inhibit the growth of cancer cells overexpressing antigen of interest derived from transgenic animals. According to this assay, cancer cells overexpressing the antigen of interest are grown in a 1:1 mixture of F12 and DMEM medium supplemented with 10% fetal bovine serum, glutamine and penicillin streptomycin. The cells are plated at 20,000 cells in a 35 mm cell culture dish (2 mls/35 mm dish) and the test compound is added at various concentrations. After six days, the number of cells, compared to untreated cells is counted using an electronic COULTER™ cell counter. Those compounds which inhibit cell growth by about 20-100% or about 50-100% may be selected as growth inhibitory compounds.

To select for candidates that induce cell death, loss of membrane integrity as indicated by, e.g., PI, trypan blue or 7AAD uptake may be assessed relative to a control. The PI uptake assay uses cells isolated from the tumor tissue of interest of a transgenic animal. According to this assay, the cells are cultured in Dulbecco's Modified Eagle Medium (D-MEM):Ham's F-12 (50:50) supplemented with 10% heatinactivated FBS (Hyclone) and 2 mM L-glutamine. Thus, the assay is performed in the absence of complement and immune effector cells. The cells are seeded at a density of $3\times10^6$ per dish in 100×20 mm dishes and allowed to attach overnight. The medium is then removed and replaced with fresh medium alone or medium containing various concentrations of the candidate. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those candidates that induce statistically significant levels of cell death as determined by PI uptake may be selected as cell death-inducing compounds.

In order to select for candidates that induce apoptosis, an annexin binding assay using cells established from the tumor tissue of interest of the transgenic animal is performed. The cells are cultured and seeded in dishes as discussed in the preceding paragraph. The medium is then removed and replaced with fresh medium alone or medium containing 10 µg/ml of the antibody drug conjugate (ADC). Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g., annexin V-FITC) (1 µg/ml). Samples may be analyzed using a FACSCAN™ flow cytometer and FACSCONVERT™ CellQuest software (Becton Dickinson). Those candidates which induce statistically significant levels of annexin binding relative to control are selected as apoptosis-inducing compounds.

In Vitro Cell Proliferation Assays

Generally, the cytotoxic or cytostatic activity of a Drug Linker Ligand conjugate, such as an ADC, is measured by: exposing mammalian cells having receptor proteins to the antibody of the conjugate in a cell culture medium; culturing the cells for a period from about 6 hours to about 5 days, preferably 96 hours; and measuring cell viability. Cell-based in vitro assays are used to measure viability (proliferation), cytotoxicity, and induction of apoptosis (caspase activation) of a Drug Linker Ligand conjugate. The screening of Drug Linker Ligand conjugates as ADCs is exemplified herein.

The in vitro potency of antibody drug conjugates is measured by a cell proliferation assay (see Examples). The CellTiter-Glo® Luminescent Cell Viability Assay is a commercially available (Promega Corp., Madison, Wis.), homogeneous assay method based on the recombinant expression of *Coleoptera* luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al., 1993, *J. Immunol. Meth.* 160:81-88, U.S. Pat. No. 6,602,677). The CellTiter-Glo® Assay is conducted in 96 well format, making it amenable to automated high-throughput screening (HTS) (Cree et al., 1995, *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e., 3 hours, show the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g., 96 or 384 well format. Data can be recorded by luminometer or CCD camera imaging device. The luminescence output is presented as relative light units (RLU), measured over time.

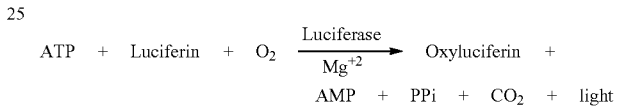

The anti-proliferative effects of antibody drug conjugates can be measured by the cell proliferation, in vitro cell killing assay above against different breast tumor cell lines.

In Vivo Plasma Clearance and Stability

Pharmacokinetic plasma clearance and stability of Drug Linker Ligand conjugates, such as ADCs, can be investigated in rats and cynomolgus monkeys over time. The screening of Drug Linker Ligand conjugates as ADCs is exemplified herein.

Rodent Toxicity

Antibody drug conjugates and an ADC-minus control, "Vehicle", are evaluated in an acute toxicity rat model. Toxicity of ADCs is investigated by treatment of male and female Sprague-Dawley rats with the ADCs and subsequent inspection and analysis of the effects on various organs. Gross observations include changes in body weights and signs of lesions and bleeding. Clinical pathology parameters (serum chemistry and hematology), histopathology, and necropsy are conducted on dosed animals. It is considered that weight loss, or weight change relative to animals dosed only with Vehicle, in animals after dosing with ADC is a gross and general indicator of systemic or localized toxicity.

Hepatotoxicity is measured by elevated liver enzymes, increased numbers of mitotic and apoptotic figures and hepatocyte necrosis. Hematolymphoid toxicity is observed by depletion of leukocytes, primarily granuloctyes (neutrophils), and/or platelets, and lymphoid organ involvement, i.e. atrophy or apoptotic activity. Toxicity is also noted by gastrointestinal tract lesions such as increased numbers of mitotic and apoptotic figures and degenerative enterocolitis.

Enzymes indicative of liver injury that are studied include:
AST (aspartate aminotransferase)
    Localization: cytoplasmic; liver, heart, skeletal muscle, kidney
    Liver:Plasma ratio of 7000:1
    T1/2: 17 hrs
ALT (alanine aminotransferase)

Localization: cytoplasmic; liver, kidney, heart, skeletal muscle
Liver:Plasma ratio of 3000:1
T1/2: 42 hrs; diurnal variation
GGT (g-glutamyl transferase)
Localization: plasma membrane of cells with high secretory or absorptive capacity; liver, kidney, intestine
Poor predictor of liver injury; commonly elevated in bile duct disorders
Cynomolgus Monkey Toxicity/Safety
Similar to the rat toxicity/safety study, cynomolgus monkeys are treated with ADCs followed by liver enzyme measurements, and inspection and analysis of the effects on various organs. Gross observations include changes in body weights and signs of lesions and bleeding. Clinical pathology parameters (serum chemistry and hematology), histopathology, and necropsy are conducted on dosed animals.

Synthesis of the Compounds

The Drug Linker Ligand conjugates and Drug Linker compounds can be made using the synthetic procedures outlined below in Schemes 1-4. As described in more detail below, the Drug Linker Ligand conjugates and Drug Linker compounds can be prepared using a section of a Linker unit having a reactive site for binding to the Drug unit. In one aspect, a second section of the Linker unit is introduced which has a second reactive site e.g., an electrophilic group that is reactive to a nucleophilic group present on a Ligand unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a Linker unit and forms a covalent bond to a Linker unit. Useful electrophilic groups include, but are not limited to, maleimide and haloacetamide groups. The electrophilic group provides a convenient site for antibody attachment.

In another embodiment, a Linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker unit can react with an electrophilic group on an antibody and form a covalent bond to the antibody. Useful nucleophilic groups on a Linker unit include, but are not limited to, hydrazide, oxime, amino, hydrazine, thiosemicarbazone, hydrazine carboxylate, and arylhydrazide. The electrophilic group on an antibody provides a convenient site for attachment to a Linker unit.

Amino functional groups are also useful reactive sites for a Linker unit because they can react with carboxylic acid, or activated esters of a Drug unit to form an amide linkage. Typically, peptide-based Drugs units can be prepared by forming a peptide bond between two or more amino acids and/or peptide fragments. Such peptide bonds can be prepared, for example, according to the liquid phase synthesis method (see, e.g., Schröder and Lübke, "The Peptides", volume 1, pp 76-136, 1965, Academic Press) that is well known in the field of peptide chemistry.

The synthesis of an illustrative Stretcher having an electrophilic maleimide group is illustrated below in Schemes 1-3. General synthetic methods useful for the synthesis of Drug Linker compounds are described in Scheme 1. Schemes 2 and 3 show the construction of a Linker unit having an electrophilic maleimide group. Scheme 4 outlines the attachment of an antibody to a Drug Linker compound to form a Drug Linker Ligand (Antibody) conjugate.

As described in more detail below, the Drug Linker Ligand conjugates can be prepared using a section of the Linker having a reactive site for binding to the Drug unit and introducing another section of the Linker unit having a reactive site for a Ligand unit. In one aspect, a Linker unit has a reactive site which has an electrophilic group that is reactive with a nucleophilic group present on a Ligand unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a Linker unit and forms a covalent bond to a Linker unit. Useful electrophilic groups include, but are not limited to, maleimide and haloacetamide groups.

In another embodiment, a Linker unit has a reactive site which has a nucleophilic group that is reactive with an electrophilic group present on a Ligand unit, such as an antibody. The electrophilic group on an antibody provides a convenient site for attachment to a Linker unit. Useful electrophilic groups on an antibody include, but are not limited to, aldehyde and ketone carbonyl groups. The heteroatom of a nucleophilic group of a Linker unit can react with an electrophilic group on an antibody and form a covalent bond to the antibody. Useful nucleophilic groups on a Linker unit include, but are not limited to, hydrazide, oxime, amino, hydrazine, thiosemicarbazone, hydrazine carboxylate, and arylhydrazide.

Drug Moiety and Linker Synthesis

Typically, peptide-based Drugs can be prepared by forming a peptide bond between two or more amino acids and/or peptide fragments. Such peptide bonds can be prepared, for example, according to the liquid phase synthesis method (see E. Schröder and K. Lüke, "The Peptides", volume 1, pp 76-136, 1965, Academic Press) that is well known in the field of peptide chemistry.

The auristatin/dolastatin Drug moieties may be prepared according to the general methods of: U.S. Pat. No. 5,635,483; U.S. Pat. No. 5,780,588; Pettit et al., 1989, *J. Am. Chem. Soc.* 111:5463-5465; Pettit et al., 1998, *Anti-Cancer Drug Design* 13:243-277; and Pettit et al., 1996, *J. Chem. Soc. Perkin Trans.* 1 5:859-863.

Scheme 1. Solid Phase Synthesis Route

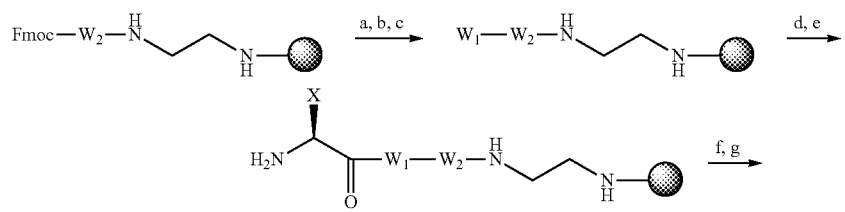

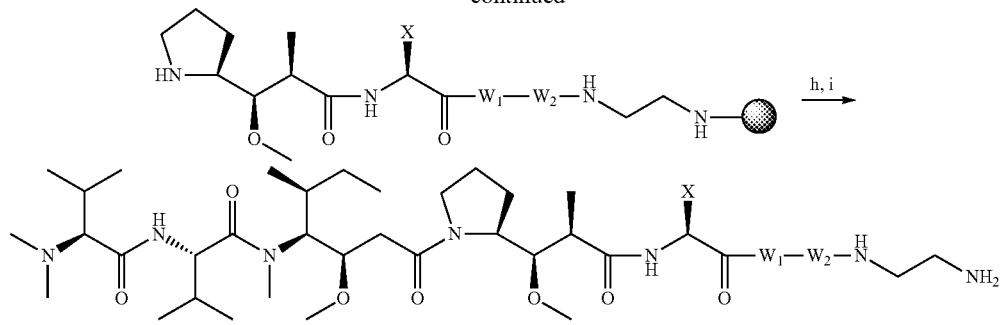

Reaction conditions (a): 20% piperidine/DMF, (b) Fmoc—W$_1$ (2-5 equiv.), HATU (2-5 equiv.) and DIEA, (4-10 equiv.), (c) 20% piperidine/DMF, (d) Fmoc—NH—CH(X)—COOH (2 equiv.) HATU (2 equiv.) and DIEA (4 equiv.), (e) 20% piperidine/DMF, (f) Fmoc Dap (2 equiv.) HATU (2 equiv.) and DIEA (4 equiv.), (g) 20% piperidine/DMF, (h) Dov—Val—Dil—OH (2 equiv.), HATU (2 equiv.), and DIEA (4 equiv.), (i): 95% TFA/dichloromethane.

Amino acids not commercially available pre-loaded on an appropriate acid labile resin, preferably 1,2-diaminoethane trityl resin, can be loaded onto 1,2-diaminoethane trityl resin as described in General Procedure SP(a). Loading can be determined by spectrophotometric Fmoc-quantitation assay. Loading levels (mmol/g) of commercially available pre-loaded amino acids on 1,2-diaminoethane trityl resin can be determined as described in General Procedure SP(b). Peptides can then be assembled on the resin loaded with the amino acids of the Amino Acid unit by coupling Fmoc-amino acid using appropriate coupling reagent, preferably HATU/DIEA, followed by Fmoc deprotection and subsequent coupling with reagents which form the Drug unit. Drug unit synthesis can be accomplished by then coupling Fmoc-Dolaproine using appropriate coupling agent, preferably HATU/DIEA, followed by Fmoc deprotection and subsequent coupling of Fmoc-MeVal-Val-Dil tripeptide. Solid phase coupling routine is well established in the art and is described in General Procedure SP(c). Final deprotection of peptides and cleavage off resin can be readily performed following General Procedure SP(d).

Drug Linker compounds containing only one amino acid in the Linker unit were prepared following the above procedure but skipping steps (b) and (c).

Drug Linker compounds containing more that 2 amino acids in the Linker unit were prepared by incorporating additional steps (b), (c) with Fmoc-W$_3$ Monomethyl versions of Drug Linkers were prepared by substituting in step (h) Dov-Val-Dil-OH with Fmoc-MeVal-Val-Dil-OH. Fmoc was removed by 20% piperidine/DMF treatment prior to cleaving compound off the resin, step (i).

Auristatins containing various amino acids at the C-terminus of the drug were generated using corresponding Fmoc-NH—CH(X)—COOH in step (d): for example, Fmoc-Phenylalanine for auristatin F (AF); Fmoc-Methionine for auristatin M (AM); Fmoc-Tryptophan for auristatin W (AW), etc.

General Procedure SP(a). Resin Loading

Fmoc-amino acid is suspended in anhydrous solvent such as $CH_2Cl_2$ and DIEA. The resulting mixture is added to a syringe containing 1,2-diaminoethane trityl resin. The mixture is agitated at room temperature, then the resin is filtered, washed with solvents, such as DCM/MeOH/DIEA, MeOH, DCM, DMF, ethyl ether, and is dried in vacuo. The resin is then left under vacuum overnight.

Loading is determined by Fmoc-quantitation. A known quantity of resin is weighed in a volumetric flask and to the flask is added a solvent such as 20% piperidine/DMF. The mixture is allowed to cleave for about 1 h, with occasional agitation. To the flask is transferred a solvent such as DMF to bring the total volume to a set level (e.g., 10 mL). A blank solution is prepared with an equivalent volume of 20% piperidine/DMF in a volumetric flask. The spectrophotometer is zeroed with the blank solution. The absorbance is measured at 301 nm and the loading level is given by:

Loading(mmol/g)=$A_{301}$×10 mL/7800×wt whereby $A_{301}$ is the absorbance at 301 nm, 7800 is the extinction coefficient of the piperidine-fluorenone adduct, and wt is the weight of resin used in milligrams. Fmoc quantitiation is generally performed in duplicate.

General Procedure SP(b). Fmoc Quantitation of Commercially Available Pre-Loaded Resins Fmoc-Cl is dissolved in anhydrous solvent, such as $CH_2Cl_2$ to make a working solution. This solution is transferred to a plastic syringe containing amino acid-1,2-diaminoethane trityl resin. The mixture is agitated for about 2 h. The resin is then filtered and washed with appropriate solvents, such as DMF, $CH_2Cl_2$ or ethyl ether, and dried in-vacuo for about 2 h. The resin is subjected to Kaiser amine test. Upon negative results (free amine fully protected) the Fmoc quantitation to obtain loading level is performed as shown in General Procedure SP(a).

General Procedure SP(c). Solid Phase Peptide Coupling Using HATU

A 20% piperidine in DMF solution is added to the syringe with a PET frit containing resin, and the mixture is agitated for about 2 h. The resin is then filtered, washed with appropriate solvents such as DMF, DCM or ethyl ether, and is dried in-vacuo for about 2 h.

A solution of Fmoc-amino acid, HATU and DIEA in DMF was then added to the resin which was shaken for about 4 hrs, washed, and dried. In this manner, Fmoc-Phe, Fmoc-Dap, and Dov-Val Dil-OH (or Fmoc-MeVal-Val-Dil) were sequentially coupled on the resin as described previously.

General Procedure SP(d). Final Deprotection and Cleavage Off Resin

The resin was then treated with a solution of 95% TFA/dichloromethane, and washed with 95% TFA/dichloromethane. The combined filtrate was allowed to stand at room temperature for about 30 min, then concentrated to dryness. The product was purified by reverse phase preparative HPLC.

Alternatively, Drug Linkers can be prepared on chlorotrityl resin as shown in Scheme 1a:

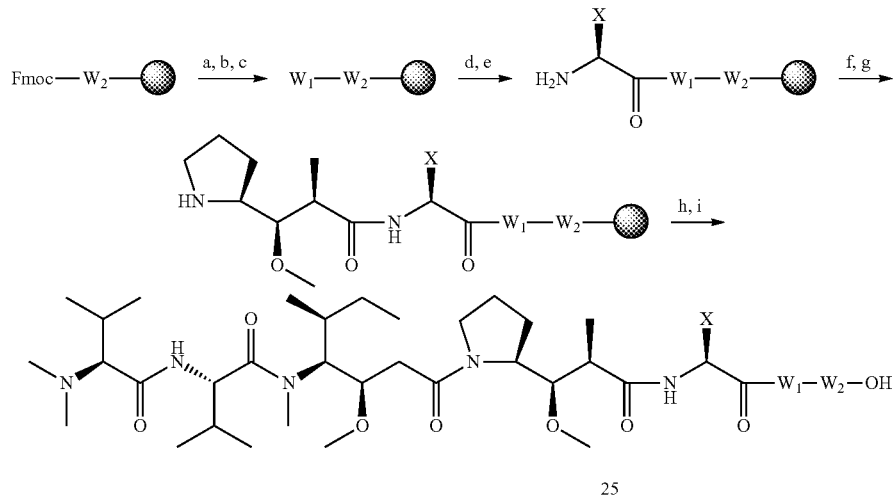

The same reaction conditions are used as in Scheme 1. (Note: the free hydroxyl after steps h, i is part of $W_2$.)

Completion of Drug Linker Synthesis

To complete the synthesis of the Drug Linker compound, and to introduce a reactive site that will be used for conjugation with a ligand, the partial Drug Linker compound, as cleaved off the resin, is reacted with another portion of a Stretcher unit to form a complete Drug Linker compound.

In one aspect, the partial Drug Linker compound reacts with a carboxylic acid or an activated ester of the second portion of the Stretcher unit. See, for example Scheme 2:

Scheme 2

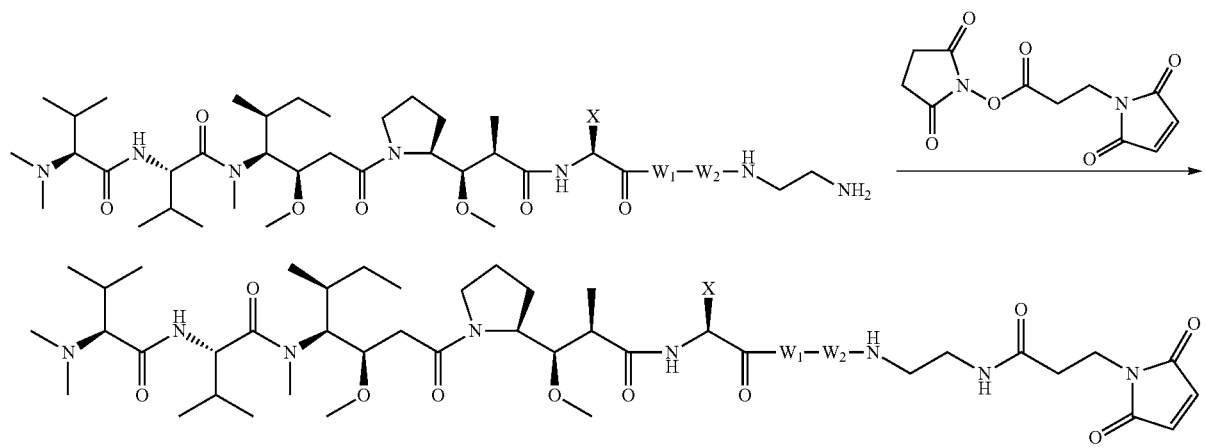

Reaction Conditions: Maleimidopropionic Acid NHS Ester (2 Equiv.), DIEA (2 Equiv.), DMF.

In another aspect, the partial Drug Linker compound prepared according to Scheme 1a reacts with an amine of the second portion of the Stretcher unit following standard coupling procedures of peptide chemistry. See for example Scheme 2a.

Scheme 2a

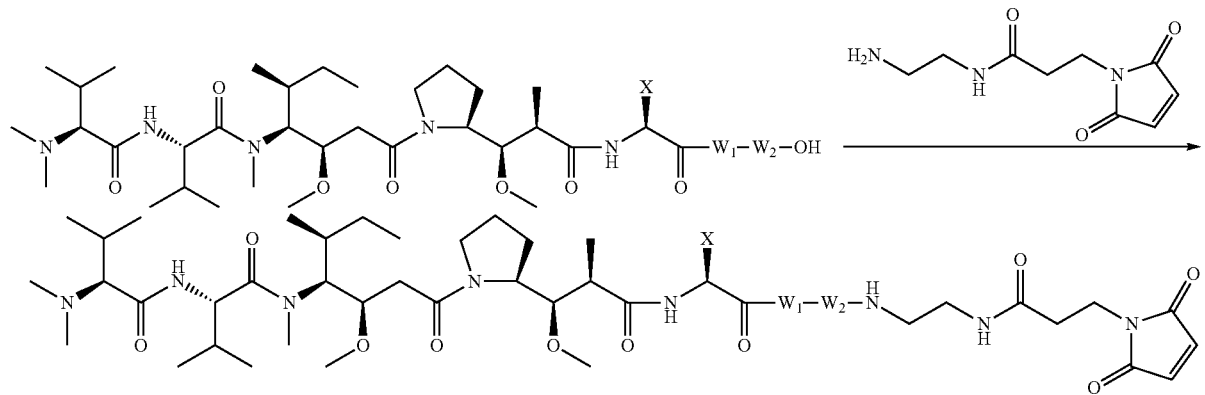

In one aspect, the second portion of the Stretcher unit also contains a thiol-accepting group. Suitable thiol-accepting groups include, for example, haloacetamide groups or maleimide groups having the formula

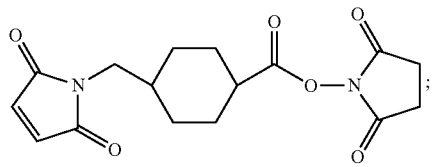

Useful Stretcher units can be obtained via commercial sources, such as Molecular Biosciences Inc. (Boulder, Colo.), or as shown below. In addition, Stretcher units can be prepared as summarized in Scheme 3 below. Scheme 3 illustrates a general synthesis of an illustrative Stretcher units unit containing a maleimide Stretcher unit.

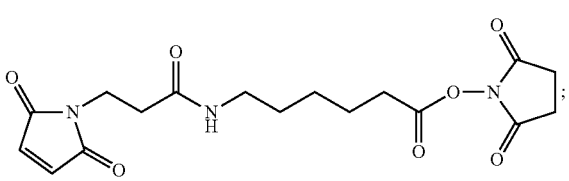

where n is an integer ranging from 1-10 and T is —H or —SO₃Na;

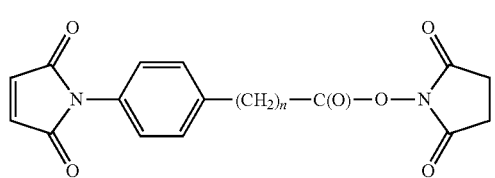

where n is an integer ranging from 0-3;

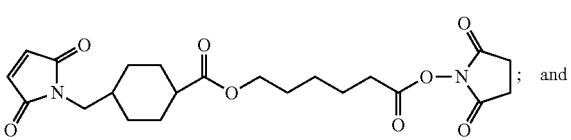

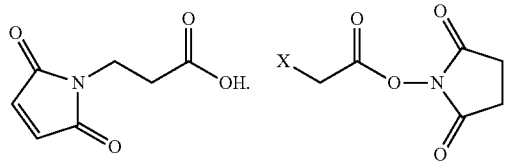

where X is —Br or —I; and

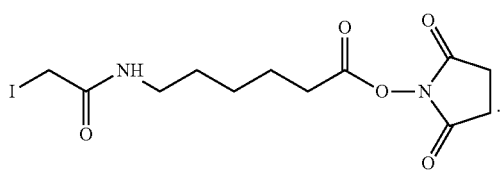 [SMILES: O=C(CI)NCCCCCC(=O)ON1C(=O)CCC1=O]

The following Scheme 3 shows methods for obtaining of a Stretcher unit containing an activated ester to react with an Amino Acid unit and having a maleimide for conjugation with a Ligand unit.

Scheme 3

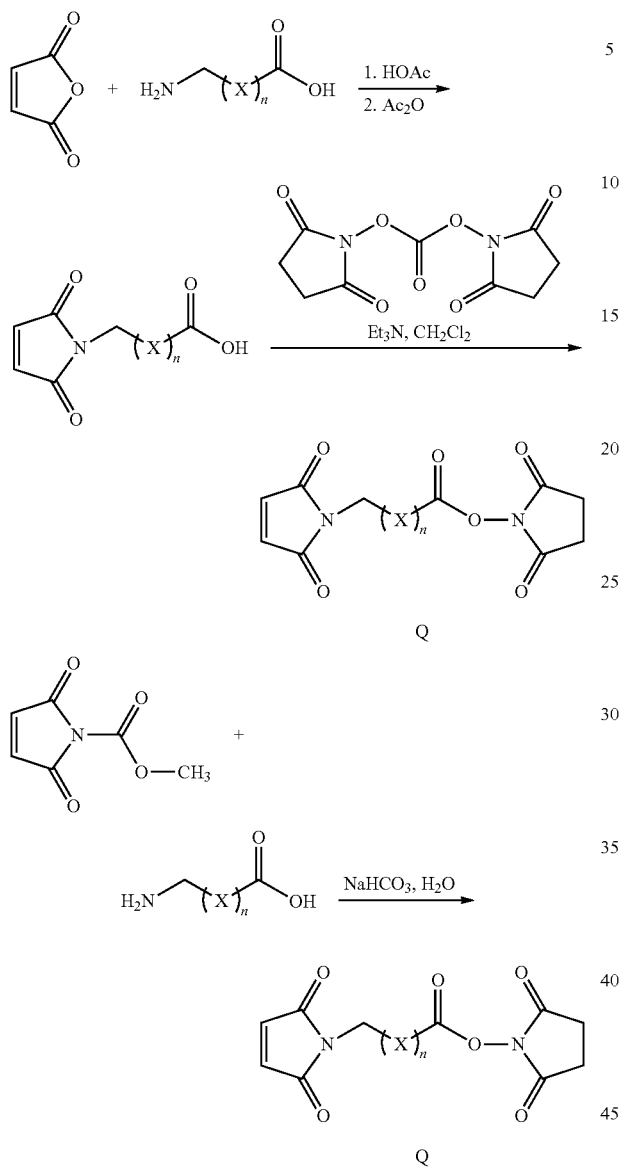

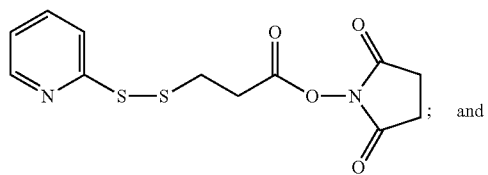

wherein X is -alkylene-, -arylene-, $C_3$-$C_8$ carbocyclo-, $C_3$-$C_8$-heterocycle-, -heteroalkylene-; and n is an integer ranging either from 0-1.

Another useful Ligand reactive Stretcher units contains activated disulfides, as shown below. They can be introduced into a Drug Linker compound by reacting the following intermediates with the amine function of the Drug Linker compound:

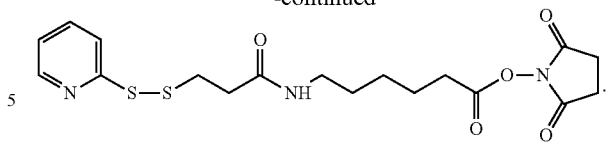

Stretcher units of formula (Va) can be introduced into a Linker unit by reacting the following intermediates with the N-terminus of an Amino Acid unit:

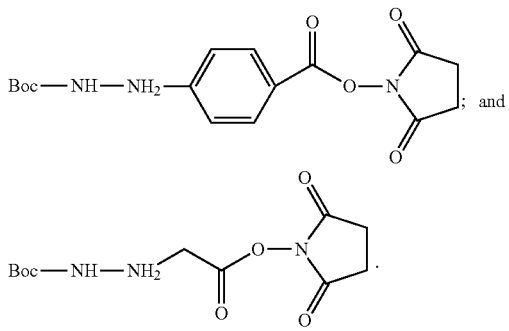

Other useful Stretchers may be synthesized according to known procedures. Aminooxy Stretchers of the formula shown below can be prepared by treating alkyl halides with N-Boc-hydroxylamine according to procedures described in Jones et al., 2000, *Tetrahedron Letters* 41(10):1531-1533; and Gilon et al., 1967, *Tetrahedron* 23(11):4441-4447. The aminooxy group reacts with a reactive group on the Ligand unit.

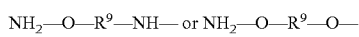

wherein —$R^9$ is selected from the group consisting of —$C_1$-$C_{10}$ alkylene-, —$C_3$-$C_8$-carbocyclo-, -arylene-, —$C_1$-$C_{30}$ heteroalkylene-, —$C_3$-$C_8$ heterocyclo-, —$C_1$-$C_{10}$ alkylene-arylene-, -arylene-$C_1$-$C_{10}$ alkylene-, —$C_1$-$C_{10}$ alkylene-($C_3$-$C_8$carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, and —($C_3$-$C_8$ heterocyclo)-$C_1$-$C_{10}$ alkylene-.

Isothiocyanate Stretchers of the formula shown below may be prepared from isothiocyanatocarboxylic acid chlorides as described in *Angew. Chem.*, 87(14):517 (1975). The isothiocyanate group reacts with a reactive group on the Ligand unit.

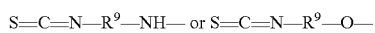

wherein —$R^9$— is as described herein.

Conjugation of Drug Linker Compounds to Ligand Units

Scheme 4 illustrates methodology useful for making Drug Linker Ligand conjugates having about 2 to about 4 drugs per Ligand unit, as exemplified by an antibody. An antibody is treated with a reducing agent, such as dithiothreitol (DTT) to reduce some or all of the interchain cysteine disulfide residues to form highly nucleophilic cysteine thiol groups (—$CH_2SH$). The partially reduced antibody thus reacts with Drug Linker compounds, or Linker unit reagents, with electrophilic functional groups such as maleimide or α-halo carbonyl, according to the conjugation method at page 766 of Klussman et al., 2004, *Bioconjugate Chemistry* 15(4):765-773.

Scheme 4

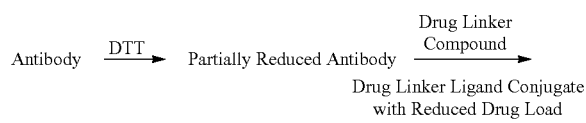

For example, an antibody, dissolved in 500 mM sodium borate and 500 mM sodium chloride at pH 8.0, is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody is dissolved in PBS and is chilled on ice. The Drug Linker compound in DMSO, dissolved in acetonitrile and water at known concentration, is added to the chilled reduced antibody in PBS. After about one hour, an excess of maleimide is added to quench the reaction and cap any unreacted antibody thiol groups. The reaction mixture is concentrated by centrifugal ultrafiltration and the ADC is purified and desalted by elution through G25 resin in PBS, filtered through 0.2 µm filters under sterile conditions, and frozen for storage.

A variety of ADCs can be prepared, with a variety of linkers and a variety of drug moieties, by following the protocols of the Examples, and characterized by HPLC and drug loading assay.

Compositions and Methods of Administration

In other embodiments, described is a pharmaceutical composition including an effective amount of a Drug Linker Ligand conjugate and/or a Drug Linker compound and a pharmaceutically acceptable carrier or vehicle. The compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a Drug Linker Ligand conjugate and/or a Drug Linker compound to be bioavailable upon administration of the composition to a patient. Compositions can take the form of one or more dosage units, where for example, a tablet can be a single dosage unit, and a container of a Drug Linker Ligand conjugate and/or a Drug Linker compound in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Drug Linker Ligand conjugate and/or a Drug Linker compound, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Drug Linker Ligand conjugate and/or a Drug Linker compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a Drug Linker Ligand conjugate and/or a Drug Linker compound such that a suitable dosage will be obtained. Typically, this amount is at least about 0.01% of a Drug Linker Ligand conjugate and/or a Drug Linker compound by weight of the composition. In an exemplary embodiment, pharmaceutical compositions are prepared so that a parenteral dosage unit contains from about 0.01% to about 2% by weight of the Drug Linker Ligand conjugate and/or a Drug Linker compound.

For intravenous administration, the composition can comprise from about 0.01 to about 100 mg of a Drug Linker Ligand conjugate and/or a Drug Linker compound per kg of the patient's body weight. In one aspect, the composition can include from about 1 to about 100 mg of a Drug Linker Ligand conjugate and/or a Drug Linker compound per kg of the patient's body weight. In another aspect, the amount administered will be in the range from about 0.1 to about 25 mg/kg of body weight of the Drug Linker Ligand conjugate and/or a Drug Linker compound.

Generally, the dosage of a Drug Linker Ligand conjugate and/or a Drug Linker compound administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The Drug Linker Ligand conjugate and/or a Drug Linker compound can be administered by any convenient route, for example by infusion or bolus injection. Administration can be systemic or local. Various delivery systems are known, e.g., encapsulation in liposomes, mieroparticles, microcapsules, capsules, etc., and can be used to administer a Drug Linker Ligand conjugate and/or a Drug Linker compound. In certain embodiments, more than one Drug Linker Ligand conjugate and/or a Drug Linker compound is administered to a patient.

In specific embodiments, it can be desirable to administer one or more Drug Linker Ligand conjugates and/or a Drug Linker compound locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the Drug Linker Ligand conjugate and/or a Drug Linker compound can be delivered in a controlled release system, such as but not limited to, a pump or various polymeric materials can be used. In yet another embodiment, a controlled-release system can be placed in proximity of the target of the Drug Linker Ligand conjugate and/or a Drug Linker compound, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Drug Linker Ligand conjugate and/or a Drug Linker compound is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the Drug Linker Ligand conjugate and/or the Drug Linker compound and pharmaceutically acceptable carriers are sterile. Water is an exemplary carrier when the Drug Linker Ligand conjugate and/or a Drug Linker compound are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the Drug Linker Ligand conjugates and/or Drug Linker compounds are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Drug Linker Ligand conjugate and/or Drug Linker compound is to be administered by infusion, it can be dispensed, for example, with an infusion bottle containing sterile pharmaceutical grade water or saline. Where the Drug Linker Ligand conjugate and/or Drug Linker compound is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer, an autoimmune disease or an infectious disease.

Therapeutics Uses of the Drug Linker Ligand Conjugates and/or Drug Linker Compounds The Drug Linker Ligand conjugates and/or Drug Linker compounds are useful for treating cancer, an autoimmune disease or an infectious disease in a patient.

Treatment of Cancer

The Drug Linker Ligand conjugates and Drug Linker compounds are useful for inhibiting the multiplication of a tumor cell or cancer cell, causing apoptosis in a tumor or cancer cell, or for treating cancer in a patient. The Drug Linker Ligand conjugates and/or Drug Linker compounds can be used accordingly in a variety of settings for the treatment of animal cancers. The Drug Linker Ligand Conjugates can be used to deliver a Drug or Drug unit to a tumor cell or cancer cell. Without being bound by theory, in one embodiment, the Ligand unit of a Drug Linker Ligand conjugate binds to or associates with a cancer-cell or a tumor-cell-associated antigen, and the Drug Linker Ligand conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, one or more specific peptide sequences within or at the Drug unit's proximal end of the Linker unit are hydrolytically cleaved by one or more tumor cell or cancer cell-associated proteases, resulting in release of the Drug unit. The released Drug unit is then free to migrate within the cell and induce cytotoxic or cytostatic activities. The Drug Linker Ligand conjugate also can be cleaved by an intracellular protease to release the Drug moiety. In an alternative embodiment, the Drug or Drug unit is cleaved from the Drug Linker Ligand conjugate outside the tumor cell or cancer cell, and the Drug or Drug unit subsequently penetrates the cell.

The Drug Linker Ligand conjugates provide conjugation-specific tumor or cancer drug targeting, thus reducing general toxicity of the Drug. The Linker units stabilize the Drug Linker Ligand conjugates in blood, yet are cleavable by tumor-specific proteases within the cell, liberating a Drug unit.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, a Drug Linker Ligand conjugate and/or Drug Linker compound having a BR96 Ligand unit can be useful for treating antigen positive carcinomas including those of the lung, breast, colon, ovaries, and pancreas. Drug Linker Ligand conjugates having an anti-CD30 or an anti-CD70 binding Ligand unit can be useful for treating hematologic malignancies.

Other particular types of cancers that can be treated with a Drug Linker Ligand conjugate and/or a Drug Linker compound include, but are not limited to, those disclosed in Table 1:

TABLE 1

| Solid tumors, including but not limited to: |
| --- |
| fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma |
| blood-borne cancers, including but not limited to: |
| acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma |
| acute and chronic leukemias: |
| lymphoblastic, myelogenous, lymphocytic, myelocytic leukemias |
| Lymphomas: |
| Hodgkin's disease, non-Hodgkin's Lymphoma, Multiple myeloma, Waldenström's macroglobulinemia, Heavy chain disease, Polycythemia vera |

Multi-Modality Therapy for Cancer

Cancers, including, but not limited to, a tumor, metastasis, or other disease or disorder characterized by uncontrolled cell growth, can be treated or inhibited by administration of a Drug Linker Ligand conjugate or Drug Linker compound.

In other embodiments, methods for treating cancer are provided, including administering to a patient in need thereof an effective amount of a Drug Linker Ligand conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Drug Linker Ligand conjugates can be administered to a patient that has also undergone surgery as treatment for the cancer.

In some embodiments, the patient also receives an additional treatment, such as radiation therapy. In a specific embodiment, the Drug Linker Ligand conjugate is administered concurrently with the chemotherapeutic agent or with radiation therapy. In another specific embodiment, the chemotherapeutic agent or radiation therapy is administered prior or subsequent to administration of a Drug Linker Ligand conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Drug Linker Ligand conjugate and/or a Drug Linker compound are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The Drug Linker Ligand conjugates and/or Drug Linker compounds can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of an Drug Linker Ligand conjugates and/or Drug Linker compound with or without accompanying high dose radiation therapy, and the stem cell graft is infused back into the animal. Supportive care is then provided while bone marrow function is restored and the patient recovers.

Treatment of Autoimmune Diseases

The Drug Linker Ligand conjugates and Drug Linker compounds are useful for killing or inhibiting the replication of a cell that produces an autoimmune disease or for treating an autoimmune disease. The Drug Linker Ligand conjugates and Drug Linker compounds can be used accordingly in a variety of settings for the treatment of an autoimmune disease in a patient. The Drug Linker Ligand conjugates can be used to deliver a Drug unit to a target cell. Without being bound by theory, in one embodiment, the Drug Linker Ligand conjugate associates with an antigen on the surface of a target cell, and the Drug Linker Ligand conjugate is then taken up inside a target-cell through receptor-mediated endocytosis. Once inside the cell, one or more specific peptide sequences within and/or Drug unit proximal to the Linker unit are enzymatically or hydrolytically cleaved, resulting in release of the Drug or Drug unit. The released Drug or Drug unit is then free to migrate in the cytosol and induce cytotoxic or cytostatic activities. The Drug Linker Ligand conjugate also can be cleaved by an intracellular protease to release the Drug or Drug moiety. In an alternative embodiment, the Drug is cleaved from the Drug Linker Ligand conjugate outside the target cell, and the Drug or Drug unit subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand unit binds to activated lymphocytes that are associated with the autoimmune disease state.

In a further embodiment, the Drug Linker Ligand conjugate or Drug Linker compound kills or inhibit the multiplication of cells that produce an autoimmune antibody associated with a particular autoimmune disease.

Particular types of autoimmune diseases that can be treated with the Drug Linker Ligand conjugates and Drug Linker compounds include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Thi lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 2.

TABLE 2

Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, Wegener's Granulomatosis Multi-Drug Therapy of Autoimmune Diseases Methods for treating an autoimmune disease are also disclosed including administering to a patient in need thereof an effective amount of a Drug Linker Ligand conjugates or Drug Linker compound and another therapeutic agent known for the treatment of an autoimmune disease.

Treatment of Infectious Diseases

The Drug Linker Ligand conjugates and Drug Linker compounds are useful for killing or inhibiting the multiplication of a cell that produces an infectious disease or for treating an infectious disease. The Drug Linker Ligand conjugates and Drug Linker compounds can be used accordingly in a variety of settings for the treatment of an infectious disease in a patient. The Drug Linker Ligand conjugates can be used to deliver a Drug unit to a target cell. In one embodiment, the Ligand unit binds to the infectious disease cell.

In one embodiment, the conjugates kill or inhibit the multiplication of cells that produce a particular infectious disease.

Particular types of infectious diseases that can be treated with the Drug Linker Ligand conjugates Conjugates include, but are not limited to, those disclosed in Table 3.

TABLE 3

Bacterial Diseases:

Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococca, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, Salmonella, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, Chlamydia, Chlamydial Pneumonia, Trachoma, Inclusion Conjunctivitis Systemic Fungal Diseases:

Histoplamosis, Coccidiodomycosis, Blastomycosis, Sporotrichosis, Cryptococcsis, Systemic Candidiasis, Aspergillosis, Mucormycosis, Mycetoma, Chromomycosis Rickettsial Diseases:

Typhus, Rocky Mountain Spotted Fever, Ehrlichiosis, Eastern Tick-Borne Rickettsioses, Rickettsialpox, Q Fever, Bartonellosis Parasitic Diseases:

Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease Viral Diseases:

Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, Smallpox

Multi-Drug Therapy of Infectious Diseases

Methods for treating an infectious disease are disclosed including administering to a patient in need thereof a Drug Linker Ligand conjugate or a Drug Linker compound and another therapeutic agent that is an anti-infectious disease agent.

The invention is further described in the following examples, which are in not intended to limit the scope of the invention.

EXAMPLES

Examples 1-9

Example 1

General Synthesis of AF-dipeptide Library by Solid Phase Synthesis—Preparation of Fmoc-AA-diaminoethane Trityl Resin (1, AA=Valine)

Reaction conditions (a): Fmoc-amino acid(2-5 equiv), HATU(2-5 equiv) or HBTU/HOBT(5 equiv), DIEA(4-10 equiv)

In a 10 ml solid phase reaction vessel (plastic syringe with PET frit) was added 1.08 g of 1,2-diaminoethane trityl resin (1.62 mmol based on the manufacturer's label), followed by a solution of 1.1 g of Fmoc-Valine (3.24 mmol), 1.24 g HATU (3.24 mmol), and 1.13 ml of DIEA (6.48 mmol) in 3 ml of DMF. The vessel was shaken for 4 h then the resin was washed 6 times each in succession with DMF, DCM and diethyl ether and dried under vacuum. Complete reaction was confirmed by a negative Kaiser test. Loading=0.5 mmol/g by Fmoc quantitation.

Example 2

Preparation of Fmoc-(D)Valine Diaminoethane Trityl Resin (1a, AA=(D)Valine)

Fmoc-(D)Valine diaminoethane trityl resin (1a) was prepared in same manner as 1. Loading=0.6 mmol/g.

Example 3

Preparation of Fmoc-Proline Diaminoethane Trityl Resin (2, AA=Proline)

Fmoc-Proline diaminoethane trityl resin (2) was prepared in same manner as 1. Loading=0.7 mmol/g.

Example 4

Preparation of Fmoc-(D)Aspartic Acid(tert-butyl)-diaminoethane Trityl Resin (3, AA=(D)Aspartic Acid(tButyl))

Fmoc-(D)Aspartic acid(tert-butyl)-diaminoethane trityl resin (3) was prepared in same manner as 1 with the following exception: HBTU/HOBT was use in place of HATU. Loading=0.6 mmol/g.

Example 5

Preparation of Fmoc-(D)Lysine(boc)-diaminoethane Trityl Resin (4, AA=(D)Lysine(boc))

Fmoc-(D)Lysine(boc)-diaminoethane trityl resin (4) was prepared in the same manner as 1. Loading=0.6 mmol/g.

Example 6

Preparation of Fmoc-Lysine(boc)-diaminoethane Trityl Resin (4a, AA=Lysine(boc))

Fmoc-Lysine(boc)-diaminoethane trityl resin (4a) was prepared in the same manner as 1. Loading=0.6 mmol/g.

Example 7

Preparation of Fmoc-Asparagine(trityl)-diaminoethane Trityl Resin (4b, AA=Asparagine)

Fmoc-Asparagine(trityl)-diaminoethane trityl resin (4b) was prepared in the same manner as 1. Loading=0.5 mmol/g.

Example 8

Preparation of Fmoc-Methionine Diaminoethane Trityl Resin (4c, AA=Methionine)

Fmoc-Methionine diaminoethane trityl resin (4c) was prepared in the same manner as 1. Loading=0.6 mmol/g.

Example 9

Preparation of Fmoc-(D)Methionine Diaminoethane Trityl Resin (4d, AA=(D)Methionine)

Fmoc-(D)Methionine diaminoethane trityl resin (4d) was prepared in the same manner as 1. Loading=0.5 mmol/g.

Examples 10-32

General Preparation of AF-AA1-AA2-diaminoethane-propionyl-1-maleimide (Examples 10-32) by a Combination of Solid and Solution Phase Synthesis

Example 10

AF-Aspartic Acid-Valine-diaminoethane-propionyl-maleimide (5a, AA1-AA2=Aspartic Acid-Valine)

-continued

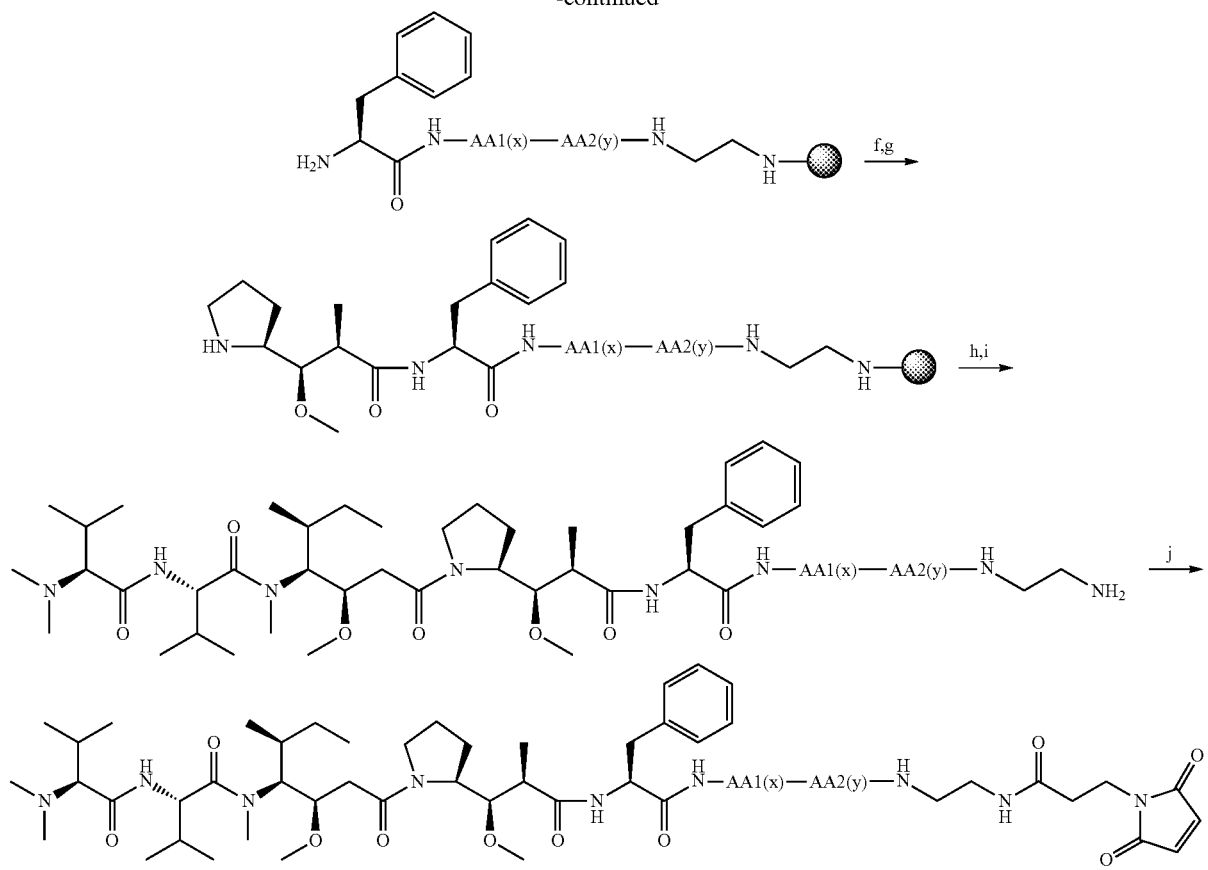

Reaction conditions (a): 20% piperidine/DMF, (b) Fmoc-amino acid (2-5 equiv), HATU (2-5 equiv), and DIEA (4-10 equiv), (c) 20% piperidine/DMF, (d) Fmoc-Phe (2 equiv), HATU (2 equiv), and DIEA (4 equiv), (e) 20% piperidine/DMF, (f) Fmoc-Dap (2 equiv.), HATU (2 equiv), and DIEA (4 equiv), (g) 20% piperidine/DMF, (h) Dov-Val-Dil-OH (2 equiv.), HATU (2 equiv), and DIEA (4 equiv), (i) 95% TFA/dichloromethane, (J) BMPS (2 equiv), DIEA (2 equiv).

200 mg of resin 1 (0.1 mmol) in a 10 mL syringe with a PET frit was treated with a solution of 20% piperidine in DMF (3 mL) and shaken for 1 h, and then washed 6 times each in succession with DMF, DCM and diethyl ether and dried in vacuo for 2 h. A solution of Fmoc-Asp(OtBu)-OH (82 mg, 0.2 mmol), HATU (76 mg, 0.2 mmol) and DIEA (70 µL, 0.4 mmol) in anhydrous DMF (4 mL) was then added to the resin which was shaken for 4 h, washed 6 times each in succession with DMF, DCM and diethyl ether, and dried in vacuo for 2 h. A 20% piperidine in DMF solution (3 mL) was added to the syringe, and the mixture was agitated for 2 h. The resin was then filtered, washed 6 times each in succession with DMF, DCM and diethyl ether, and dried in vacuo for 2 h. In a separate flask Fmoc-Phe (0.2 mmol) and HATU (0.2 mmol) were dissolved in anhydrous DMF (4 mL) followed by the addition of DIEA (0.4 mmol). The solution was then transferred to the syringe containing the resin, and the mixture was agitated for 4 h. LCMS analysis of material cleaved from a small amount of resin was used to determine reaction completion. The resin was filtered, washed 6 times each in succession with DMF, DCM and diethyl ether, and dried in vacuo for 2 h. In this manner, after Fmoc deprotection with 20% piperidine in DMF, Fmoc-Dap was coupled, followed by one more Fmoc deprotection and final Dov-Val-Dil-OH coupling. The resin was then treated with a solution of 95% TFA/dichloromethane (3 mL), and washed an additional 3 times with 95% TFA/dichloromethane (3 mL). The combined filtrate was allowed to stand at room temperature for 30 min, than concentrated to dryness. Half of this material (0.05 mmol) and 3-maleimidopropionic acid NHS ester (25 mg, 0.1 mmol) were dissolved in dichloromethane (1 mL) with DIEA (70 µL, 0.1 mmol) and stirred at room temp for 4 h. Solvent was removed in vacuo and the product purified by reverse phase preparative HPLC. Yield: 15 mg (26%) of white solid. RP-HPLC analysis: >90% at 6.95 min; ESMS m/z=1153.50 (M+H)$^+$, Example 11

Preparation of AF-Isoleucine-Valine-diaminoethane-propionyl-maleimide (5b, AA1-AA2=Isoleucine-Valine)

AF-Isoleucine-Valine-diaminoethane-propionyl-maleimide (5b) was prepared in the same manner as 5a, using Fmoc-Ile as AA1. Yield: 21 mg (33%) of white solid. RP-HPLC analysis: >95% at 9.2 min; ESMS m/z=1151.68 (M+H)$^+$.

Example 12

Preparation of AF-Asparagine-Valine-diaminoethane-propionyl-maleimide (5c, AA1-AA2=Asparagine-Valine)

AF-Asparagine-Valine-diaminoethane-propionyl-maleimide (5c) was prepared in the same manner as 5a using Fmoc-Asn(trt), but the material cleaved from the resin was purified by preparative HPLC prior to coupling with 3-maleimidopropionic acid NHS ester. Yield: 56 mg (63%) of white solid. RP-HPLC analysis: >95% at 8.5 min; ESMS m/z=1152.96 (M+H)$^+$.

Example 13

Preparation of AF-Tyrosine-Valine-diaminoethane-propionyl-maleimide (5d, AA1-AA2=Tyrosine-Valine)

AF-Tyrosine-Valine-diaminoethane-propionyl-maleimide (5d) was prepared in the same manner as 5c, using Fmoc-Tyr for AA1. Yield: 36 mg (68%) of white solid. RP-HPLC analysis: >95% at 7.8 min; ESMS m/z=1201.67 (M+H)$^+$.

Example 14

Preparation of AF-Trimethyllysine-Proline-diaminoethane-propionyl-maleimide (6a, AA1-AA2=Trimethyllysine-Proline)

AF-Trimethyllysine-Proline-diaminoethane-propionyl-maleimide (6a) was prepared by the same procedure as 5a starting with 284 mg Fmoc-proline-diaminoethane-trityl resin (2) and using Fmoc-trimethyllysine as AA1. Yield: 6 mg (21%). ESMS m/z=1207.027 (M+H)$^+$.

Example 15

Preparation of AF-Isoleucine-Proline-diaminoethane-propionyl Maleimide (6b, AA1-AA2=Isoleucine-Proline)

AF-Isoleucine-Proline-diaminoethane-propionyl maleimide (6b) was prepared using the same method as 5a starting with 378 mg of Fmoc-proline-diaminoethane-trityl resin (2) and using Fmoc-Ile as AA1. Yield: 36 mg (19%) of white solid. RP-HPLC analysis: >95% at 9.2 min; ESMS m/z=1149.379 (M+H)$^+$.

Example 16

Preparation of AF-Asparagine-Proline-diaminoethane-propionyl Maleimide (6c, AA1-AA2=Asparagine-Proline)

AF-Asparagine-Proline-diaminoethane-propionyl maleimide (6c) was prepared using the same method as 5c starting with 150 mg of Fmoc-proline-diaminoethane-trityl resin (2) and using Fmoc-Asn as AA1. Yield: 21.8 mg (19%) of white solid. RP-HPLC analysis: >95% at 10.95 min; ESMS m/z=1150.320 (M+H)$^+$.

Example 17

Preparation of AF-Methionine-Proline-diaminoethane-propionyl Maleimide (6d, AA1-AA2=Methionine-Proline)

AF-Methionine-Proline-diaminoethane-propionyl maleimide (6d) was prepared using the same method as 5a starting with 150 mg of Fmoc-proline-diaminoethane-trityl resin (2) and using Fmoc-Met as AA1. Yield: 20.6 mg (18.4%) of white solid. RP-HPLC analysis: >95% at 11.2 min; ESMS m/z=1167.047 (M+H)$^+$.

Example 18

Preparation of AF-Tyrosine-(D)Aspartic Acid-Diaminoethane-Propionyl Maleimide (7a, AA1-AA2=Tyrosine-(D)Aspartic Acid)

AF-Tyrosine-(D)Aspartic Acid-diaminoethane-propionyl maleimide (7a) was prepared using the same method as 5c starting with 224 mg of Fmoc-(D)Asp(OtBu)-diaminoethane-trityl resin (3), and using Fmoc-Tyr(OtBu) as AA1. Yield: 19 mg (11%) of white solid. RP-HPLC analysis: >90% at 6.2 min; ESMS m/z=1217.789 (M+H)$^+$.

Example 19

Preparation of AF-Norvaline-(D)Aspartic Acid-diaminoethane-propionyl Maleimide (7b, AA1-AA2=Norvaline-(D)Aspartic Acid)

AF-Norvaline-(D)Aspartic Acid-diaminoethane-propionyl maleimide (7b) was prepared using the same method as 5c starting with Fmoc-(D)Asp(OtBu)-diaminoethane-trityl resin (3) and using Fmoc-NVal as AA1. Yield 10 mg (6%). RP-HPLC analysis: >95% at 6.3 min; ESMS m/z=1153.955 (M+H)$^+$.

Example 20

Preparation of AF-β-alanine-(D)Aspartic Acid-diaminoethane-propionyl Maleimide (7c, AA1-AA2=(β-alanine-(D)Aspartic Acid)

AF-β-alanine-(D)Aspartic Acid-diaminoethane-propionyl maleimide (7c) was prepared using the same method as 5c starting with 198 mg of Fmoc-(D)Asp(OtBu)-diaminoethane-trityl resin (3), and using Fmoc-β-Ala as AA1. Yield: 12 mg (8%) of white solid. RP-HPLC analysis: >95% at 6.3 min; ESMS m/z=1125.709 (M+H)$^+$.

Example 21

Preparation of AF-Methionine-(D)Aspartic Acid-diaminoethane-propionyl Maleimide (7d, AA1-AA2=Methionine-(D)Aspartic Acid)

AF-Methionine-(D)Aspartic Acid-diaminoethane-propionyl maleimide (7d) was prepared using the same method as 5c starting with 100 mg of Fmoc-(D)Asp(OtBu)-diaminoethane-trityl resin (3), and using Fmoc-Met as AA1. Yield: 19.4 mg (25%) of white solid. RP-HPLC analysis: >95% at 10.97 min; ESMS m/z=1185.195 (M+H)$^+$.

Example 22

Preparation of AF-Homo-β-Phenylalanine-(D)Aspartic Acid-diaminoethane-propionyl Maleimide (7e, AA1-AA2=Homo-β-Phenylalanine-(D)Aspartic Acid)

AF-Homo-β-Phenylalanine-(D)Aspartic Acid-diaminoethane-propionyl maleimide (7e) was prepared using the same method as 5c starting with 100 mg of Fmoc-(D)Asp(OtBu)-diaminoethane-trityl resin (3), and using Fmoc-hPhe as AA1. Yield: 19.10 mg (24%) of white solid. RP-HPLC analysis: >90% at 10.85 min; ESMS=1167.075 (M+H)$^+$.

Example 23

Preparation of AF-Asparagine-(D)Aspartic Acid-diaminoethane-propionyl Maleimide (7f, AA1-AA2=Asparagine-(D)Aspartic Acid)

AF-Asparagine-(D)Aspartic Acid-diaminoethane-propionyl maleimide (7f) was prepared using the same method as 5c starting with 100 mg of Fmoc-(D)Asp(OtBu)-diaminoethane-trityl resin (3), and using Fmoc-Asn(trt) as AA1. Yield: 38 mg (49%) of white solid. RP-HPLC analysis: >90% at 10.85 min; ESMS m/z=1167.075 (M+H)$^+$.

Example 24

Preparation of AF-Proline-(D)Lysine-diaminoethane-propionyl Maleimide (8a, AA1-AA2=Proline-(D)Lysine)

AF-Proline-(D)Lysine-diaminoethane-propionyl maleimide (8a) was prepared in the same manner as 5a, starting with Fmoc-(D)-Lysine(boc)-diaminoethane trityl resin (4) and Fmoc-Proline for AA1, but only 30% HFIP (hexafluoroisopropanol) in dichloromethane was used to cleave the penultimate diaminoethane-peptide from the resin in order to preserve the boc protecting group on the lysine. After coupling to maleimidopropionic acid NHS ester, the boc group was removed by treatment with 1:1 TFA/dichloromethane (1 mL) and the product was isolated by preparative HPLC. Yield: 33 mg (40%) of white solid; ESMS m/z=1181.720 (M+H)$^+$.

Example 25

Preparation of AF-Phenylglycine-(D)Lysine-diaminoethane-propionyl Maleimide (8b, AA1-AA2=Phenylglycine-(D)Lysine)

AF-Phenylglycine-(D)Lysine-diaminoethane-propionyl maleimide (8b) was prepared in the same manner as 8a, starting with 232 mg of Fmoc-(D)-Lysine(boc)-diaminoethane trityl resin (4), and using Fmoc-Phg for AA1. Yield: 10 mg (11%) of white solid. RP-HPLC analysis: >90% at 10.21 min; ESMS m/z=1200.656 (M+H)$^+$.

Example 26

Preparation of AF-Methionine-(D)Lysine-diaminoethane-propionyl Maleimide (8c, AA1-AA2=Methionine-(D)Lysine)

AF-Methionine-(D)Lysine-diaminoethane-propionyl maleimide (8c) was prepared in the same manner as 8a, starting with 236 mg of Fmoc-(D)-Lysine(boc)-diaminoethane trityl resin (4), and using Fmoc-Met for AA1. Yield: 46 mg (49%) of white solid. RP-HPLC analysis: >90% at 10.48 min; ESMS m/z=1198.804 (M+H)$^+$.

Example 27

Preparation of AF-Asparagine-(D)Lysine-Diaminoethane-Propionyl Maleimide (8d, AA1-AA2=Asparagine-(D)Lysine)

AF-Asparagine-(D)Lysine-diaminoethane-propionyl maleimide (8d) was prepared in the same manner as 8a, starting with 236 mg of Fmoc-(D)-Lysine(boc)-diaminoethane trityl resin (4), and using Fmoc-Asn(trt) for AA1. After coupling to maleimidopropionic acid NHS ester, the side chain protecting groups were removed by treatment with 95% TFA/dichloromethane (1 ml) for 1 h, and then the product was isolated by preparative HPLC. Yield: 64 mg (62%) of white solid. RP-HPLC analysis: >95% at 10.34 min; ESMS m/z=1181.699 (M+H)$^+$.

Example 28

Preparation of AF-Glutamine-(D)Lysine-Diaminoethane-Propionyl Maleimide (8e, AA1-AA2=Glutamine-(D)Lysine)

AF-Glutamine-(D)Lysine-diaminoethane-propionyl maleimide (8e) was prepared in the same manner as 8a, starting with 98 mg of Fmoc-(D)-Lysine(boc)-diaminoethane trityl resin (4), and using Fmoc-Gln for AA1. Yield: 15 mg (19.7%) of white solid. RP-HPLC analysis: >90% at 10.07 min; ESMS m/z=1195.813 (M+H)$^+$.

Example 29

Preparation of AF-Arginine-(D)Lysine-diaminoethane-propionyl Maleimide (8f, AA1-AA2=Arginine-(D)Lysine)

AF-Arginine-(D)Lysine-diaminoethane-propionyl maleimide (8f) was prepared in the same manner as 8a, starting with 101 mg of Fmoc-(D)-Lysine(boc)-diaminoethane trityl resin (4), and using Fmoc-Arg(Pbf) for AA1. Yield: 13 mg (18%). RP-HPLC analysis: >95% purity by peak area at 9.80 min; ESMS=1223.908 (M+H)$^+$.

Example 30

Preparation of AF-Citrulline-(D)Lysine-diaminoethane-propionyl Maleimide (8g, AA1-AA2=Citrulline-(D)Lysine)

AF-Citrulline-(D)Lysine-diaminoethane-propionyl maleimide (8g) was prepared in the same manner as 8a, starting with 102 mg of Fmoc-(D)-Lysine(boc)-diaminoethane trityl resin (4), and using Fmoc-Cit for AA1. Yield: 26 mg (33%) of white solid. RP-HPLC analysis: >95% purity at 10.45 min; ESMS m/z=1223.933 (M+H)$^+$.

Example 31

Preparation of AF-Tyrosine-(D)Lysine-diaminoethane-propionyl Maleimide (8h, AA1-AA2=Tyrosine-(D)Lysine)

AF-Tyrosine-(D)Lysine-diaminoethane-propionyl maleimide (8h) was prepared in the same manner as 8a, starting with 101 mg of Fmoc-(D)-Lysine(boc)-diaminoethane trityl resin (4), and using Fmoc-Tyr(OtBu) for AA1. Yield: 26 mg (34%) of white solid. RP-HPLC analysis: >95% at 10.05 min; ESMS m/z=1230.707 (M+H)$^+$.

Example 32

Preparation of AF-Lysine-(D)Lysine-diaminoethane-propionyl Maleimide (8i, AA1-AA2=Lysine-(D)Lysine)

AF-Lysine-(D)Lysine-diaminoethane-propionyl maleimide (8i) was prepared in the same manner as 8a, starting with 106 mg of Fmoc-(D)-Lysine(boc)-diaminoethane trityl resin (4), and using Fmoc-Lys for AA1. Yield: 13.6 mg (34%). RP-HPLC analysis: >90% at 11.32 min; ESMS m/z=1281.238 (M+H)$^+$.

General Example 33

General Preparation of AF-AA1-AA2-AA3-diaminoethane-propionyl-1-maleimide (34-35) by a Combination of Solid and Solution Phase Synthesis Drug Linkers containing more that 2 amino acids in the Linker unit were prepared as described in Example 10 by incorporating additional steps (b) and (c) with an additional Fmoc-AA1.

Example 34

Preparation of AF-Asparagine -(D)Lysine-(D)Lysine-diaminoethane-propionyl Maleimide (8j, AA1-AA2-AA3=Asparagine-(D)Lysine-(D)Lysine)

AF-Asparagine-(D)Lysine-(D)Lysine-diaminoethane-propionyl maleimide (8j) was prepared in the same manner as 8a, as described in Example 33, starting with 102 mg of Fmoc-(D)-Lysine(boc)-diaminoethane trityl resin (4), and using Fmoc-(D)Lys for AA2 and Fmoc-Asn(trt) for AA1. Yield: 20.5 mg (23%) of white solid. RP-HPLC analysis: >90% at 10.41 min; ESMS m/z=1309.320 (M+H)$^+$.

Example 35

Preparation of AF-Methionine-(D)Lysine-(D)Lysine-diaminoethane-propionyl Maleimide (8k, AA1-AA2-AA3=Methionine-(D)Lysine-(D)Lysine)

AF-Methionine-(D)Lysine-(D)Lysine-diaminoethane-propionyl maleimide (8k) was prepared in the same manner as 8a, as described in Example 33, starting with 107 mg of Fmoc-(D)-Lysine(boc)-diaminoethane trityl resin (4), and using Fmoc-(D)Lys for AA2 and Fmoc-Met for AA1. Yield: 22 mg (24%) of white solid. RP-HPLC analysis: >90% at 10.33 min; ESMS m/z=1326.008 (M+H)$^+$.

Examples 36-38

Example 36

Preparation of MMAF-AA1-AA2-diaminoethane-propionyl Maleimide

Monomethyl versions of Auristatin F (MMAF) Drug Linkers were prepared by substituting in step (h) of Example 10 Fmoc-MeVal-Val-Dil-OH for Dov-Val-Dil-OH with. Fmoc was removed by 20% piperidine/DMF treatment, prior to cleaving the compound off the resin (step i).

Example 37

Preparation of MMAF-Methionine-(D)Lysine-diaminoethane-propionyl Maleimide (8l, AA1-AA2=Methionine-(D)Lysine)

MMAF-Methionine-(D)Lysine-diaminoethane-propionyl maleimide (8l) was prepared in the same manner as 8a as described in Example 36, starting with 179 mg of Fmoc-(D)-Lysine(boc)-diaminoethane trityl resin (4), and using Fmoc-Met for AA1. Fmoc-MeVal-Val-Dil was used in place of Dov-Val-Dil, and the Fmoc was removed with 20% piperidine/DMF prior to cleavage of the resin. Yield: 30.6 mg (22%) of white solid. RP-HPLC analysis: >90% at 10.69 min; ESMS m/z=1184.554 (M+H)$^+$.

Example 38

Preparation of MMAF-Asparagine-(D)Lysine-Diaminoethane-Propionyl Maleimide (8m, AA1-AA2=Asparagine-(D)Lysine)

MMAF-Asparagine-(D)Lysine-diaminoethane-propionyl maleimide (8m) was prepared in the same manner as 8l as described in Example 36, starting with 144 mg of Fmoc-(D)-Lysine(boc)-diaminoethane trityl resin (4), and using Fmoc-Asn(trt) for AA1. Yield: 19.2 mg (16%) of white solid. RP-HPLC analysis: >90% purity at 19.2 min; ESMS m/z=1167.169 (M+H)$^+$.

Examples 39-42

Example 39

Preparation of AF-Methionine-(L)Lysine-diaminoethane-propionyl maleimide (8n, AA1-AA2=Methionine-(L)Lysine)

AF-Methionine-(L)Lysine-diaminoethane-propionyl maleimide (8n) was prepared in the same manner as 8a, starting with 168 mg of Fmoc-(L)-Lysine(boc)-diaminoethane trityl resin (4a), and using Fmoc-Met for AA1. Yield: 22.1 mg (15.3%) of white solid. RP-HPLC analysis: >90% at 10.42 min; ESMS m/z=1181.985 (M+H)$^+$.

Example 40

Preparation of AF-Asparagine-(L)Lysine-diaminoethane-propionyl Maleimide (8o, AA1-AA2=Asparagine-(L)Lysine)

AF-Asparagine-(L)Lysine-diaminoethane-propionyl maleimide (8o) was prepared in the same manner as 8a, starting with 146 mg of Fmoc-(L)-Lysine(boc)-diaminoethane trityl resin (4a), and using Fmoc-Asn(trt) for AA1. Yield: 19.9 mg (16%). RP-HPLC analysis: >90% at 10.32 min; ESMS m/z=1198.985 (M+H)$^+$.

Example 41

Preparation of AF-Methionine-(D)Methionine-diaminoethane-propionyl Maleimide (8r, AA1-AA2=Methionine-(D)Methionine)

AF-Methionine-(D)Methionine-diaminoethane-propionyl maleimide (8r) was prepared in the same manner as 5c, starting with 146 mg of Fmoc-(D)Methionine-diaminoethane trityl resin (4d), and using Fmoc-Met for AA1. Yield: 6 mg (6.3%). RP-HPLC analysis: >90% at 11.45 min; ESMS m/z=1201.172 (M+H)$^+$.

Example 42

Preparation of AF-Methionine-(D)Valine-diaminoethane-propionyl Maleimide (8s, AA1-AA2=Methionine-(D)Valine)

AF-Methionine-(D)Valine-diaminoethane-propionyl maleimide (8s) was prepared in the same manner as 5c, starting with 156 mg of Fmoc-(D)Valine-diaminoethane trityl resin (1a), and using Fmoc-Met for AA1. Yield: 13 mg (13%). RP-HPLC analysis: >90% at 11.18 min; ESMS m/z=1169.52 $(M+H)^+$.

Examples 43-45

Example 43

Preparation of AF-AA1-diaminoethane-propionyl maleimide

AF-AA1-diaminoethane-propionyl maleimide was prepared as described in Example 10 by omitting steps (b) and (c).

Example 44

Preparation of AF-Asparagine-diaminoethane-propionyl Maleimide (8p, AA1-Asparagine)

AF-Asparagine-diaminoethane-propionyl maleimide (8p) was prepared in the same manner as 5c, as modified in Example 43, starting with 217 mg of Fmoc-Asparagine(trt)-diaminoethane trityl resin (4b). Yield: 22.9 mg (18%). RP-HPLC analysis: >90% at 10.85 min; ESMS m/z=1053.838 $(M+H)^+$.

Example 45

Preparation of AF-Methionine-diaminoethane-propionyl Maleimide (8q, AA1-Asparagine)

AF-Methionine-diaminoethane-propionyl maleimide (8q) was prepared in the same manner as 5; as modified in Example 43, starting with 177 mg of Fmoc-Methionine-diaminoethane trityl resin (4c). Yield: 19.6 mg (15.5%). RP-HPLC analysis: >90% at 10.6 min; ESMS m/z=1070.594 $(M+H)^+$.

Examples 46-54

Example 46

Preparation of Other Auristatin-AA1-AA2-diaminoethane-propionyl Maleimides

Auristatins containing amino acids other than phenylalanine at the C-terminus were prepared using correspondent Fmoc-amino acid in step (d) of Example 10 (or Example 24, if resin 4 is used). For example, Fmoc-Phenylalanine for auristatin F (AF) can be replaced with Fmoc-Methionine for auristatin M (AM) or Fmoc-Tryptophan for auristatin W (AW).

Example 47

Preparation of AM-Tyrosine-(D)Aspartic Acid-diaminoethane-propionyl Maleimide (9a, AA1-AA2=Tyrosine-(D)Aspartic Acid)

AM-Tyrosine-(D)Aspartic Acid-diaminoethane-propionyl maleimide (9a) was prepared in the same manner as 8a, starting with 100 mg of Fmoc-(D)Asp(OtBu)-diaminoethane trityl resin (3), and using Fmoc-Tyrosine(tBu) for AA1 and Fmoc-Methionine as Fmoc-NH—CH(X)—COOH in step (d). Yield: 16.6 mg. RP-HPLC analysis: >90% at 10.35 min; ESMS m/z=1201.430 $(M+H)^+$.

Example 48

Preparation of AM-Methionine-(D)Lysine-diaminoethane-propionyl Maleimide (9b, AA1-AA2=Methionine-(D)Lysine)

AM-Methionine-(D)Lysine-diaminoethane-propionyl maleimide (9b) was prepared in the same manner as 9a, starting with 100 mg of Fmoc-(D)Lys(Boc)-diaminoethane trityl resin (4), and using Fmoc-Methionine for AA1 and Fmoc-Methionine as Fmoc-NH—CH(X)—COOH. A solution of 30% HFIP in dichloromethane was used to cleave the penultimate diaminoethane-peptide from the resin in order to preserve the boc protecting group on the lysine. After coupling to maleimidopropionic acid NHS ester, the boc group was removed by treatment with 1:1 TFA/dichloromethane (1 ml) and the product was isolated by preparative HPLC. Yield: 18.5 mg. RP-HPLC analysis: >90% at 10.05 min; ESMS m/z=1182.555 $(M+H)^+$.

Example 49

Preparation of AM-Asparagine-(D)Lysine-diaminoethane-propionyl Maleimide (9c, AA1-AA2=Asparagine-(D)Lysine)

AM-Asparagine-(D)Lysine-diaminoethane-propionyl maleimide (9c) was prepared in the same manner as 9a, starting with 100 mg of Fmoc-(D)Lys(Boc)-diaminoethane trityl resin (4), and using Fmoc-Methionine for AA1 and Fmoc-Methionine as Fmoc-NH—CH(X)—COOH. Yield: 8.9 mg. RP-HPLC analysis: >95% at 9.89 min; ESMS m/z=1165.818 $(M+H)^+$.

Example 50

Preparation of AM-Asparagine-diaminoethane-propionyl Maleimide (9d, AA1=Asparagine)

AM-Asparagine-diaminoethane-propionyl maleimide (9d) was obtained as a side product during synthesis of 9c due to inefficient coupling of Fmoc-(D)Lysine to 1,2-diaminoethane trityl resin. Yield: 5.2 mg. RP-HPLC analysis: >95% at 10.32 min; ESMS m/z=1037.581 $(M+H)^+$.

Example 51

Preparation of AW-Tyrosine-(D)Aspartic Acid-diaminoethane-propionyl Maleimide (10a, AA1-AA2=Tyrosine-(D)Aspartic Acid)

AW-Tyrosine-(D)Aspartic acid-diaminoethane-propionyl maleimide (10a) was prepared in the same manner as 9a, starting with 100 mg of Fmoc-(D)Asp(OtBu)-diaminoethane trityl resin (3), and using Fmoc-Tyrosine for AA1 and Fmoc-Tryptophan(Boc) as Fmoc-NH—CH(X)—COOH. Yield: 19.7 mg. RP-HPLC analysis: >97% at 10.85 min; ESMS m/z=1256.840 (M+H)$^+$.

Example 52

Preparation of AW-Methionine-(D)Lysine-Diaminoethane-Propionyl Maleimide (10b, AA1-AA2=Methionine-(D)Lysine)

AW-Methionine-(D)Lysine-diaminoethane-propionyl maleimide (10b) was prepared in the same manner as 9a, starting with 100 mg of Fmoc-(D)Lys(Boc)-diaminoethane trityl resin (4), and using Fmoc-Methionine for AA1 and Fmoc-Tryptophan(Boc) as Fmoc-NH—CH(X)—COOH. A solution of 30% HFIP in dichloromethane was used to cleave the penultimate diaminoethane-peptide from the resin in order to preserve the boc protecting group on the lysine. After coupling to maleimidopropionic acid, the Boc group was removed by treatment with 1:1 TFA/dichloromethane (1 ml) and the product was isolated by preparative HPLC. Yield: 21 mg. RP-HPLC analysis: >97% at 10.25 min; ESMS m/z=1238.043 (M+H)$^+$.

Example 53

Preparation of AW-Asparagine-(D)Lysine-diaminoethane-propionyl maleimide (10c, AA1-AA2=Asparagine-(D)Lysine)

AW-Asparagine-(D)Lysine-diaminoethane-propionyl maleimide (10c) was prepared in the same manner as 9a, starting with 100 mg of Fmoc-(D)Lys(Boc)-diaminoethane trityl resin (4), and using Fmoc-Asparagine(OtBu) for AA1 and Fmoc-Tryptophan(Boc) as Fmoc-NH—CH(X)—COOH. Yield: 16 mg. RP-HPLC analysis: >97% at 10.0 min; ESMS m/z=611.098 (M+H)$^+$.

Example 54

Preparation of AW-Asparagine-diaminoethane-propionyl Maleimide (10d, AA1=Asparagine)

AW-Asparagine-diaminoethane-propionyl maleimide (10d) was prepared in the same manner as 10c due to inefficient coupling of Fmoc-(D)Lys(Boc) to 1,2-diaminoethane trityl resin. Yield: 12.4 mg. RP-HPLC analysis: >95% at 10.51 min; ESMS m/z=1097.740 (M+H)$^+$.

Example 55

Preparation of Dov-Val-Dil-Dap-Phe (AF)

A mixture of Fmoc-Dap (986 mg, 2.4 mmol), HATU (846 mg, 2.4 mmol) and DIEA (842 µL, 4.8 mmol) in DMF (20 mL) was added to a 50 mL vessel containing phenylalanine bound to 2-chlorotrityl resin (3.0 g, 2.4 mmol), and the mixture was vigorously shaken for 16 h at room temperature. Reaction completion was confirmed by negative Kaiser test, and correct product confirmed by LCMS (m/z=410.39). Resin was rinsed 6 times each in succession with DMF, CH$_2$Cl$_2$, and ethyl ether, and dried under high vacuum. The above resin was treated with 20 mL of a 20% piperidine/DMF solution and shaken vigorously for 2 h. The resin was rinsed 6 times each in succession with DMF, CH$_2$Cl$_2$, and ethyl ether, and dried under high vacuum. A mixture of Dov-Val-Dil-OH (2.4 mmol), HATU (864 mg 2.4 mmol) and DIEA (873 µL, 5 mmol) in DMF (20 mL) was added, and the reaction vessel was shaken for 16 h. The resin was rinsed 6 times each in succession with DMF, CH$_2$Cl$_2$, and ethyl ether, and dried under high vacuum. The product was cleaved from resin with a 2% TFA/CH$_2$Cl$_2$ solution and purified by reverse phase preparative HPLC. Yield: 1.6 g (89%). MS m/z=746.59.

Example 56

General Preparation of Auristatin-Peptide Antibody Conjugates

Antibody (e.g., AC10 or 1F6), dissolved in 500 mM sodium borate and 500 mM sodium chloride at pH 8.0, is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The Drug Linker compound reagent, auristatin-amino acid(s)-diaminoethane-propionyl maleimide (Auristatin-Peptide), dissolved in DMSO, is diluted in acetonitrile and water at known concentration, and added to the chilled reduced antibody in PBS. After about one hour, an excess of maleimide is added to quench the reaction and cap any unreacted antibody thiol groups. The reaction mixture is concentrated by centrifugal ultrafiltration and the Auristatin-Peptide-Antibody conjugate is purified and desalted by elution through G25 resin in PBS, filtered through 0.2 µm filters under sterile conditions, and frozen for storage.

Following this procedure, Auristatin-Peptide-Antibody Conjugates were prepared using antibody humanized 1F6 (see, e.g., International Patent Publication WO 06/113909, for a description of humanized 1F6).

Example 57

Determination of Cytotoxicity of Selected Compounds

The cytotoxic activity of Auristatin-Peptide-Antibody conjugates is evaluated on CD70$^+$ positive cell lines, for example, 786-O, a renal cell carcinoma; Caki-1, a renal cell carcinoma; L428, a Hodgkin's disease cell line; UMRC-3, a renal cell carcinoma; LP-1, a human myeloma cell line; and U251, a glioblastoma cell line. In addition, a CD70$^-$ cell line, such as HCT-116, is used as a control. To evaluate the cytotoxicity of compounds, cells can be seeded at approximately 5-10,000 per well in 150 µl of culture medium, then treated with graded doses of compounds in quadruplicates at the initiation of the assay. Cytotoxicity assays are usually carried out for 96 hours after addition of test compounds. Fifty µl of resazurin dye may be added to each well during the last 4 to 6 hours of the incubation to assess viable cells at the end of culture. Dye reduction can be determined by fluorescence spectrometry using the excitation and emission wavelengths of 535 nm and 590 nm, respectively. For analysis, the extent of resazurin reduction by the treated cells can be compared to that of the untreated control cells.

In Vitro Cell Proliferation Assay

The efficacy of a conjugate can be measured by a cell proliferation assay employing the following protocol (Promega Corp. Technical Bulletin TB288; Mendoza et al., 2002, *Cancer Res.* 62:5485-5488):
1. An aliquot of 100 μl of cell culture containing about $10^4$ cells (e.g., SKBR-3, BT474, MCF7 or MDA-MB-468) in medium is deposited in each well of a 96-well, opaque-walled plate.
2. Control wells are prepared containing medium and without cells.
3. Conjugate is added to the experimental wells and incubated for 3-5 days.
4. The plates are equilibrated to room temperature for approximately 30 minutes.
5. A volume of CellTiter-Glo Reagent equal to the volume of cell culture medium present in each well is added.
6. The contents are mixed for 2 minutes on an orbital shaker to induce cell lysis.
7. The plate is incubated at room temperature for 10 minutes to stabilize the luminescence signal.
8. Luminescence is recorded and reported in graphs as RLU=relative luminescence units.

Example 58

Determination of Cytotoxicity of Selected Compounds

Following the procedure described in Example 57, Auristatin-Peptide-Antibody (Drug Linker Ligand) conjugates were evaluated on $CD70^+$ positive cell lines, 786-O, Caki-1, L428, UMRC-3, LP-1, U251, and a $CD70^-$ cell line, HCT-116, as a control. In addition, conjugate h1F6-vc-PABC-MMAF was used as a control. Tables 4 and 5 show the in vitro activity of selected Auristatin-Dipeptide-h1F6 conjugates (the Peptide having two amino acids) as compared to h1F6-vc-PABC-MMAF control conjugate. The conjugates contain approximately 4 drugs per antibody.

TABLE 4

IC50's (ng/mL) for Auristatin-Dipeptide-h1F6 (~4 drugs/Ab) conjugates on CD70+ cells

| Drug Linker in conjugate[+] | 786-0 | Caki-1 | L428 | UMRC-3 | LP-1 | U251 | HCT-116 (CD70−) |
|---|---|---|---|---|---|---|---|
| AF-Ile-Val | 3.4 | 3.7 | 2.5 | 19.5 | 19 | 44.6 | >1000 |
| AF-Asp-Val | 18 | 25 | 18 | 54 | 234 | 407 | >1000 |
| AF-Tyr-Val | 3.7 | 7.0 | 3.0 | 19.5 | 34 | 46.8 | >1000 |
| AF-Asn-Val | 12.6 | 22.3 | 11.7 | 46.8 | 174 | 251 | >1000 |
| AF-His-Val | 5.6 | 11.2 | 5.9 | 38 | 77.6 | 81.2 | >1000 |
| AF-Ile-Pro | 9.8 | 9 | 5 | 16 | 219 | 45 | >1000 |
| AF-Me$_3$Lys-Pro | 20 | 11 | 24 | 30 | 298 | 78 | >1000 |
| AF-Tyr-(D)Asp | 24 | 9 | 27 | 32 | 398 | 72 | >1000 |
| AF-NorVal-(D)Asp | 28 | 12 | 24 | 25 | 537 | 78 | >1000 |
| AF-β-Ala-(D)Asp | 525 | 1585 | 1096 | 132 | >10,000 | 93 | >1000 |
| AF-PhenylGly-(D)Lys | 339 | 44 | 275 | 1096 | >10,000 | 98 | >1000 |
| AF-Met-(D)Lys | 55 | 25 | 1698 | 132 | >10,000 | 98 | >1000 |
| AF-Pro-(D)Lys | NT | >10,000 | >10,000 | NT | NT | 5012 | >1000 |
| AF-Asn-(D)Lys | 19 | 10 | 24 | 28 | 417 | 60 | >1000 |
| vc-PABC-MMAF | 7 | 3 | 7 | 14 | 22 | 10 | >1000 |

AF = Auristatin F;

NT = not tested.

[+]The Stretcher unit of the Linker unit is as indicated in the Examples supra.

The results of these studies are shown in Table 4. In this example, the Auristatin F-dipeptide conjugates with antibody h1F6 generally exhibited comparable activity to the control, a h1F6-vc-PABC-MMAF conjugate. These results demonstrate that auristatins can be conjugated through C-terminus carboxyl group to a linker comprising amino acid units to generate active ADCs. The potency of such conjugates varies can depend on the amino acid sequence of the linkers. Conjugates with Drug Linkers comprising non-natural amino acids such as β-alanine and phenylglycine linked to the phenylalanine of the auristatin demonstrated reduced activity, potentially due to inefficient enzymatic cleavage of such substrates. The AF-Proline-(D)Lysine Drug Linker provided a largely inactive in an ADC, most probably due to inability or extreme difficulty of proteolytic cleavage of the secondary amide bond between phenylalanine and proline.

TABLE 5

IC50's (ng/mL) summary for Auristatin-Peptide-h1F6 (~4 drugs/Ab) conjugates on CD70+ cells

| Drug Linker-in conjugate[+] | IC50 (ng/mL) | | | | |
|---|---|---|---|---|---|
| | 786-O | Caki-1 | Caki-2 | L428 | HCT-116 (CD70−) |
| AF-Gln-(D)Lys | 12 | 11 | 14 | 209 | >1000 |
| AF-Arg-(D)Lys | 8 | 10 | 8 | 47 | >1000 |
| AF-Cit-(D)Lys | 10 | 11 | 16 | 47 | >1000 |
| AF-Tyr-(D)Lys | 9 | 11 | 12 | 10 | >1000 |
| AF-Lys-(D)Lys | 9 | 8 | 9 | 37 | >1000 |
| AF-Asn-Pro | 11 | 12 | 32 | 23 | >1000 |
| AF-Met-Pro | 8 | 15 | 25 | 8 | >1000 |
| AF-Met-(D)Met | 4 | 5 | 13 | 4 | >1000 |
| AF-Met-(D)Val | 5 | 6 | 32 | 8 | >1000 |
| AF-Met-(D)Asp | 8 | 10 | 35 | 11 | >1000 |
| AF-hPhe-(D)Asp | 10 | >1000 | >1000 | 29 | >1000 |
| AF-Asn-(D)Asp | 7 | 7 | 71 | 14 | >1000 |
| AF-Asn-(D)Lys-(D)Lys | 9 | 10 | 30 | 22 | >1000 |
| AF-Met-(D)Lys-(D)Lys | 8 | 12 | 25 | >1000 | >1000 |
| AM-Tyr-(D)Asp | 32 | 23 | 71 | 30 | >1000 |
| AM-Met-(D)Lys | 56 | 39 | 251 | 1000 | >1000 |
| AM-Asn-(D)Lys | 20 | 20 | 47 | 26 | >1000 |
| AM-Asn | 30 | 31 | 63 | 32 | >1000 |
| AW-Tyr-(D)Asp | 18 | 16 | 33 | 21 | >1000 |
| AW-Asn-(D)Lys | 16 | 15 | 26 | 19 | >1000 |
| AW-Met-(D)Lys | 20 | 22 | 37 | >1000 | >1000 |
| AW-Asn | 18 | 15 | 30 | 22 | >1000 |
| vc-PABC-MMAF | 5 | 12 | 11 | 4 | >1000 |

AF = Auristatin F;
AM = auristatin having Methionine at C-terminus;
AW = auristatin having Tryptophan at C-terminus
[+]The Stretcher unit of the Linker unit is as indicated in the Examples supra.

Table 5 shows the activity of another set of Auristatin-Dipeptide-h1F6 ADCs on CD70+ and CD70− cell lines. Most conjugates are highly active on CD70+ cells, while showing no activity on the CD70− cell line (HCT-116). The table also includes data for ADCs produced with Drug Linker compounds having only one amino acid in the Linker unit, as well as with Drug Linker compounds containing Auristatins M and W (having Methionine and Tryptophan at the C-terminus of the Drug, respectively). Auristatin M- and W-containing conjugates were active in these studies.

Example 59

Determination of Cytotoxicity of Selected Compounds Using

Following the procedure described in Example 57, Auristatin-Dipeptide-cAC10 antibody conjugates were evaluated on CD30+ positive cell lines, Karpas 299, L428 and L540cy. In addition, a control conjugate, cAC10-vc-PABC-MMAF, was used. Table 6 shows the in vitro activity of selected Auristatin-Dipeptide-cAC10 conjugates as compared to a cAC10-vc-PABC-MMAF control conjugate. The conjugates contain approximately 4 drugs per antibody.

TABLE 6

$IC_{50}$s (ng/mL) of Auristatin-Dipeptide-cAC10 (~4 drugs/Ab) conjugates on CD30+ cells

| Drug Linker[+] in conjugate | Karpas 299 | L428 | L540cy |
|---|---|---|---|
| AF-Ile-Pro | 0.6 | 0.1 | 0.7 |
| AF-Me₃Lys-Pro | 0.6 | 0.09 | 0.8 |
| AF-Tyr-(D)Asp | 0.6 | 0.06 | 0.7 |
| AF-NorVal-(D)Asp | 0.5 | 0.09 | 0.6 |
| AF-β-Ala-(D)Asp | 371 | 0.5 | 1.6 |
| AF-PhenylGly-(D)Lys | 21 | 2 | 6 |
| AF-Met-(D)Lys | 2 | 1.5 | 3 |
| AF-Asn-(D)Lys | 44 | 0.1 | 4 |
| vc-PABC-MMAF | 3 | 0.5 | 3 |

[+]The Stretcher unit of the Linker unit is as indicated in the Examples supra.

The data in Table 6 show that Auristatin-Dipeptide Drug Linkers provide potent cAC10 ADCs. The data show that the use of such Drug Linkers is not limited to h1F6, but can have broader application for targeted drug delivery.

Example 60

Tumor Volume In Viva Efficacy in Transgenic Explant Mice

Animals suitable for transgenic experiments can be obtained from standard commercial sources such as Taconic (Germantown, N.Y.). Many strains are suitable, but FVB female mice are preferred because of their higher susceptibility to tumor formation. FVB males can be used for mating and vasectomized CD.1 studs can be used to stimulate pseudopregnancy. Vasectomized mice can be obtained from any commercial supplier. Founders can be bred with either FVB mice or with 129/BL6×FVB p53 heterozygous mice. The mice with heterozygosity at p53 allele can be used to potentially increase tumor formation. Some F1 tumors are of mixed strain. Founder tumors can be FVB only.

Animals having tumors (allograft propagated from Fo5 mmtv transgenic mice) can be treated with a single or multiple dose by IV injection of ADC. Tumor volume can be assessed at various time points after injection.

Example 61

In Vivo Efficacy of Auristatin F-Dipeptide-h1F6 Conjugates in a Renal Cell Xenograft Model The efficacy of AF-Dipeptide-h1F6 conjugates were evaluated in 786-O (renal cell) xenografts. AF-Dipeptide-h1F6 conjugates with an average of 4 drug moieties per antibody were used. 786-O cells were implanted subcutaneously into immunodeficient mice ($5\times10^6$ cells per mouse). Tumor volumes are calculated using the formula ($0.5\times L\times W^2$) where L and W are the longer and shorter of two bidirectional measurements. The results of this study are shown in FIG. 1. Most of AF-Dipeptide-h1F6 ADCs showed efficacy in the in vivo model resulting in tumor volume reduction or total irradiation of established tumors. In vivo efficacy of the tested ADCs correlated with their in vitro potency. The AF-Pro-(D)Lys conjugate was inactive in the mouse model (data not shown). A number of AF-Dipeptide-h1F6 conjugates were more active than corresponding h1F6-vc-PABC-MMAF.

Figure 2:
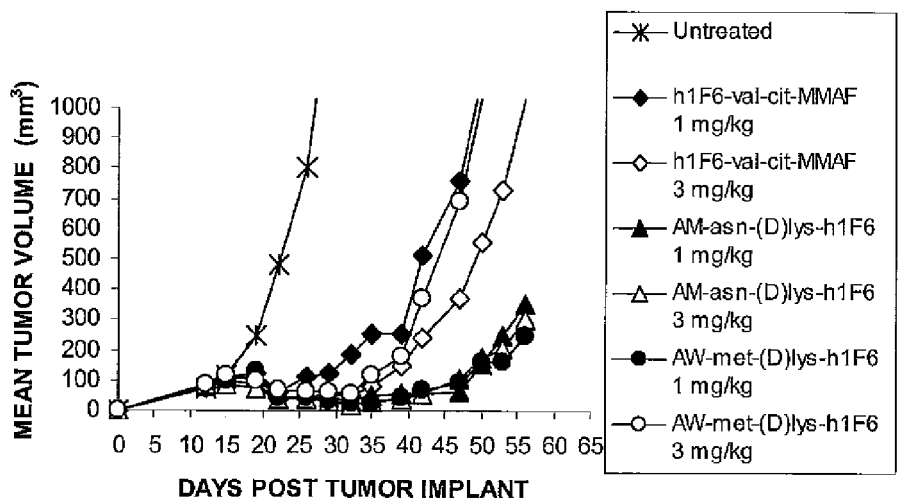
FIG. 2 shows in vivo efficacy data for Auristatin-Dipeptide-h1F6 conjugates in nude mice bearing subcutaneous 786O renal carcinoma tumors. The mice were given a single dose ip of the conjugates, as indicated in the figure, on day 12.

In a second study, the efficacies of additional Auristatin-Dipeptide-h1F6 conjugates were evaluated in 786-O (renal cell) xenografts. Auristatin-Dipeptide-h1F6 conjugates with an average of 4 drug moieties per antibody were used. 786-O cells were implanted subcutaneously into immunodeficient mice ($5 \times 10^6$ cells per mouse). Tumor volumes are calculated using the formula ($0.5 \times L \times W^2$), where L and W are the longer and shorter of two bidirectional measurements. The results of this study are shown in FIG. 2. The Auristatin-Dipeptide antibody conjugates caused in tumor regressions and cures at well tolerated doses.

Example 62

Figure 3:
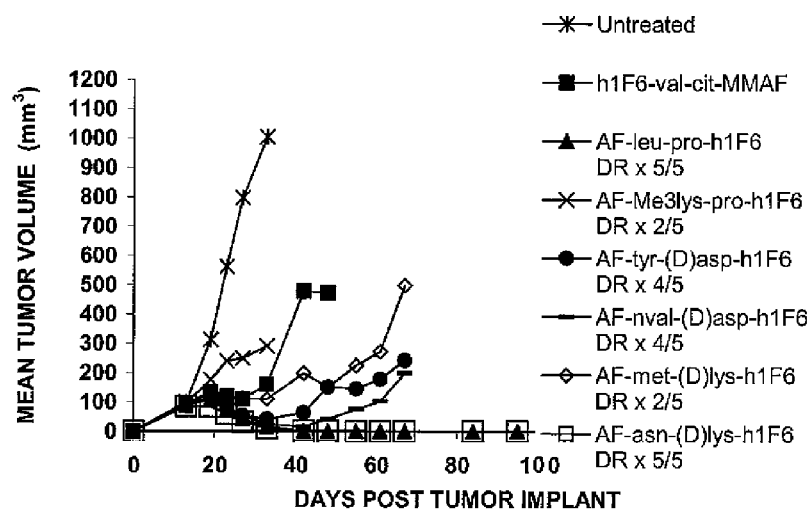
FIG. 3 shows in vivo efficacy data for AF-Dipeptide-h1F6 conjugates in nude mice bearing subcutaneous DBTRG05-MG glioblastoma tumors. The mice were given a single dose of 3 mg/kg of the conjugates on day 16. The number of durable responses is indicated for each group.

In Vivo Efficacy of Auristatin F-Dipeptide-h1F6 Conjugates in a Glioblastoma Xenograft Model The efficacies of Auristatin F-Dipeptide-h1F6 conjugates were evaluated in a DBTRGO5-MG glioblastoma subcutaneous model. Auristatin F-Dipeptide-h1F6 conjugates with an average of 4 drug moieties per antibody were used. DBTRGO5-MG cells were implanted subcutaneously into immunodeficient mice ($5 \times 10^6$ cells per mouse). Tumor volumes are calculated using the formula ($0.5 \times L \times W^2$) where L and W are the longer and shorter of two bidirectional measurements. The results of this study are shown in FIG. 3. The AF-Dipeptide-h1F6 conjugates showed superior efficacy as compared to corresponding N-terminus linked vc-PABC-MMAF conjugate, resulting in numerous cures at a low dose of 3 mg/kg single treatment of established tumors.

Example 63

In Vivo Efficacy of Auristatin F-Dipeptide-cAC10 Conjugates

Figure 4:
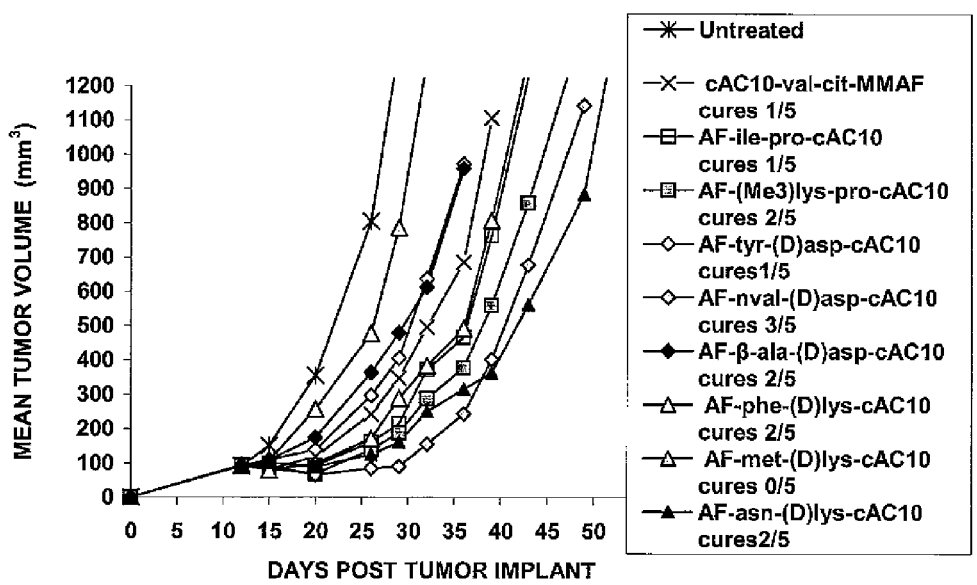
FIG. 4 shows in vivo efficacy data for AF-Dipeptide-cAC10 conjugates in a SCID mouse Karpas model (subcutaneous). The mice were given a single dose of 0.5 mg/kg ip of the conjugates on day 12. The number of cures is indicated for each group.
Figure 5:
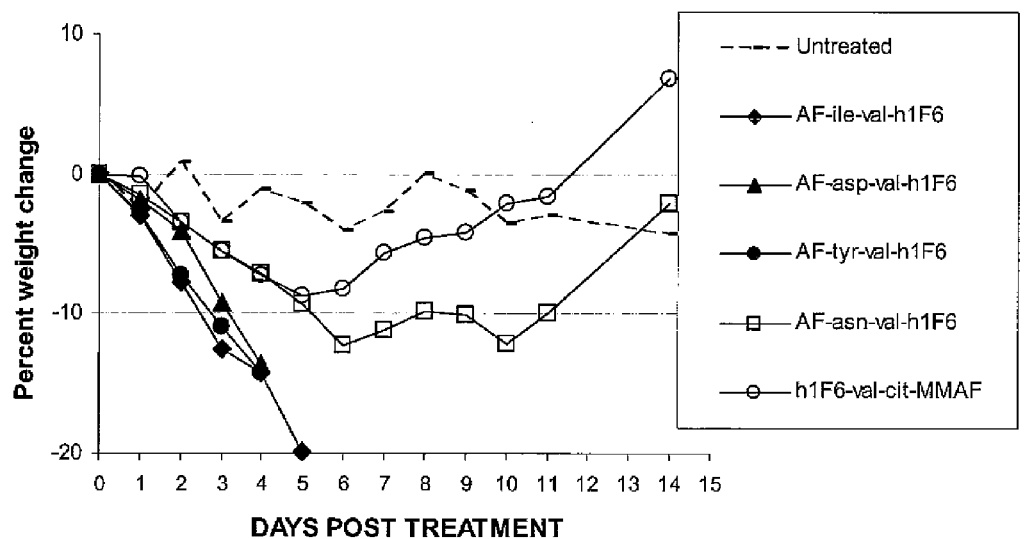
FIG. 5 shows tolerability data for balb/c mice given a single dose, 50 mg/kg ip, of the indicated AF-Dipeptide-h1F6 conjugates. An h1F6-vc-PABC-MMAF conjugate is used as a control.
Figure 6:
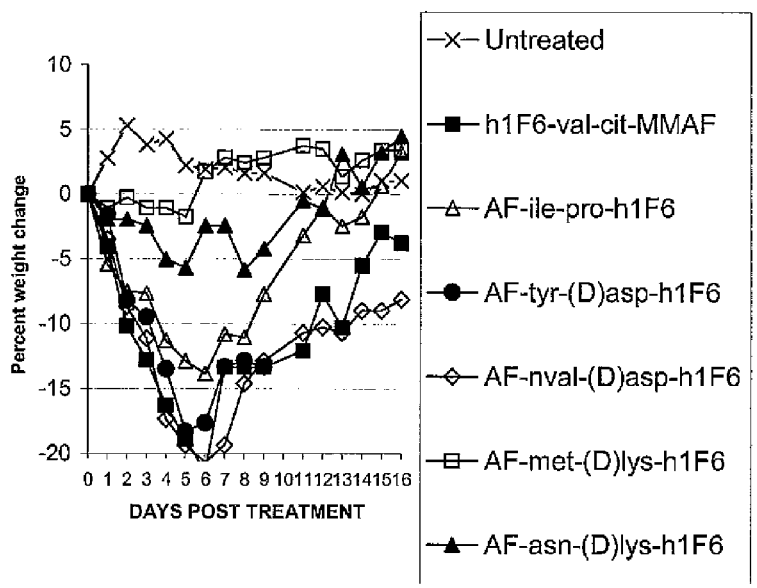
FIG. 6 shows tolerability data for balb/c mice given a single dose, 75 mg/kg ip, of the indicated AF-Dipeptide-h1F6 conjugates. An h1F6-vc-PABC-MMAF conjugate is used as a control.

The efficacy of Auristatin F-Dipeptide-cAC10 were evaluated in Karpas-299 ALCL xenografts. Auristatin F-Dipeptide-cAC10 conjugates with an average of 4 drug moieties per antibody were used. Karpas-299 human ALCL cells were implanted subcutaneously into immunodeficient C.B-17 SCID mice ($5 \times 10^6$ cells per mouse). Tumor volumes were calculated using the formula ($0.5 \times L \times W2$) where L and W are the longer and shorter of two bidirectional measurements. The results are shown in FIG. 4.

Treatment of the established tumors with single dose of only 0.5 mg/kg of the AF-Dipeptide-cAC10 conjugates resulted in tumor regressions and cures.

Example 64

Tolerability of Auristatin-Dipeptide-h1F6 Conjugates in Mice

Figure 7:
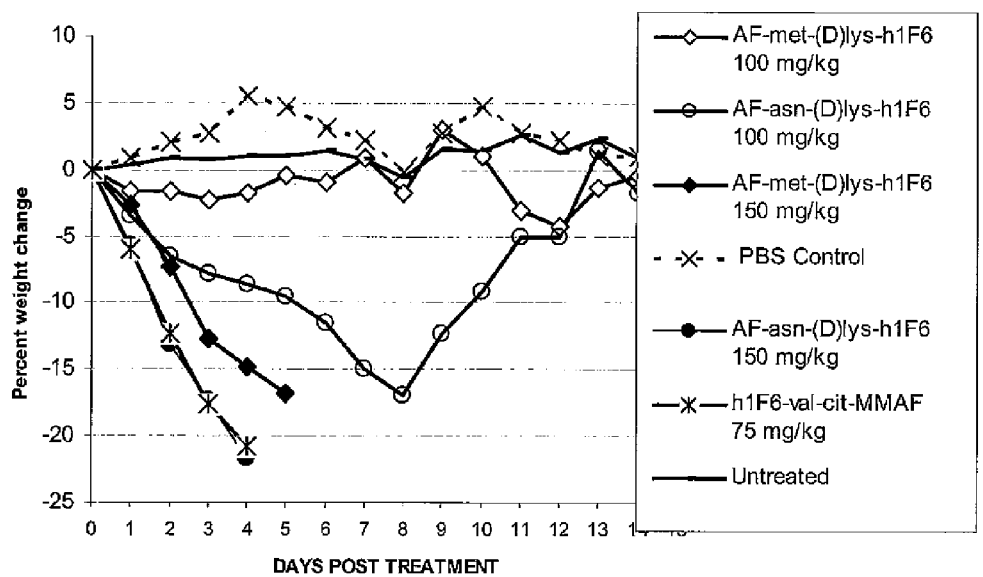
FIG. 7 shows tolerability data for balb/c mice given a single dose iv, at the indicated amount, of AF-Dipeptide-h1F6 conjugates. An h1F6-vc-PABC-MMAF conjugate is used as a control.
Figure 8:
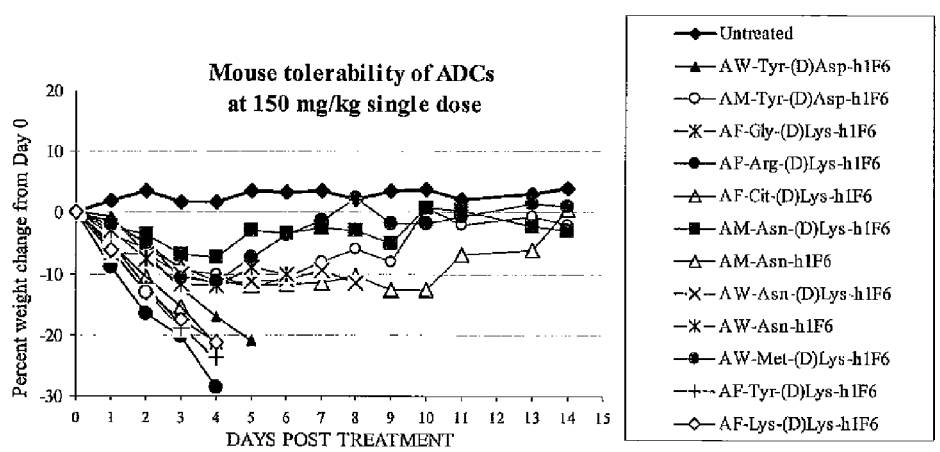
FIG. 8 shows tolerability data in mice given a single dose of 150 mg/kg of Auristatin-Dipeptide-h1F6 conjugates.
Figure 9:
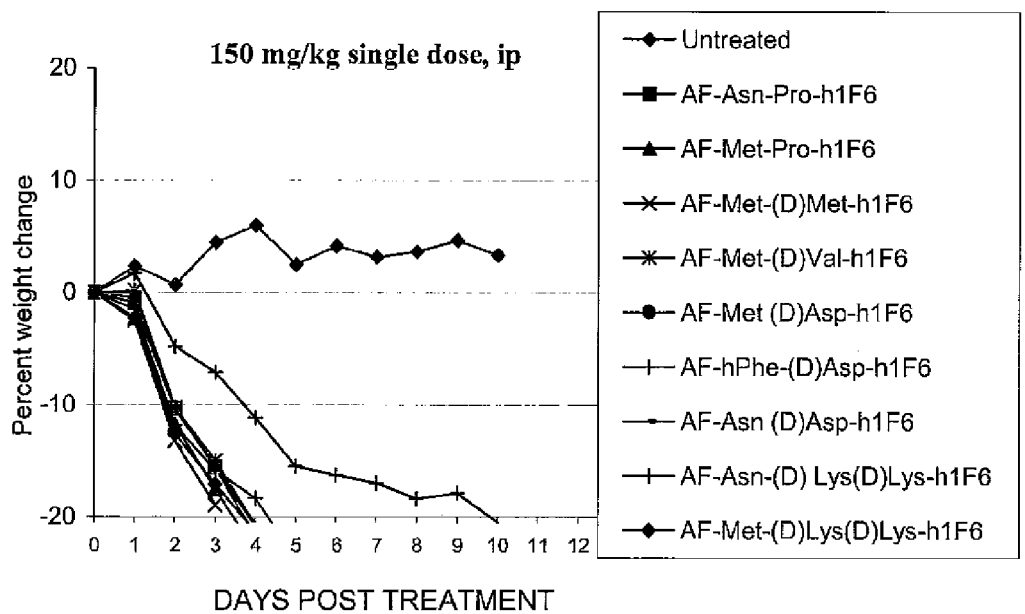
FIG. 9 shows tolerability data for mice given 150 mg/kg of a single dose ip of the indicated AF-Dipeptide- or AF-Tripeptide-h1F6 conjugates.

The tolerability, measured as maximum tolerated dose (MTD), was determined in mice based on animals' weight loss after treatment. Animals were usually monitored for 14 days. A conjugate is considered to be tolerated at a determined dose if single iv treatment at such dose results in a transient weight loss of no more than 20% of initial body weight of animals and no other signs of toxicity are observed. The results are shown in FIGS. 5-9. Tolerability of Auristatin-Dipeptide-h1F6 conjugates with an average of 4 drug units per antibody was found to depend on the dipeptide sequence of the Linker and the auristatin. AF-Met-(D)Lys and AF-Asn-(D)Lys conjugates were tolerated at doses as high as 100 mg/kg (FIG. 7). Corresponding conjugates of auristatins containing Methionine (AM) and Tryptophan (AW) at the C-terminal position of the drug were tolerated even better, up to 150 mg/kg (FIG. 8). These doses are significantly higher than doses found to be efficacious in vivo (50+ fold higher). Thus, the Auristatin-Dipeptide Drug Linkers provide ADCs with significant therapeutic window for therapeutic treatment (e.g., cancer).

Example 65

Figure 10:
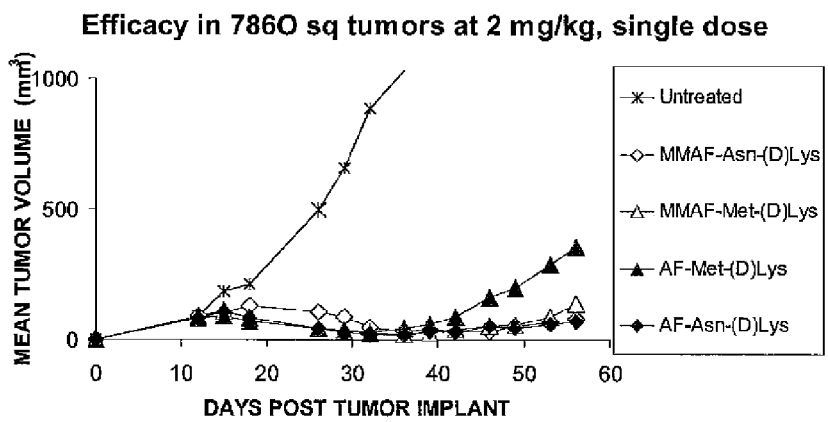
FIG. 10 shows in vivo efficacy data for a subcutaneous 786O human renal cell carcinoma mouse model. The mice were administered AF-Dipeptide-h1F6 conjugates or MMAF-Dipeptide-h1F6 conjugates. A single dose of 2 mg/kg ip of a conjugate was given on day 12.
Figure 11:
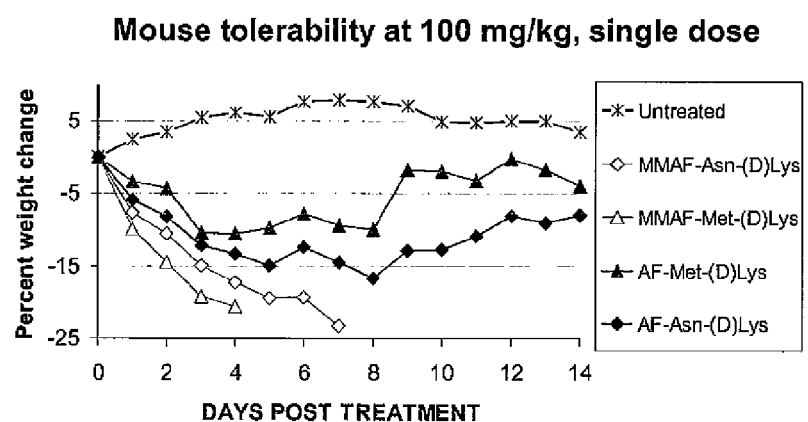
FIG. 11 shows tolerability data for balb/c mice given a single dose ip of 100 mg/kg AF-Dipeptide-h1F6 conjugates or MMAF-Dipeptide-h1F6 conjugates.

Comparison of the Efficacy and Tolerability of Selected Auristatin-Dipeptide-Antibody Conjugates The efficacies and tolerabilities (MTD) of corresponding Auristatin-Dipeptide-Antibody conjugates were compared for two different drugs, Auristatin F (AF) or MMAF, using the dipeptide-containing Linker Asn-(D)Lys or Met-(D)Lys. The efficacy and tolerability studies were generally performed as described in Examples 58 and 64, respectively. The results are shown in the following Table 7 and in FIGS. 10-11.

TABLE 7

IC50's (ng/mL) summary for selected Auristatin-Dipeptide-h1F6 conjugates

| Drug | Linker+ | 786-O | Caki-1 | L-428 | UMRC-3 | LP-1 |
|---|---|---|---|---|---|---|
| AF | Met- | 12 | 9 | 158 | 182 | >1000 |
| MMAF | (D)Lys | 10 | 8 | 123 | 100 | >1000 |
| AF | Asn- | 10 | 6 | 9 | 32 | 479 |
| MMAF | (D)Lys | 9 | 7 | 7 | 19 | 110 |

+The Stretcher unit of the Linker unit is as indicated in the Examples supra.

The data show that MMAF and AF ADCs have similar in vitro and in vivo potency independent of which drug was used with the dipeptide-containing linkers. MMAF-containing conjugates appear to be some less tolerated than corresponding Auristatin F-containing ADCs. Both MMAF-Met-(D)Lys and MMAF-Asn-(D)Lys-h1F6 conjugates resulted in animal loss at 100 mg/kg dose while corresponding AF conjugates were tolerated at this dose.

Example 66

Figure 12:
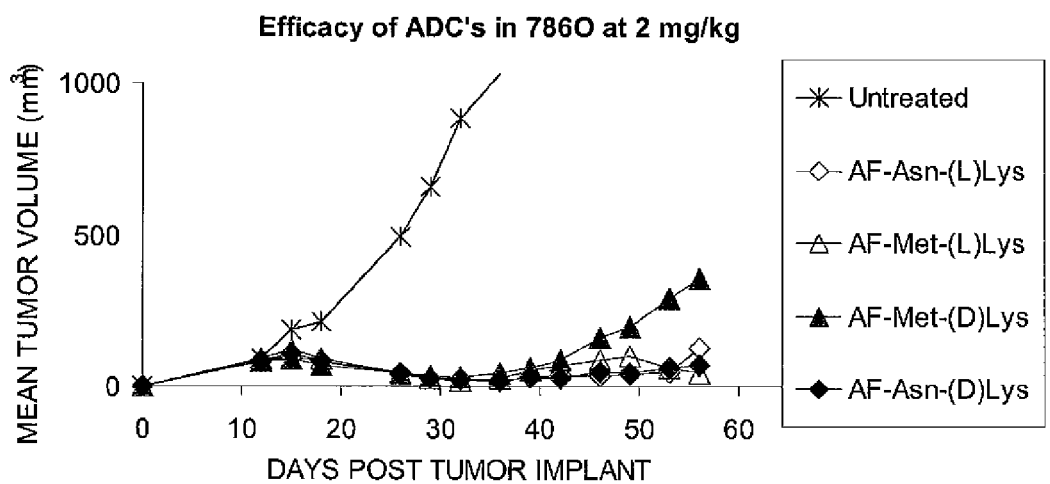
FIG. 12 shows in vivo efficacy data for a nude mouse xenograft model bearing subcutaneous 786O renal carcinoma tumors. The mice were given a single dose ip of 2 mg/kg of the indicated conjugates at day 12.

Comparison of the Efficacy and Tolerability of Selected Auristatin-Dipeptide-Antibody Conjugates The efficacy and tolerability (MTD) of Auristatin-Dipeptide-Antibody conjugates were compared using different linkers, having D or L amino acids in the second amino acid position of the Linker unit. The efficacy and tolerability studies were generally performed as described in Examples 58 and 64, respectively. The results are shown in the following Table 8 and in FIGS. 12-13.

TABLE 8

IC50's (ng/mL) summary for Auristatin-Dipeptide-h1F6 conjugates

| Drug | Linker+ | 786-O | Caki-1 | L-428 | UMRC-3 | LP-1 |
|---|---|---|---|---|---|---|
| AF | Met-(D)Lys | 12 | 9 | 158 | 182 | >1000 |
|  | Met-(L)Lys | 7 | 4 | 3 | 22 | 95 |
| AF | Asn-(D)Lys | 10 | 6 | 9 | 32 | 479 |
|  | Asn-(L)Lys | 9 | 8 | 8 | 26 | 501 |

+The Stretcher unit of the Linker unit is as indicated in the Examples supra.

Figure 13:
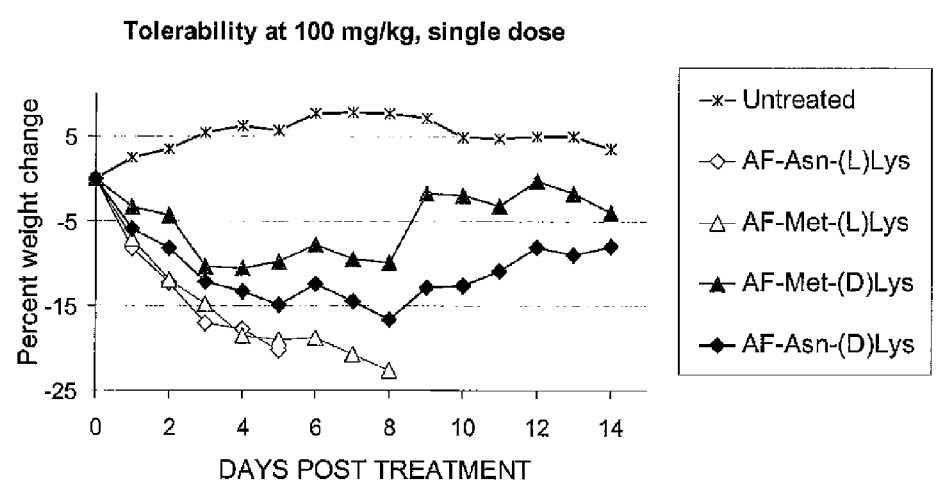
FIG. 13 shows tolerability data for balb/c mice given a single dose ip of 100 mg/kg of AF-Asn-(D)Lys, AF-met-(D)Lys-h1F6, AF-Asn-(L)Lys or AF-met-(L)Lys-h1F6 conjugates.

Drug Linkers with an L-amino acid in second position provided less tolerated ADCs for both tested linkers, as shown in FIG. 13, while in vitro and in vivo potency of these conjugates were comparable.

Example 67

Figure 14:
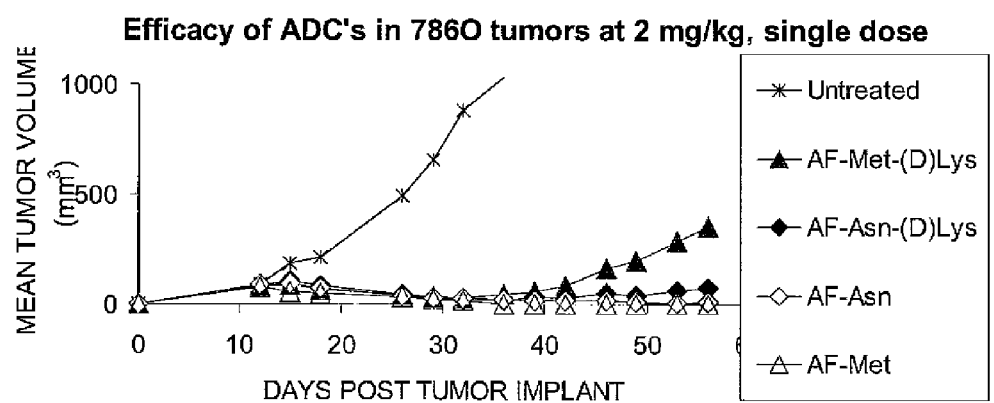
FIG. 14 shows in vivo efficacy data for a nude mouse xenograft model bearing subcutaneous 786O renal carcinoma tumors. The mice were given a single dose ip of 2 mg/kg of the indicated conjugates having one or two amino acids in the linker.

Comparison of the Efficacy and Tolerability of Selected Auristatin-Peptide-Antibody Conjugates with a Mono or Dipeptide Linkers The efficacies and tolerabilities (MTD) of Auristatin-Peptide-Antibody conjugates were compared using mono- or di-peptide amino acid linkers. The efficacy and tolerability studies were generally performed as described in Examples 58 and 64, respectively. The results are shown in the following Table 9 and in FIGS. 14-15.

TABLE 9

IC50's (ng/mL) summary for h1F6-Drug(4) conjugates

| Drug | Linker[+] | 786-O | Caki-1 | L-428 | UMRC-3 | LP-1 |
|------|-----------|-------|--------|-------|--------|------|
| AF   | Met-(D)Lys | 12 | 9 | 158 | 182 | >1000 |
|      | Met       | 8  | 6 | 3   | 17  | 110  |
| AF   | Asn-(D)Lys | 10 | 6 | 9   | 32  | 479  |
|      | Asn       | 10 | 6 | 9   | 28  | 209  |

[+]The Stretcher unit of the Linker unit is as indicated in the Examples supra.

Figure 15:
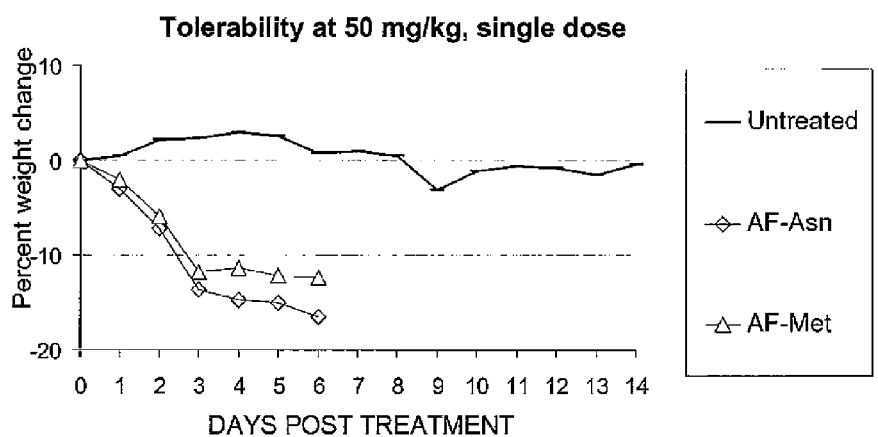
FIG. 15 shows tolerability data for balb/c mice given a single dose ip of 50 mg/kg of the indicated h1F6-conjugates; the conjugate have one amino acid in the linker.

The results of the studies show that conjugates with only one amino acid in the linker were significantly less tolerated as compared with corresponding conjugates having dipeptide linkers (FIG. 15). AF-Asn-h1F6 and AF-Met-h1F6 were toxic at 50 mg/kg dose while corresponding AF-Asn-(D)Lys and AF-Met-(D)Lys conjugates were tolerated at 100 mg/kg. These data support using at least two amino acids in the peptide linkers for C-terminal linked Auristatin-Peptide-Antibody conjugates.

General Example 68

Preparation of Auristatin-AA1-AA2 Drug Linkers with Aryl-maleimides

Auristatin-peptide drug linkers with aryl-maleimides in the Stretcher unit were prepared by substituting 3-maleimidopropionic acid NHS ester in step (j) of Example 10, as modified in Example 24, with p-maleimidobenzoyl NHS ester.

Example 69

Preparation of AM-Asparagine-(D)Lysine-diaminoethane-benzoyl Maleimide (10e, AA1-AA2=Asparagine-(D)Lysine)

AM-Asparagine-(D)Lysine-diaminoethane-benzoyl maleimide (10e) was prepared in the same manner as 9c, starting with 100 mg of Fmoc-(D)Lysine(boc)diaminoethane-trityl resin (4), and using p-maleimidobenzoyl NHS ester in the place of 3-maleimidopropionic acid NHS ester. Yield: 24 mg. RP-HPLC analysis >95% at 10.30 min; ESMS m/z=1212.84 (M+H)[+].

Example 70

Preparation of AW-Methionine(D)Lysine-diaminoethane-benzoyl Maleimide (10f, AA2-AA1=Methionine-(D)Lysine)

AW-Methionine-(D)Lysine-diaminoethane-benzoyl maleimide was prepared in the same manner as 10b, starting with 100 mg of Fmoc-(D)Lysine(boc)-diaminoethane-trityl resin (4), and using p-maleimidobenzoyl NHS ester in the place of 3-maleimidopropionic acid NHS ester. Yield: 8 mg. RP-HPLC analysis >95% at 10.81 min; ESMS m/z=1285.64 (M+H)[+].

Example 71

Comparison of the Potency of Selected Aryl and Alkyl Auristatin-Peptide-h1F6 Conjugates on CD70[+] Cells Following the procedure described as Examples 57 and 58, Auristatin-Peptide-h1F6 conjugates were evaluated on CD70[+] cell, such as 786-O, Caki-1, Caki-2, and L428. Conjugates contain approximately 4 drugs per antibody. Referring to the following Table 10, the respective aryl- and alkyl-maleimide containing Drug-Linkers resulted in conjugates with similar activities.

TABLE 10

IC50s' (ng/mL) summary for h1F6-Drug(4) conjugates using aryl or alkyl maleimides

| Drug Linker[+] | $IC_{50}$ (ng/mL) | | | |
|---|---|---|---|---|
| | 786-O | Caki-1 | Caki-2 | L428 |
| AW-Met-(D)Lys-aryl-maleimide | 12 | 15 | 12 | >1000 |
| AW-Met-(D)Lys-propionyl-maleimide | 17 | 19 | 18 | >1000 |
| AM-Asn-(D)Lys-aryl maleimide | 16 | 10 | 17 | 23 |
| AM-Asn-(D)Lys-propionyl-maleimide | 18 | 16 | 26 | 29 |

AM = auristatin having Methionine at C-terminus;
AW = auristatin having Tryptophan at C-terminus
[+]The Stretcher unit of the Linker unit is as indicated in the Examples supra.

Example 72

Activity of AM-Asn-(D)Lys and AW-Met-(D)Lys Conjugates with cAC10 (Anti-CD30), hBU12 (Anti-CD19), Anti-LIV-1, and BR96 (anti-Le[y]) Antibodies In Vitro Following the procedure described as Examples 57 and 58, the activities of Auristatin-Peptide-cAC10 conjugates were evaluated on CD30[+] cells, such as Karpas 299, L428, and L540cy. The activities of Auristatin-Peptide-hBU12 conjugates were evaluated on CD19[+] cells such as Ramos, SUDHL-4, and ARH-77. The activities of Auristatin-Peptide-anti-LIV-1 conjugates were evaluated on LIV-1 positive cell lines MCF-7 and SKOV-3. The activities of Auristatin-Peptide-BR96 conjugates were evaluated on Le[y] positive cells H3396, RCA, and L2987. All conjugates contain approximately 4 drugs per antibody.

Referring to Table 11, the results are shown. AM-Asn-(D)Lys conjugates had similar in vitro potency as corresponding MC-MMAF conjugates. AW-Met-(D)Lys conjugates appear to be less active.

TABLE 11

Summary of IC50s (ng/mL) for selected Auristatin-peptide conjugates with cAC10, hBU12, Anti-LIV-1, and BR96 antibodies.

| | cAC10 | | | hBU12 | | Anti-LIV-1 | | | BR96 | | |
|---|---|---|---|---|---|---|---|---|---|---|---|
| Drug-linker | Karpas 299 | L428 | L540cy | Ramos | SUDHL-4 | ARH-77 | MCF-7 | SKOV-3 | H3396 | RCA | L2987 |
| AM-Asn-(D)Lys | 11 | 0.6 | 31 | 1 | >10,000 | 49 | 24 | 7600 | 37 | 8362 | 506 |
| AW-Met-(D)Lys | 11 | ~10,000 | 17 | >10,000 | >10,000 | >10,000 | >10,000 | >10,000 | 146 | 5217 | 422 |
| MC-MMAF | 3 | 1 | 7 | 7 | ~10,000 | 255 | 3 | 2450 | 42 | 7400 | 626 |

AM = auristatin having Methionine at the C-terminus;
AW = auristatin having Tryptophan at the C-terminus;
MC-MMAF = Maleimidocaproyl-monomethylauristatin F.

Example 73

Figure 16:
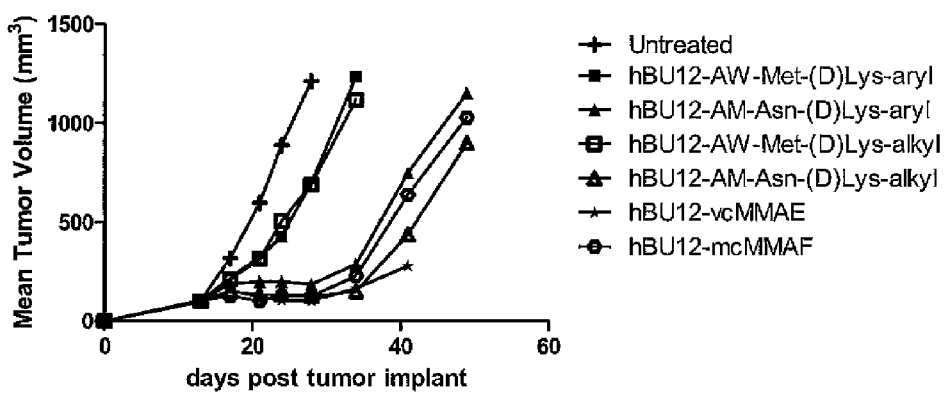
FIG. 16 shows in vivo efficacy data for SCID mice having subcutaneous follicular B-cell lymphoma DoHH-2 human xenograft tumors. The mice were given a multiple doses (3 mg/kg (4-qd×4) ip) of the indicated Auristatin-Dipeptide-hBU12 conjugates. Treatment was initiated at day 13.

In Vivo Efficacy of Selected Auristatin-Dipeptide-hBU12 Conjugates in a Lymphoma Xenograft Model The efficacies of Auristatin-Dipeptide hBU12 conjugates with the aryl and alkyl-maleimide Stretcher units were evaluated in a DoHH-2 follicular B-cell lymphoma subcutaneous model. Auristatin-Dipeptide-hBU12 conjugates with average of 4 drug moieties per antibody were used. DoHH-2 cells were implanted subcutaneously into immunodeficient SCID mice (5×106 cells per mouse). Tumor volumes are calculated using the formula (0.5×L×W$^2$) where L and W are the longer and shorter of two bidirectional measurements. Treatment was initiated when average size of tumors reached 100 mm$^3$; the treatment schedule was q4d×4 at 3 mg/kg. The results of this study are shown in FIG. 16.

Conjugates of aryl and alkyl maleimide analogues of corresponding Auristatin-Dipeptides showed similar efficacies. AM-Asn-(D)Lys ADCs were more potent than corresponding AW-Met-(D)Lys conjugates.

Example 74

Figure 17:
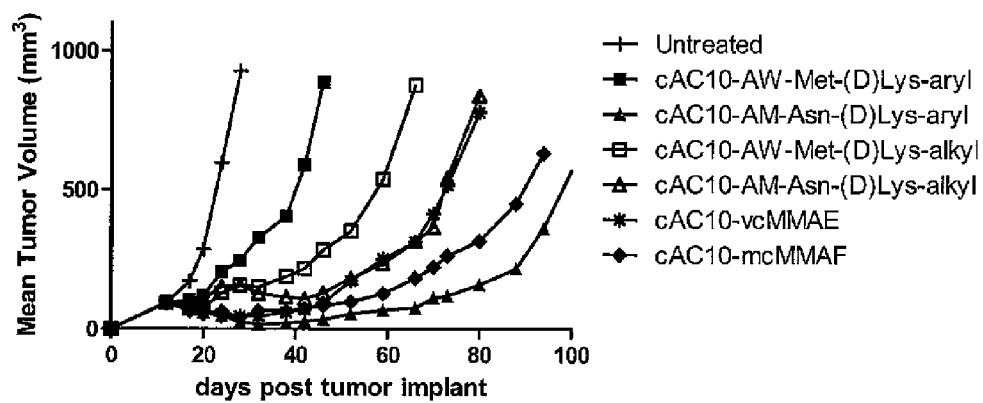
FIG. 17 shows in vivo efficacy data for SCID mice bearing subcutaneous Hodgkin's lymphoma L540cy human xenograft tumors. The mice were given multiple doses (1 mg/kg doses (4-qd×3) ip) of the indicated conjugates. Treatment was initiated at day 12.

In Vivo Efficacy of Auristatin-Dipeptide-cAC10 Conjugates in a Lymphoma Xenograft Model The efficacy of selected Auristatin-Dipeptide-cAC10 conjugates having Stretcher units with aryl or alkyl maleimides were evaluated in L540cy Hodgkin's lymphoma subcutaneous model. Auristatin-Dipeptide-cAC10 conjugates with average of 4 drug moieties per antibody were used. L540cy cells were implanted subcutaneously into immunodeficient SCID mice (5×10$^6$ cells per mouse). Tumor volumes were calculated using the formula (0.5×L×W2) where L and W are the longer and shorter of two bidirectional measurements. Treatment was initiated when average size of tumors reached 100 mm$^3$. The treatment schedule was q4d×3 at 1 mg/kg. The results of this study are shown in FIG. 17. The conjugates showed similar efficacy. AM-Asn-(D)Lys ADCs were more potent than corresponding AW-Met-(D)Lys conjugates in this study.

Example 75

Plasma Clearance in Rat

Plasma clearance pharmacokinetics of antibody drug conjugates and total antibody is studied in Sprague-Dawley rats (e.g., from Charles River Laboratories, 250-275 grams each). Animals are dosed by bolus tail vein injection (IV Push). Approximately 300 µl whole blood is collected through jugular cannula, or by tail stick, into lithium/heparin anticoagulant vessels at each timepoint: 0 (predose), 10, and 30 minutes; 1, 2, 4, 8, 24 and 36 hours; and 2, 3, 4, 7, 14, 21, and 28 days post dose. Total antibody is measured by ELISA, for example, by coating with the extracellular domain of the target protein and detecting with an anti-human Fc-HRP antibody conjugate (ECD/GxhuFc-HRP). Antibody drug conjugate is measured by ELISA, for example, by coating with an anti-drug or antiFc antibody and detecting with an extracellular domain-biotin conjugate and a streptavidin-horse radish peroxidase conjugate.

Example 76

Plasma Clearance in Monkey

Plasma clearance pharmacokinetics of antibody drug conjugates and total antibody can be studied in cynomolgus monkeys, using a similar procedure to that described above in Example 75.

All references cited herein are incorporated by reference in their entirety and for all purposes to the same extent as if each individual publication or patent or patent application was specifically and individually indicated to be incorporated by reference in its entirety for all purposes. The recitation of any reference in this application is not an admission that the reference is prior art to this application.

What is claimed is:

1. A compound having the formula:

$$(D-LU)_p-L$$

or a pharmaceutically acceptable salt or solvate thereof;

wherein L is Ligand Unit, LU is a Linker unit, and D is a Drug unit;

L is a peptide, polypeptide or protein that specifically binds to a target cell population;

LU has the formula -W$_w$-A$_a$,

W$_w$ is a sequence of w independently selected amino acid diradicals, wherein the W proximal to the Drug unit (W$_1$) is a natural (L) amino acid linked via a peptide bond to the Drug unit and the remaining Ws are D-amino acids, provided that W$_1$ cannot form secondary amide with C-terminal amino acid of D and that the peptide bond can be cleaved by an intracellular protease, w is an integer ranging from 1 to 12, A is Stretcher unit, and a is 1 or 2;

p is an integer of from 1 to 20; and

D has the formula:

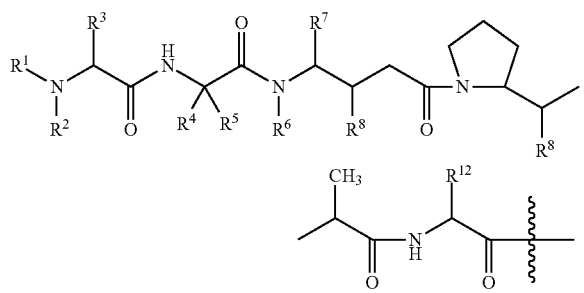

wherein the wavy line indicates the peptide bond to LU;
$R^1$ and $R^2$ are independently selected from the group consisting of —H and —$C_1$-$C_8$ alkyl, with the proviso that both $R^1$ and $R^2$ are not —H;
$R^3$ is selected from the group consisting of —H, —$C_1$-$C_8$ alkyl, —$C_3$-$C_8$ carbocycle, -aryl, —$C_1$-$C_8$ alkyl-aryl, —$X^1$—($C_3$-$C_8$ carbocycle), —$C_3$-$C_8$ heterocycle and —$X^1$—($C_3$-$C_8$ heterocycle);
$R^4$ is selected from the group consisting of —H, —$C_1$-$C_8$ alkyl, —$C_3$-$C_8$ carbocycle, -aryl, —$X^1$-aryl, —$C_1$-$C_8$ alkyl-($C_3$-$C_8$ carbocycle), —$C_3$-$C_8$ heterocycle and —$X^1$-($C_3$-$C_8$ heterocycle);
$R^5$ is selected from the group consisting of —H and methyl;
or $R^4$ and $R^5$ jointly form a carbocyclic ring and have the formula —$(CR^aR^b)_n$— wherein $R^a$ and $R^b$ are independently selected from the group consisting of —H and —$C_1$-$C_8$ alkyl and n is selected from the group consisting of 2, 3, 4, 5 and 6;
$R^6$ is selected from the group consisting of —H and —$C_1$-$C_8$ alkyl;
$R^7$ is selected from the group consisting of —H, —$C_1$-$C_8$ alkyl, —$C_3$-$C_8$ carbocycle, -aryl, —$X^1$-aryl, —$X^1$—($C_3$-$C_8$ carbocycle), —$C_3$-$C_8$ heterocycle and —$X^1$—($C_3$-$C_8$ heterocycle);
each $R^8$ is independently selected from the group consisting of —H, —OH, —$C_1$-$C_8$ alkyl, —$C_3$-$C_8$ carbocycle and —O—($C_1$-$C_8$ alkyl);
$R^{12}$ is selected from —H, —$C_1$-$C_8$ alkyl, -aryl, —$X^1$-aryl, —$C_3$-$C_8$ carbocycle, —$X^1$—($C_3$-$C_8$ heterocycle), —$C_1$-$C_8$ alkylene-$NH_2$, —$C_3$-$C_8$ heterocycle and —$X^1$-($C_3$-$C_8$ heterocycle); and
each $X^1$ is independently —$C_1$-$C_{10}$ alkylene-.

2. A compound having the formula:

D-LU or a pharmaceutically acceptable salt or solvate thereof;
wherein LU- is a Linker unit and D is a Drug unit;
LU has the formula $W_w$-$A_a$-,
$W_w$ is a sequence of w independently selected amino acid diradicals, wherein the W proximal to the Drug unit ($W_1$) is a natural (L) amino acid linked via a peptide bond to the Drug unit and the remaining Ws are D-amino acids, provided that $W_1$ cannot form secondary amide with C-terminal amino acid of D and that the peptide bond can be cleaved by an intracellular protease,
w is an integer ranging from 1 to 12,
A is Stretcher unit, and
a is 1 or 2; and
D has the formula:

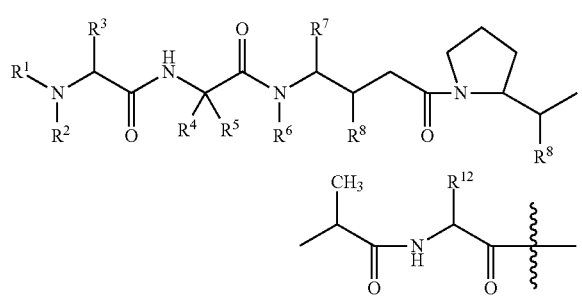

wherein the wavy line indicates the peptide bond to LU;
$R^1$ and $R^2$ are independently selected from the group consisting of —H and —$C_1$-$C_8$ alkyl;
$R^3$ is selected from the group consisting of —H, —$C_1$-$C_8$ alkyl, —$C_3$-$C_8$ carbocycle, -aryl, —$C_1$-$C_8$ alkyl-aryl, —$X^1$- ($C_3$-$C_8$ carbocycle), —$C_3$-$C_8$ heterocycle and —$X^1$- ($C_3$-$C_8$ heterocycle);
$R^4$ is selected from the group consisting of —H, —$C_1$-$C_8$ alkyl, —$C_3$-$C_8$ carbocycle, -aryl, —$X^1$-aryl, —$C_1$-$C_8$ alkyl-($C_3$-$C_8$ carbocycle), —$C_3$-$C_8$ heterocycle and —$X^1$- ($C_3$-$C_8$ heterocycle);
$R^5$ is selected from the group consisting of —H and -methyl;
or $R^4$ and $R^5$ jointly form a carbocyclic ring and have the formula —$(CR^aR^b)_n$— wherein $R^a$ and $R^b$ are independently selected from the group consisting of —H and —$C_1$-$C_8$ alkyl and n is selected from the group consisting of 2, 3, 4, 5 and 6;
$R^6$ is selected from the group consisting of —H and —$C_1$-$C_8$ alkyl;
$R^7$ is selected from the group consisting of —H, —$C_1$-$C_8$ alkyl, —$C_3$-$C_8$ carbocycle, -aryl, —$X^1$-aryl, —$X^1$—($C_3$-$C_8$ carbocycle), —$C_3$-$C_8$ heterocycle and —$X^1$—($C_3$-$C_8$ heterocycle);
each $R^8$ is independently selected from the group consisting of —H, —OH, —$C_1$-$C_8$ alkyl, —$C_3$-$C_8$ carbocycle and —O—($C_1$-$C_8$ alkyl);
$R^{12}$ is selected from H, —$C_1$-$C_8$ alkyl, -aryl, —$X^1$-aryl, —$C_3$-$C_8$ carbocycle, —$X^1$—($C_3$-$C_8$ heterocycle), —$C_1$-$C_8$ alkylene-$NH_2$, —$C_3$-$C_8$ heterocycle and —$X^1$—($C_3$-$C_8$ heterocycle); and
each $X^1$ is independently —$C_1$-$C_{10}$ alkylene-.

3. The compound of claim 1 or 2, wherein D has the formula:

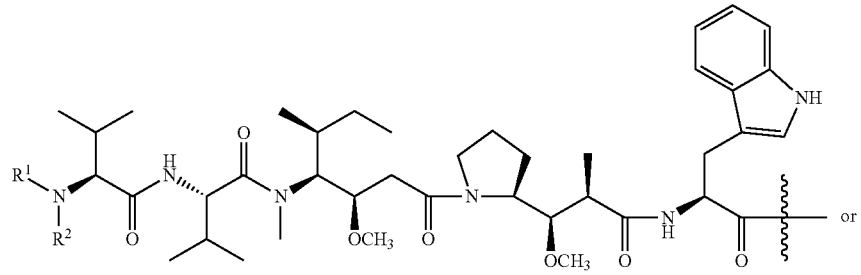

or

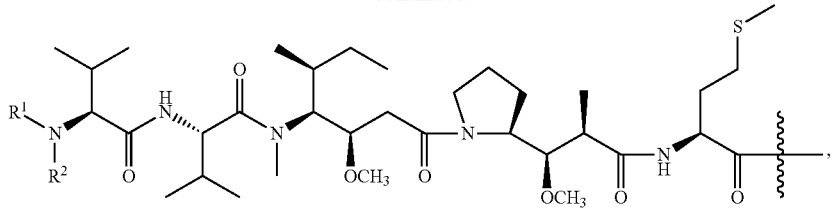

wherein $R^1$ and $R^2$ are as set forth above.

4. The compound of claim 3, wherein $R^1$ and $R^2$ are —$CH_3$.

5. The compound of claim 1 or 2, wherein w is 2-12 and the remaining W's are D-isomers of a natural amino acid.

6. The compound of claim 1 or 2, wherein a is 1.

7. The compound of claim 1 or 2, wherein a is 2.

8. The compound of claim 6, wherein A has the formula —NH—$R^9$-$R^{11}$ and $R^9$-$R^{11}$ have the formula:

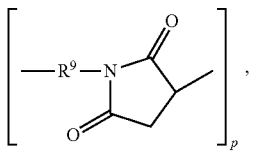

wherein $R^9$ is selected from the group consisting of —$C_1$-$C_{10}$ alkylene-, —$C_3$-$C_8$ carbocyclo-, -arylene-, —$C_1$-$C_{30}$ heteroalkylene-, —$C_3$-$C_8$ heterocyclo-, —$C_1$-$C_{10}$ alkylene-arylene-, -arylene-$C_1$-$C_{10}$alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, and —($C_3$-$C_8$ heterocyclo)-$C_1$-$C_{10}$ alkylene-.

9. The compound of claim 8, wherein —NH—$R^9$ is selected from the group consisting of —NH—$C_1$-$C_{10}$ alkylene-, —NH—$C_1$-$C_{10}$ alkylene-NH—C(O)—$C_1$-$C_{10}$ alkylene-, —NH—$C_1$-$C_{10}$ alkylene-C(O)—NH—$C_1$-$C_{10}$ alkylene-, —NH—($CH_2CH_2O$)$_r$—, —NH—($CH_2CH_2O$)$_r$—$CH_2$—, —NH—$C_1$-$C_{10}$ alkylene-, —O—$C_1$-$C_{10}$ alkylene-, —NH—$C_1$-$C_{10}$ alkylene-NH—C(O)—$C_1$-$C_{10}$ alkylene-, —NH—($C_3$-$C_8$ carbocyclo)-, —NH-(arylene-)-, —NH—$C_1$-$C_{10}$alkylene-NH—C(O)-(arylene-)-, and —NH—($C_3$-$C_8$ heterocyclo-)-, wherein r is an integer of from 1-10.

10. The compound of claim 9, wherein —NH—$R^9$ is selected from the group consisting of:

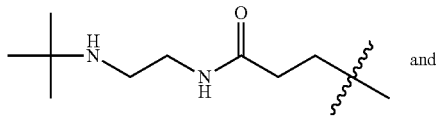 and

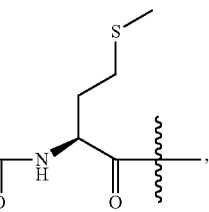

11. The compound of claim 9 wherein —NH—$R^9$ is:

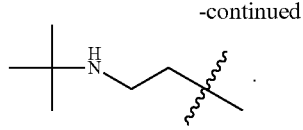

12. The compound of claim 10, having the formula:

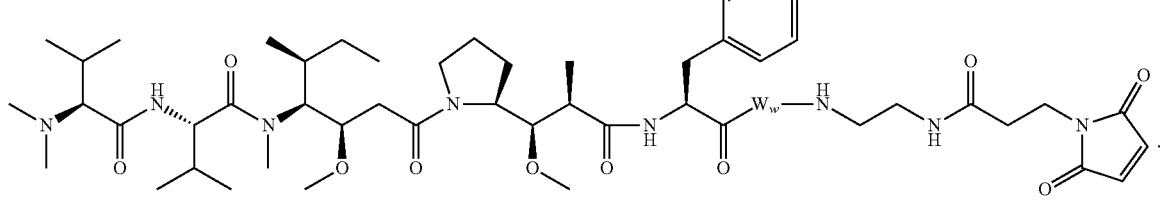

13. The compound of claim 1 or 2, wherein $W_1$ is a natural amino acid selected from the group consisting of alanine, arginine, aspartic acid, asparagine, histidine, glycine, glutamic acid, glutamine, phenylalanine, lysine, leucine, serine, tyrosine, threonine, isoleucine, tryptophan and valine.

14. The compound of claim 1 or 2, wherein the remaining Ws are independently selected from the D-isomers of the group consisting of alanine, arginine, aspartic acid, asparagine, histidine, glycine, glutamic acid, glutamine, phenylalanine, lysine, leucine, serine, tyrosine, threonine, isoleucine, tryptophan and valine.

15. The compound of claim 14, wherein $W_1$ is Methionine or Asparagine.

16. The compound of claim 1 or 2, wherein w is 2.

17. The compound of claim 1 or 2, wherein $W_w$ is selected from the group consisting of -Tyrosine-(D)Aspartic Acid-, -Norvaline-(D)Aspartic Acid-, -Phenylglycine-(D)Lysine-, -Methionine-(D)Lysine- and -Asparagine-(D)Lysine-.

18. The compound of claim 1 or 2, wherein $R^{12}$ is selected from the group consisting of the side chain of phenylalanine, methionine and tryptophan.

19. The compound of claim 1 or 2, wherein p is 2 to 8.

20. The compound of claim 19, wherein p is 2 to 5.

21. The compound of claim 1, wherein L is an antibody.

22. The compound of claim 21, wherein the antibody (Ab) is attached to each Amino Acid unit ($W_w$) through a cysteine residue of the antibody and the compound has the following formula:

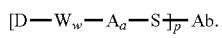

23. The compound of claim 22, having the formula:

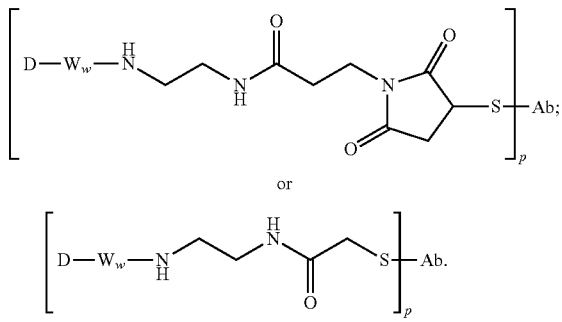

24. The compound of claim 21, wherein the antibody is a monoclonal antibody.

25. The compound of claim 21, wherein the antibody is a bispecific antibody.

26. The compound of claim 21, wherein the antibody is a humanized antibody.

27. The compound of claim 21, wherein the antibody is an antibody fragment.

28. The compound of claim 21, wherein the antibody specifically binds to a B cell antigen.

29. The compound of claim 1 or 2, or a pharmaceutically acceptable salt or solvate thereof, that is in isolated and purified form.

30. The compound of claim 21, wherein the antibody specifically binds to CD19, CD20, CD30, CD33, CD70, BCMA, or Lewis Y antigen.

31. A pharmaceutical composition comprising an effective amount of the compound of claim 1, or a pharmaceutically acceptable salt thereof, and a pharmaceutically acceptable diluent, carrier or excipient.

32. A method for killing or inhibiting the proliferation of tumor cells or cancer cells comprising treating tumor cells or cancer cells in a patient with an amount of the compound of claim 1, or a pharmaceutically acceptable salt or solvate thereof, said amount being effective to kill or inhibit the proliferation of the tumor cells or cancer cells.

33. A method for treating cancer comprising administering to a patient in need thereof an amount of the compound of claim 1, or a pharmaceutically acceptable salt or solvate thereof, said amount being effective to treat cancer.

34. The method of claim 33, further comprising administering an effective amount of an additional anticancer agent.

35. A method for killing activated lymphocytes associated with an autoimmune disease comprising administering to a patient with an autoimmune disease an amount of the compound of claim 1, or a pharmaceutically acceptable salt or solvate thereof, the amount being effective to kill activated lymphocytes associated with the autoimmune disease in the patient.

36. A method for treating an infectious viral disease comprising administering to a patient in need thereof an amount of the compound of claim 1, or a pharmaceutically acceptable salt or solvate thereof, the amount being effective to kill or inhibit the proliferation of virus infected cells in the patient.

37. The method of any one of claims 32-36, wherein the compound is in a formulation comprising a pharmaceutically acceptable diluent, carrier or excipient.

38. The method of any one of claims 32-36, wherein the amount of compound administered to the patient is in the range of about 0.1 to about 10 mg/kg of the patient's weight.

39. The method of claim 38, wherein the compound is administered at about three week intervals.

40. The method of any one of claims 32-36, wherein the compound is administered intravenously.

41. The method of claim 37, wherein the compound is formulated in a unit dosage injectable form.

42. The method of any one claims 32-36, wherein the patient is a human.

43. A method of determining inhibition of cellular proliferation by a compound, comprising: exposing mammalian cells in a cell culture medium to the compound of claim 21, and measuring a cytotoxic activity of the compound, whereby proliferation of the cells is inhibited.

44. The method of claim 43, further comprising culturing the cells for a period from about 6 hours to about 5 days.

45. A method of inhibiting the growth of tumor cells that overexpress a tumor-associated antigen comprising administering to a patient with said tumer cells the compound of claim 21 which binds specifically to said tumor-associated antigen, and a chemotherapeutic agent wherein the compound and said chemotherapeutic agent are each administered in amounts effective to inhibit growth of tumor cells in the patient.

46. The method of claim 45, wherein the compound sensitizes the tumor cells to said chemotherapeutic agent.

* * * * *